US010669343B2

(12) United States Patent
Fransson et al.

(10) Patent No.: US 10,669,343 B2
(45) Date of Patent: Jun. 2, 2020

(54) ANTI-CD154 ANTIBODIES AND METHODS OF USING THEM

(71) Applicant: Janssen Biotech, Inc., Horsham, PA (US)

(72) Inventors: Johan Fransson, Toronto (CA); Galina Obmolova, Spring House, PA (US); Anish Suri, Beerse (BE); Fang Teng, Spring House, PA (US); Alexey Teplyakov, Spring House, PA (US); Hong Zhou, San Diego, CA (US); Jocelyn Leu, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 516 days.

(21) Appl. No.: 15/228,582

(22) Filed: Aug. 4, 2016

(65) Prior Publication Data

US 2017/0037136 A1    Feb. 9, 2017

Related U.S. Application Data

(60) Provisional application No. 62/367,660, filed on Jul. 28, 2016, provisional application No. 62/201,150, filed on Aug. 5, 2015.

(51) Int. Cl.
*A61K 39/395* (2006.01)
*C07K 16/28* (2006.01)
*A61K 45/06* (2006.01)

(52) U.S. Cl.
CPC .......... *C07K 16/2875* (2013.01); *A61K 45/06* (2013.01); *C07K 2317/21* (2013.01); *C07K 2317/24* (2013.01); *C07K 2317/52* (2013.01); *C07K 2317/55* (2013.01); *C07K 2317/56* (2013.01); *C07K 2317/565* (2013.01); *C07K 2317/71* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,208,020 A | 5/1993 | Chari et al. |
| 5,223,409 A | 6/1993 | Ladner et al. |
| 5,225,539 A | 7/1993 | Winter |
| 5,403,484 A | 4/1995 | Ladner et al. |
| 5,565,332 A | 10/1996 | Hoogenboom et al. |
| 5,571,698 A | 11/1996 | Ladner et al. |
| 5,580,717 A | 12/1996 | Dower et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,869,620 A | 2/1999 | Whitlow et al. |
| 5,877,296 A | 3/1999 | Hamann et al. |
| 5,885,793 A | 3/1999 | Griffiths et al. |
| 5,932,448 A | 8/1999 | Tso et al. |
| 5,969,108 A | 10/1999 | McCafferty et al. |
| 6,150,584 A | 11/2000 | Kucherlapati et al. |
| 6,172,197 B1 | 1/2001 | McCafferty et al. |
| 6,521,404 B1 | 2/2003 | Griffiths et al. |
| 6,544,731 B1 | 4/2003 | Griffiths et al. |
| 6,582,915 B1 | 6/2003 | Griffiths et al. |
| 6,593,081 B1 | 7/2003 | Griffiths et al. |
| 6,630,579 B2 | 10/2003 | Chari et al. |
| 6,818,749 B1 | 11/2004 | Kashmiri et al. |
| 6,833,441 B2 | 12/2004 | Wang et al. |
| 7,498,298 B2 | 3/2009 | Doronina et al. |
| 7,695,936 B2 | 4/2010 | Carter et al. |
| 7,709,226 B2 | 5/2010 | Foote |
| 8,871,204 B2 | 10/2014 | Brezski et al. |
| 2002/0119150 A1 | 8/2002 | Kirk et al. |
| 2003/0103978 A1 | 6/2003 | Deshpande et al. |
| 2003/0153043 A1 | 8/2003 | Carr et al. |
| 2003/0220473 A1 | 11/2003 | Prussak et al. |
| 2006/0193856 A1 | 8/2006 | Taylor et al. |
| 2007/0065439 A1 | 3/2007 | Green et al. |
| 2008/0119353 A1 | 5/2008 | Jia et al. |
| 2008/0305116 A1 | 12/2008 | Van Vlijmen et al. |
| 2009/0068109 A1 | 3/2009 | Das et al. |
| 2009/0118127 A1 | 5/2009 | Raghunathan |
| 2009/0182127 A1 | 7/2009 | Kjaergaard et al. |

(Continued)

FOREIGN PATENT DOCUMENTS

| | | |
|---|---|---|
| WO | 98001649 A1 | 3/1988 |
| WO | 9004036 A1 | 4/1990 |

(Continued)

OTHER PUBLICATIONS

Rudikoff et al , Proc Natl Acad Sci USA 79:1979-1983 (1982). (Year: 1982).*
Colman, Research in Immunology 145: 33-36 (1994) (Year: 1994).*
Kussie et al., J. Immunol. 152: 146-152 (1994). (Year: 1994).*
Chen et al., EMBO J., 14: 2784-2794 (1995). (Year: 1995).*
Vonderheide et al, Clin Cancer Res 19: 1035-1043 (2013). (Year: 2013).*
Jefferis, Nature Reviews / Drug Discovery 8: 226-234 (Mar. 2009) (Year: 2009).*
Aruffo et al., "The CD40 ligand, gp39, is defective in activated T cells from patients with X-linked hyper-IGm syndrome", Cell Press, vol. 72, Issue 2, pp. 291-300, Jan. 1993.
Karpusas et al., "Structure of CD40 Ligand in Complex with the Fab Fragment of a Neutralizing Humanized Anti body", Structure vol. 9, pp. 321-329, Apr. 2011.

(Continued)

*Primary Examiner* — Phillip Gambel
(74) *Attorney, Agent, or Firm* — Ice Miller LLP

(57) ABSTRACT

The present invention relates to antagonistic antibodies specifically binding CD154, polynucleotides encoding the antibodies or fragments, and methods of making and using the foregoing.

66 Claims, 11 Drawing Sheets

Specification includes a Sequence Listing.

(56) References Cited

U.S. PATENT DOCUMENTS

| | | | |
|---|---|---|---|
| 2010/0015133 | A1 | 1/2010 | Igawa et al. |
| 2010/0021477 | A1 | 1/2010 | Tsui et al. |
| 2010/0104573 | A1 | 4/2010 | Burkly et al. |
| 2010/0261620 | A1 | 10/2010 | Almagro et al. |
| 2010/0286374 | A1 | 11/2010 | Kannan et al. |
| 2011/0123532 | A1 | 5/2011 | Gurney et al. |
| 2012/0149876 | A1 | 6/2012 | Von Kreudenstein et al. |
| 2013/0030159 | A1 | 1/2013 | Han et al. |
| 2013/0323249 | A1 | 12/2013 | Zhou et al. |
| 2019/0068109 | A1 | 2/2019 | Chu et al. |

FOREIGN PATENT DOCUMENTS

| | | |
|---|---|---|
| WO | 90007861 A1 | 7/1990 |
| WO | 9201047 A1 | 1/1992 |
| WO | 9222653 A1 | 12/1992 |
| WO | 9308207 A1 | 4/1993 |
| WO | 93009812 A1 | 5/1993 |
| WO | 9410308 A1 | 5/1994 |
| WO | 9411026 A2 | 5/1994 |
| WO | 94013804 A1 | 6/1994 |
| WO | 95006480 A1 | 3/1995 |
| WO | 95006481 A1 | 3/1995 |
| WO | 95006666 A1 | 3/1995 |
| WO | 9515388 A1 | 6/1995 |
| WO | 9640918 A2 | 12/1996 |
| WO | 9714719 A1 | 4/1997 |
| WO | 9717446 A2 | 5/1997 |
| WO | 98044001 A1 | 10/1998 |
| WO | 99012566 A1 | 3/1999 |
| WO | 9945962 A1 | 9/1999 |
| WO | 99051258 A1 | 10/1999 |
| WO | 9957150 A2 | 11/1999 |
| WO | 2001002057 A2 | 1/2001 |
| WO | 0124823 A1 | 4/2001 |
| WO | 2001068860 A1 | 9/2001 |
| WO | 0243478 A2 | 6/2002 |
| WO | 02066630 A1 | 8/2002 |
| WO | 2005003175 A2 | 1/2005 |
| WO | 2006030220 A1 | 3/2006 |
| WO | 2006033702 A2 | 3/2006 |
| WO | 2006125201 A2 | 11/2006 |
| WO | 2008118356 A2 | 10/2008 |
| WO | 2009085462 A1 | 7/2009 |
| WO | 2009134776 A2 | 11/2009 |
| WO | 2011036460 A1 | 3/2011 |
| WO | 11066501 A1 | 6/2011 |
| WO | 2011131746 A2 | 10/2011 |
| WO | 2011143545 A1 | 11/2011 |
| WO | 2012005813 A1 | 1/2012 |
| WO | 2012022811 A1 | 2/2012 |
| WO | 2012052205 A1 | 4/2012 |
| WO | 2012058137 A2 | 5/2012 |
| WO | 2012118903 A2 | 9/2012 |
| WO | 2012138768 A2 | 10/2012 |
| WO | 2013055745 A2 | 4/2013 |
| WO | 2013056068 A1 | 4/2013 |
| WO | 2014093908 A2 | 6/2014 |

OTHER PUBLICATIONS

Xie et al., "Engineering of Novel Anti-CD40L Domain Antibody for Treatment of Autoimmune Diseases" Journal of Immunology, 192, pp. 4082-4092, 2014.
Int'l Search Report and Written Opinion dated Jan. 13, 2017 in Int'l Application No. PCT/US2016/45574.
NCBI P29965 CD40L Human (Jul. 22, 2015) [Retrieved from the Internet Oct. 17, 2016: <https://www.ncbi.nlm.nih.gov/protein/231718?sat=21&satkey=36941873>]; 100% identify to SEQ ID:1, 9 pages.
Gobburu, et al., "Pharmacokinetics/Dynamics of 5c8, a Monoclonal Antibody to CD154 (CD40 Ligand) Suppression of an Immune Response in Monkeys", The Journal of Pharmacology and Experimental Therapeutics, vol. 286, No. 2, pp. 925-930, (1998).
Kuwana, et al., "Effect of a single injection of humanized anti-CD154 monoclonal antibody on the platelet-specific autoimmune response in patients with immune thrombocytopenic purpura", Blood, vol. 103, No. 4, pp. 1229-1236, (Oct. 2003).
Xie, et al., "Engineering of a Novel Anti-CD40L Domain Antibody for Treatment of Automimmune Diseases", The Journal of Immunology, vol. 192, No. 9, pp. 4083-4092, (Mar. 2014).
Robles-Carrillo, et al., "Anti-CD40L Immune Complexes Potently Activate Platelets In Vitro and Cause Thrombosis in FCGR2A Transgenic Mice", The Journal of Immunology, vol. 185, No. 3, pp. 1577-1583, (Jun. 2010).
Langer, et al., "The role of CD40 in CD40L- and antibody-mediated platelet activation", Thrombosis and Haemost, vol. 93, No. 6, pp. 1137-1146, (Jun. 2005).
Pinelli, et al., "Novel insights into anti-CD40/CD154 immunotherapy in transplant tolerance", Immunotherapy, vol. 7, No. 4, pp. 399-410, (2015).
Knappik, et al., "Fully synthetic human combinatorial antibody libraries (HuCAL) based on modular consensus frameworks and CDRs randomized with trinucleotides", J. Mol. Bio., vol. 296, No. 1, pp. 57-86, (Feb. 2000).
Shi, et al., "De Novo Selection of High-Affinity Antibodies from Synthetic Fab Libraries Displayed on Phage as pIX Fusion Proteins", Journal of Molecular Biology, vol. 397, No. 2, pp. 385-396, (Mar. 2010).
Partial European Search Report dated Apr. 12, 2019 in European Application No. 16833880.4.
Extended European Search Report dated Aug. 2, 2019 in Euopean Application No. 16833880.4.
Mackey, et al., "The role of CD40/CD154 interactions in the priming, differentiation, and effector function of helper and cytotoxic T cells", Journal of Leukocyte Biology, vol. 63, pp. 418-428, (Apr. 1998).
Quezada, et al., "CD40/CD154 interactions at the interface of tolerance and immunity," Annu Rev Immunol., vol. 22, pp. 307-328 (2004).
Padlan, Eduardo A., "A possible procedure for reducing the immunogenicity of antibody variable domains while preserving their ligand-binding properties", Molecular Immunology, vol. 28, No. 4-5, pp. 489-498, (May 1991).
Osbourn, et al., "From rodent reagents to human therapeutics using antibody guided selection", Methods, vol. 36, No. 1, pp. 61-68 (May 2005).
Gordon, et al., "Prolonged Survival of Rat Islet and Skin Xenografts in Mice Treated with Donor Splenocytes and Anti-CD154 Monoclonal Antibody," Diabetes, vol. 47, No. 8, pp. 1199-1206, (Aug. 1998).
Markees, et al., "Prolonged Survival of Mouse Skin Allografts in Recipients Treated With Donor Splenocytes and Antibody to CD40 Ligand1", Transplantation, vol. 64, No. 2, pp. 329-335, (Jul. 1997).
Jarvinen, et al., "CD154 on the Surface of CD4 CD25 Regulatory T Cells Contributes to Skin Transplant Tolerance", Transplantation, vol. 76, No. 9, pp. 1375-1375, (Nov. 2003).
Quezada, et al., "Mechanisms of donor-specific transfusion tolerance: preemptive induction of clonal T-cell exhaustion via indirect presentation", Blood, vol. 102, No. 5, pp. 1920-1926, (Sep. 2003).
Frleta, et al., "Distinctive Maturation of In Vitro Versus In Vivo Anti-CD40 mAb-Matured Dendritic Cells in Mice", Journal of Immunotherapy, vol. 26, No. 1, pp. 72-84, (2003).
Elster, et al. "Treatment with the Humanized CD154-Specific Monoclonal Antibody hu5C8, Prevents Acute Rejection of Primary Skin Allografts in Nonhuman Primates", Transplantation, vol. 72, No. 9, pp. 1473-1478, (Nov. 2001).
Benda, et al., "Co-Stimulatory Molecules in Islet Xenotransplantation: CTLA4Ig Treatment in CD40 Ligand-Deficient Mice", Cell Transplantation, vol. 11, pp. 715-720, (2002).
Wekerle, et al., "Mixed Chimerism and Transplantation Tolerance", Annual review of medicine, vol. 52, pp. 353-370, (Feb. 2001).
Camirand, et al., "Treatment With Anti-CD154 Antibody and Donor-Specific Transfusion Prevents Acute Rejection of Myoblast Transplantation", Transplantation, vol. 73, No. 3, pp. 453-461, (Feb. 2002).

(56) References Cited

OTHER PUBLICATIONS

Osborn, et al., "High-affinity IgG antibodies develop naturally in Ig-knockout rats carrying germline human IgH/Igk/Igl loci bearing the rat CH region", Journal of Immunology, vol. 190, pp. 1481-1490, (Jan. 2013).

Yazdany, et al., "The role of CD40 ligand in systemic lupus erythematosus", Lupus, vol. 13, pp. 377-380, (2004).

Dall'Acqua, et al., "Properties of Human IgG1s Engineered for Enhanced Binding to the Neonatal Fc Receptor (FcRn)", Journal of Biological Chemistry, vol. 281, No. 33, pp. 23514-23524, (Aug. 2006).

* cited by examiner

Figure 6A.

```
          1                             30
Human     MIETYNQTSPRSAATGLPISMKIFMYLLTV
Marmoset  MIETYNQPVPRSAATGPPVSMKIFMYLLTV
          *******.******* *:***********

31                            60
Human     FLITQMIGSALFAVYLHRRLDKIEDERNLH
Marmoset  FLITQMIGSALFAVYLHRRLDKIEDERNLH
          *****************************

61                            90
Human     EDFVFMKTIQRCNTGERSLSLLNCEEIKSQ
Marmoset  EDFVFMKTIQRCNTGERSLSLLNCEEIKSQ
          *****************************

91                           120
Human     FEGFVKDIMLNKEETKKENSFEMQKGDQNP
Marmoset  FEGFVKDIMLNKEEKKKENSFEMQKGDQNP
          *************.***************

121                          150
Human     QIAAHVISEASSKTTSVLQWAEKGYYTMSN
Marmoset  QIAAHVISEASSKTTSVLQWAEKGYYTMSN
          *****************************

151                          180
Human     NLVTLENGKQLTVKRQGLYYIYAQVTFCSN
Marmoset  NLVTLENGKQLTVKRQGLYYIYAQVTFCSN
          *****************************
```

Figure 6B.

```
          181                                              210
Human     REASSQAPFIASLCLKSPGRFERILLRAAN
Marmoset  REASSQAPFIASLCLKPPNRFERILLRAAN
          *************** * **********

211                                              240
Human     THSSAKPCGQQSIHLGGVFELQPGASVFVN
Marmoset  THSSAKPCGQQSIHLGGIFELQPGASVFVN
          ***************** ************

241                   261
Human     VTDPSQVSHGTGFTSFGLLKL
Marmoset  VTDPSQVSHGTGFTSFGLLKL
          *********************
```

ANTI-CD154 ANTIBODIES AND METHODS OF USING THEM

CROSS-REFERENCE TO RELATED APPLICATION

This application claims the benefit of U.S. Provisional Application Ser. No. 62/367,660, filed 28 Jul. 2016, and U.S. Provisional Application Ser. No. 62/201,150 filed 5 Aug. 2015, the entire contents of the aforementioned applications are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "JBI5068USNPSEQLIST.txt", creation date of Aug. 4, 2016, and having a size of 70.7 KB. The sequence listing submitted via EFS-Web is part of the specification and is herein incorporated by reference in its entirety.

FIELD OF THE INVENTION

The present invention relates to antibodies specifically binding CD154, polynucleotides encoding the antibodies or fragments, and methods of making and using the foregoing.

BACKGROUND OF THE INVENTION

CD154, also known as CD40 ligand (CD40L), gp39, TNF-related activation protein (TRAP), 5c8 antigen, or T-BAM, is a trimeric transmembrane protein of the tumor necrosis factor (TNF) superfamily. CD154 is expressed in an activation-dependent, temporally-restricted manner on the surface of $CD4^+$ T cells. CD154 is also expressed, following activation, on a subset of $CD8^+$ T cells, basophils, mast cells, eosinophils, natural killer cells, B cells, macrophages, dendritic cells and platelets. CD154 also exists as a soluble form in the blood.

CD154 binds to CD40 on antigen-presenting cells (APC), which leads to various responses depending on the target cell type. CD40-CD154 interaction is essential for normal T-B cell interactions, including increased co-stimulation, T-cell priming, cytokine production, antibody-class switching and affinity maturation, and antibody and autoantibody production.

Disruption of the CD40/CD154 pathway via CD154 blockage has been shown to be beneficial in autoimmune diseases such as systemic lupus erythematosus (SLE), rheumatoid arthritis (RA), multiple sclerosis (MS), inflammatory bowel disease (IBD), type I diabetes (T1D), and allograft rejection. In humans, mutations in either CD40 or CD154 result in hyper-IgM syndrome characterized by lack of IgG or IgA isotypes (Aruffo et al., Cell 72:291, 1993).

Anti-CD154 antibodies have been described for example in Int. Pat. Publ. Nos. WO1993/08207, WO1994/10308, WO1996/40918, WO1993/009812, WO1999/051258, WO1995/006480, WO1995/006481, WO1995/006666, WO2001/002057, WO1997/017446, WO1999/012566, WO2001/068860, WO2005/003175, WO2006/033702, WO2006/030220, WO2008/118356, WO2012/052205, WO2012/138768, WO2012/138768, WO2013/055745 and WO2013/056068.

Anti-CD154 antibodies have shown to be efficacious in the treatment of autoimmune diseases in humans. However, thromboembolism due to platelet activation observed upon treatment prohibited continued clinical development. Engagement of FcγRIIa on platelets has been shown to be causative for platelet activation by the anti-CD154 antibody 5c8 (Xie et al., J Immunol 192:4083-4092, 2014).

Thus, there is a need for additional anti-CD154 antibodies with improved safety and efficacy profiles.

SUMMARY OF THE INVENTION

The invention provides for an antagonistic antibody or an antigen binding portion thereof specifically binding human CD154 of SEQ ID NO: 1, comprising a heavy chain complementarity determining region (HCDR) 1 of SEQ ID NO: 17 (SYGIS), a HCDR2 of SEQ ID NO: 23 (WISPIF-GNTNYAQKFQG) and a HCDR3 of SEQ ID NO: 30 (SRYYGDLDY), wherein optionally the HCDR1 residue 51 is mutated to A, C, D, E, G, I, K, L, M, N, Q, R, T or V;
the HCDR1 residue 14 is mutated to M, L or V;
the HCDR1 residue S5 is mutated to A;
the HCDR2 residue S3 is mutated to A, T or V;
the HCDR2 residue P4 is mutated to V, T, L Q or E;
the HCDR2 residue N8 is mutated to A, C, D, E, F, G, H, I, K, L, M, Q, R, S, T, V, W or Y;
the HCDR2 residue T9 is mutated to A, C, D, E, F, G, H, I, K, L, M, Q, R, S, T, V, W or Y;
the HCDR2 residue N10 is mutated to A, C, D, E, F, G, H, I, K, L, M, Q, R, S, T, V, W or Y;
the HCDR3 residue Si is mutated to A or M;
the HCDR3 residue R2 is mutated to A, S, Q or K; and
the HCDR3 residue L7 is mutated to M.

The invention also provides for an isolated antagonistic antibody specifically binding CD154 of SEQ ID NO: 1, wherein the antibody comprises certain VH and VL amino acid sequences as described herein.

The invention also provides for an isolated antagonistic antibody specifically binding CD154 of SEQ ID NO: 1, wherein the antibody comprises certain HCDR1, HCDR2, HCDR3, LCDR1, LCDR2 and LCDR3 amino acid sequences as described herein.

The invention also provides for an isolated antagonistic antibody specifically binding CD154 of SEQ ID NO: 1 comprising the HCDR1, the HCDR2, the HCDR3, the LCDR1, the LCDR2 and the LCDR3 of SEQ ID NOs: 17, 23, 30, 37, 44 and 52, respectively;
the VH of SEQ ID NO: 59 and the VL of SEQ ID NO: 66; or
the heavy chain of SEQ ID NO: 80 and the light chain of SEQ ID NO: 81.

The invention also provides for an isolated antagonistic antibody or an antigen binding portion thereof specifically binding CD154 of SEQ ID NO: 1, wherein CD154 is a homotrimer and the antibody binds a first CD154 monomer in the homotrimer within amino acid residues 182-207 of CD154 and a second CD154 monomer in the homotrimer within amino acid residues 176-253 of CD154, wherein residue numbering is according to SEQ ID NO: 1.

The invention also provides for an immunoconjugate comprising the antibody or antigen-binding portion of the antibody of the invention linked to a therapeutic agent or an imaging agent.

The invention also provides for a pharmaceutical composition comprising the antibody of the invention and a pharmaceutically accepted carrier.

The invention also provides for a polynucleotide encoding the antibody VH of the invention, the antibody VL of the invention, or the antibody VH and VL of the invention.

The invention also provides for a vector comprising the polynucleotide of the invention.

The invention also provides for a host cell comprising the vector of the invention.

The invention also provides for a method of producing an antibody, comprising culturing the host cell of the invention in conditions that the antibody is expressed, and recovering the antibody produced by the host cell.

The invention also provides for a method of treating an autoimmune disease or an immune-mediated inflammatory disease comprising administering a therapeutically effective amount of the isolated antibody of the invention or a pharmaceutical composition of the invention to a patient in need thereof for a time sufficient to treat the disease.

The invention also provides for an anti-idiotypic antibody binding to the antibody of the invention.

The invention also provides for a kit comprising the antibody of the invention.

BRIEF DESCRIPTION OF THE DRAWINGS

FIG. 6A shows the alignment of residues 1-180 of human CD154 (SEQ ID NO: 1, top row) and marmoset CD154 (SQ ID NO: 2, bottom row) showing that the C4LB89 epitope residues are conserved between human and marmoset CD1514. Epitope residues on CD154 monomer 1 are underlined, and epitope residues on monomer 2 are double underlined.

FIG. 6B shows the alignment of residues 181-261 of human CD154 (SEQ ID NO: 1, top row) and marmoset CD154 (SQ ID NO: 2, bottom row) showing that the C4LB89 epitope residues are conserved between human and marmoset CD1514. Epitope residues on CD154 monomer 1 are underlined, and epitope residues on monomer 2 are double underlined.

DETAILED DESCRIPTION OF THE INVENTION

Figure 1:
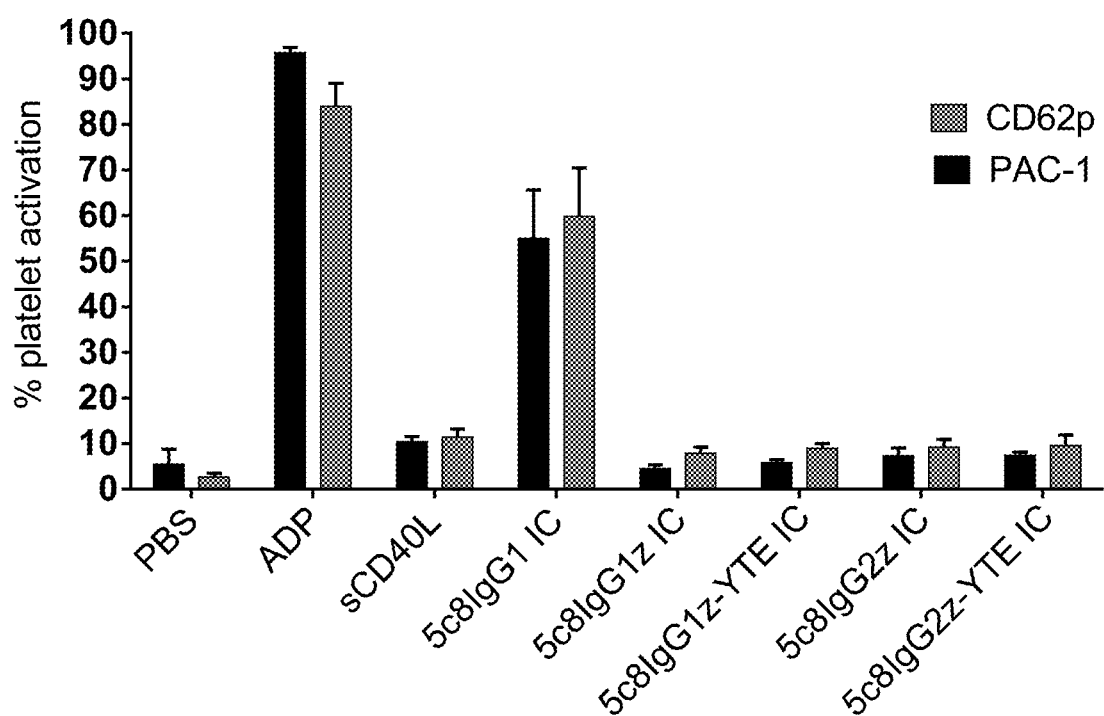
FIG. 1 shows the effect of antibody Fc on platelet activation by CD154:antibody immune complexes (IC). IC of soluble human CD154 (shCD154, indicated as sCD40L in the Figure) and anti-CD154 antibody 5c8 (IgG1 isotype) (5c8IgG1 IC) activated platelets, whereas IC of shCD154 and 5c8 cloned on silenced IgG1 backbones IgG1sigma, IgG1sigma-YTE, IgG2sigma or IgG2sigma-YTE (5c8IgG1z, 5c8IgG1z-YTE, 5c8IgG2z or 5c8IgG2z-YTE, respectively) had no effect. Platelet activation was assessed as % of total platelets expressing PAC-1 (PAC-1 antibody specifically recognizes conformational active form of αIIbβ3 integrin) and CD62p (P-selectin surface expression). ADP: positive control. PBS: negative control. Five donors were evaluated for platelet activation. The results are shown as mean of each experiment±SD.

All publications, including but not limited to patents and patent applications cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

As used herein and in the claims, the singular forms "a," "and," and "the" include plural reference unless the context clearly dictates otherwise.

Although any methods and materials similar or equivalent to those described herein may be used in the practice for testing of the present invention, exemplary materials and methods are described herein. In describing and claiming the present invention, the following terminology will be used.

"Specific binding" or "specifically binds" or "binds" refers to antibody binding to an antigen or an epitope within the antigen with greater affinity than for other antigens. Typically, the antibody binds to the antigen or the epitope within the antigen with a dissociation constant ($K_D$) of about $1×10^{-8}$ M or less, for example about $1×10^{-9}$ M or less, about $1×10^{-10}$ M or less, about $1×10^{-11}$ M or less, or about $1×10^{-12}$ M or less, typically with a $K_D$ that is at least one hundred fold less than its $K_D$ for binding to a non-specific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

"Neutralizing" or "neutralizes" or "neutralizing antibody" or "antibody antagonist" or "antagonist" or "antagonistic" refers to an antibody or an antigen binding portion thereof that partially or completely inhibits biological activity of human CD154. Antagonistic antibodies may be identified using assays for CD154 biological activity as described herein. Antagonistic antibody that specifically binds human CD154 may inhibit biological activity of human CD154 by about 20%, 30%, 40%, 50%, 60%, 70%, 75%, 80%, 85%, 90%, 95%, 96%, 97%, 98%, 99% or 100%.

"CD154" refers to human CD154 (hCD154) (e.g. human CD40L) protein. Human CD154 full length protein amino acid sequence is shown in SEQ ID NO: 1. Human CD154 is found both on cell membrane as type II membrane protein and exists as soluble form in plasma. CD154 membrane bound form comprises residues 1-261 of SEQ ID NO: 1, with transmembrane domain positioned between residues 23-46 and the extracellular domain spanning residues 47-261. The soluble form of human CD154 (shCD154) is formed by proteolytic processing of the membrane bound form, and comprises the residues 113-261 of SEQ ID NO: 1 (shCD154 amino acid sequence is shown in SEQ ID NO: 4). Both membrane bound and soluble CD154 form biologically active trimers. "CD154" encompasses the various forms of CD154, including monomer, dimer, trimer, membrane bound and soluble forms as well as naturally occurring variants of human CD154. Soluble human CD154 timer (shCD154 timer) is composed of three polypeptide chains each having the amino acid sequence of SEQ ID NO: 4.

"Antibodies" as used herein is meant in a broad sense and includes immunoglobulin molecules including monoclonal antibodies including murine, human, humanized and chimeric monoclonal antibodies, antibody fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full antibody molecules" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of antibody variable domains which are hypervariable in structure as defined by Chothia and Lesk (Chothia and Lesk, Mol Biol 196:901-17, 1987). The International ImMunoGeneTics (IMGT) database (www_imgt_org) provides a standardized numbering and definition of antigen-binding sites. The correspondence between CDRs, HVs and IMGT delineations is described in Lefranc et al., Dev Comparat Immunol 27:55-77, 2003. The terms "CDR", "HCDR1", "HCDR2", "HCDR3", "LCDR1", "LCDR2" and "LCDR3" includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (i), based on the amino acid sequences of their constant domains.

"Antibody fragments" or "antigen binding portion of an antibody" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include well known Fab, F(ab')2, Fd and Fv fragments as well as domain antibodies (dAb) consisting one VH domain. VH and VL domains may be linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Monoclonal antibody" refers to an antibody population with single amino acid composition in each heavy and each light chain, except for possible well known alterations such as removal of C-terminal lysine from the antibody heavy chain. Monoclonal antibodies typically bind one antigenic epitope, except that bispecific monoclonal antibodies bind two distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Isolated antibody" refers to an antibody or antibody fragment that is substantially free of other antibodies having different antigenic specificities (e.g., an isolated antibody specifically binding CD154 is substantially free of antibodies that specifically bind antigens other than CD154. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

"Chothia residues" are the antibody VL and VH residues numbered according to Al-Lazikani (Al-Lazikani et al., J Mol Biol 273:927-48, 1997).

"Humanized antibodies" refers to antibodies in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human antibodies" refers to antibodies having heavy and light chain variable regions in which both the framework and the antigen binding site are derived from sequences of human origin. If the antibody contains a constant region or a portion of the constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. "Human antibody" may contain amino acid differences when compared to the human germline or rearranged immunoglobulin sequences due to for example naturally occurring somatic mutations or intentional introduction of substitutions into the framework or antigen binding site, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000, or synthetic HCDR3 incorporated into human immunoglobulin gene libraries displayed on phage, for example as described in Shi et al., J Mol Biol 397:385-96, 2010 and Int. Pat. Publ. No. WO2009/085462.

Isolated humanized antibodies are synthetic. Human antibodies, while derived from human immunoglobulin sequences, may be generated using systems such as phage display incorporating synthetic CDRs and/or synthetic frameworks, or may be subjected to in vitro mutagenesis to improve antibody properties, resulting in antibodies that are not expressed by the human antibody germline repertoire in vivo.

Antibodies in which antigen binding sites are derived from a non-human species are not included in the definition of "human antibody".

"Recombinant" includes antibodies and other proteins that are prepared, expressed, created or isolated by recombinant means.

"Epitope" as used herein refers to a portion of an antigen to which an antibody specifically binds. Epitopes usually consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Paratope" refers to a portion of an antibody to which an antigen specifically binds. A paratope may be linear in nature or may be discontinuous, formed by a spatial relationship between non-contiguous amino acids of an antibody rather than a linear series of amino acids. A "light chain paratope" and a "heavy chain paratope" or "light chain paratope amino acid residues" and "heavy chain paratope amino acid residues" refer to antibody light chain and heavy chain residues in contact with an antigen, respectively, or in general, "antibody paratope residues" refer to those antibody amino acids that are in contact with antigen.

"Bispecific" refers to an antibody that specifically binds two distinct antigens or two distinct epitopes within the same antigen. The bispecific antibody may have cross-reactivity to other related antigens or can bind an epitope that is shared between two or more distinct antigens.

"Multispecific" refers to an antibody that specifically binds at least two distinct antigen or at least two distinct epitopes within the same antigen. Multispecific antibody may bind for example two, three, four or five distinct antigens or distinct epitopes within the same antigen.

"In combination with" means that the drugs or therapeutics are administered to a subject such as human together in a mixture, concurrently as single agents or sequentially as single agents in any order.

"CD154 biological activity" refers to any activity occurring as a result of CD154 binding to its receptor CD40. CD154 biological activity may be for example CD154-mediated activation of CD40$^+$ B cells or dendritic cells (DC), or downstream activation of CD40 signaling pathways. CD154 biological activity may be measured using well known methods and methods described herein, such as measuring CD154-mediated B cell proliferation or B cell activation by assessing ICAM-1 up-regulation or increased cytokine production by the B cells, CD154-mediated DC activation by assessing increased surface expression of CD80 and/or CD86 or cytokine secretion by the DC cells, or activation of CD40 signaling pathway as assessed by reporter gene assays such as measuring secretion of secreted embryonic alkaline phosphatase (SEAP) by cells expressing SEAP under the control of NF-κB-inducible promoter.

"Vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" means a vector that can be utilized in a biological system or in a reconstituted biological system to direct the translation of a polypeptide encoded by a polynucleotide sequence present in the expression vector.

"Polynucleotide" means a molecule comprising a chain of nucleotides covalently linked by a sugar-phosphate backbone or other equivalent covalent chemistry. Double and single-stranded DNA and RNA are typical examples of polynucleotides.

"Polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as shown in Table 1.

TABLE 1

| Amino acid | Three-letter code | One-letter code |
| --- | --- | --- |
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

The present invention provides antagonistic antibodies specifically binding CD154 with high affinity and efficiently neutralizing CD154 biological activity. The invention is based, at least in part, on the identification that contrary to the current understanding that binding of the antibodies specifically binding CD154 to the FcγRIIa on platelets results in activation and aggregation of platelets and subsequent thromboembolism, it has been herein discovered that platelet activation also depends on the CD154 epitope the antibodies binds to. It has been discovered herein that antibodies of the invention binding certain epitope on CD154 which are capable of engaging FcγRIIa do not to mediate platelet activation. In addition, the antibodies of the invention are optionally Fc engineered to prevent triggering of additional unwanted immunostimulatory functions. Therefore, the antibodies of the invention may have more favorable safety profiles in the clinical setting when compared to existing antibodies specifically binding CD154.

CD154 is a target in autoimmunity, graft rejection and other immune-related diseases in mice, non-human primates (NHP) and humans. In several Phase II Clinical Trials, antibodies specifically binding CD154 have been shown to effectively block the activities of CD154 in vivo and ameliorate disease. CD154 antagonists are distinct from all other therapeutics in its impact on the immune response; they are the only therapeutics that can induce functional immunological tolerance, as demonstrated both in mice and monkeys. In mice, virtually all autoimmune disease models can be effectively ameliorated with CD154 antagonists (Noelle et al., Ann N Y Acad Sci 815: 384-391, 1997; Mackey et al., J Leukoc Biol 63: 418-428, 1998; Noelle, Agents Actions Suppl 49: 17-22, 1998; Quezada et al., Annu Rev Immunol 22: 307-328, 2004), with long-term remission observed.

The invention provides for an isolated antagonistic antibody or an antigen binding portion thereof specifically binding CD154 of SEQ ID NO: 1.

The invention also provides for an isolated antagonistic antibody or an antigen binding portion thereof specifically binding CD154, wherein CD154 is a homotrimer and the antibody binds a first CD154 monomer in the homotrimer within amino acid residues 182-207 of CD154 and a second CD154 monomer in the homotrimer within amino acid residues 176-253 of CD154, wherein residue numbering is according to SEQ ID NO: 1.

Such exemplary antibody is the antibody C4LB89. Since antibody C4LB235 and C4LB236 variable regions differ by one amino acid residue in the LCDR2 when compared to those of C4LB89, and since C4LB231 and C4LB232 have identical VH/VL sequences with C4LB89, it is expected that also these antibodies bind the same CD154 epitope as C4LB89. Antibodies that bind CD154 within residues 182-207 and 176-253 are incapable of activating platelets even when capable of engaging with FcγR, including FcγRIIa. Therefore, these antibodies may have improved safety profile when compared to other antagonistic antibodies specifically binding CD154.

The invention also provides for an antagonistic antibody or an antigen binding portion thereof specifically binding human CD154 of SEQ ID NO: 1, comprising a heavy chain complementarity determining region (HCDR) 1 of SEQ ID NO: 17 (SYGIS), a HCDR2 of SEQ ID NO: 23 (WISPIFGNTNYAQKFQG) and a HCDR3 of SEQ ID NO: 30 (SRYYGDLDY), wherein optionally the HCDR1 residue 51 is mutated to A, C, D, E, G, I, K, L, M, N, Q, R, T or V;
the HCDR1 residue 14 is mutated to M, L or V;
the HCDR1 residue S5 is mutated to A;
the HCDR2 residue S3 is mutated to A, T or V;
the HCDR2 residue P4 is mutated to V, T, L Q or E;
the HCDR2 residue N8 is mutated to A, C, D, E, F, G, H, I, K, L, M, Q, R, S, T, V, W or Y;
the HCDR2 residue T9 is mutated to A, C, D, E, F, G, H, I, K, L, M, Q, R, S, T, V, W or Y;
the HCDR2 residue N10 is mutated to A, C, D, E, F, G, H, I, K, L, M, Q, R, S, T, V, W or Y;
the HCDR3 residue 51 is mutated to A or M;
the HCDR3 residue R2 is mutated to A, S, Q or K; and the HCDR3 residue L7 is mutated to M.

In some embodiments, the antibody of the invention comprises a light chain complementarity determining region (LCDR) 1 of SEQ ID NO: 37 (RASQSISSYLN), a LCDR2 of SEQ ID NO: 44 (YANSLQS) and a LCDR3 of SEQ ID NO: 52 (QQSDSIPWT), wherein optionally the LCDR1 residue Q4 is mutated to A, C, D, E, F, G, H, I, K, L, M, N, R, S, T, V, W or Y;
the LCDR1 residue S5 is mutated to A, C, D, E, F, G, H, I, K, L, M, N, Q, R, T, V, W or Y;
the LCDR1 residue S7 is mutated to A, C, D, E, F, G, H, I, K, L, M, N, Q, R, T, V, W or Y;
the LCDR1 residue S8 is mutated to A, C, D, E, F, G, H, I, K, L, M, N, Q, R, T, V, W or Y;
the LCDR2 residue A2 is mutated to S;
the LCDR2 residue N3 is mutated to A, C, D, E, F, G, H, I, K, L, M, Q, R, S, T, V, W or Y;

the LCDR2 residue S4 is mutated to A, C, D, E, F, G, H, I, K, L, M, N, Q, R, T, V, W or Y;
the LCDR2 residue L5 is mutated to A, C, D, E, F, G, H, I, K, M, N, Q, R, S, T, V, W or Y;
the LCDR2 residue Q6 is mutated to E, D or N;
the LCDR2 residue S7 is mutated to A, C, D, E, F, G, H, I, K, L, M, N, Q, R, T, V, W or Y;
the LCDR3 residue S3 is mutated to A;
the LCDR3 residue D4 is mutated to N;
the LCDR3 residue S5 is mutated to A, C, D, E, F, G, H, I, K, L, M, N, Q, R, T, V, W or Y; and
the LCDR3 residue 16 is mutated to A, C, D, E, G, K, L, M, N, Q, R, S, T or V.

A crystal structure of a complex of antibody C4LB89 and CD154 revealed that the antibody binds CD154 with VH residues only. Further analyses indicated that certain substitutions as shown in Table 19 and Table 20 as indicated supra, in the CDRs of the antibody are not expected to affect the overall structure of the complex and therefore characteristics of the antibody.

In some embodiments, the antibody of the invention comprises a light chain complementarity determining region (LCDR) 1, a LCDR2 and a LCDR3 of
SEQ ID NOs: 36, 43 and 51, respectively;
SEQ ID NOs: 37, 44 and 52, respectively;
SEQ ID NOs: 38, 45 and 53, respectively;
SEQ ID NOs: 39, 46 and 54, respectively;
SEQ ID NOs: 40, 47 and 55, respectively;
SEQ ID NOs: 41, 47 and 56, respectively;
SEQ ID NOs: 42, 48 and 57, respectively;
SEQ ID NOs: 37, 49 and 52, respectively; or
SEQ ID NOs: 37, 50 and 52, respectively.

In some embodiments, the antibody of the invention comprises the LCDR1, the LCDR2 and the LCDR3 of SEQ ID NOs: 37, 44 and 52, respectively.

In some embodiments, the antibody of the invention comprises the HCDR1, the HCDR2, the HCDR3, the LCDR1, the LCDR2 and the LCDR3 of SEQ ID NOs: 17, 23, 30, 37, 44 and 52, respectively.

In some embodiments, the antibody of the invention comprises the HCDR1, the HCDR2, the HCDR3, the LCDR1, the LCDR2 and the LCDR3 of SEQ ID NOs: 17, 23, 30, 37, 49 and 52, respectively.

In some embodiments, the antibody of the invention comprises the HCDR1, the HCDR2, the HCDR3, the LCDR1, the LCDR2 and the LCDR3 of SEQ ID NOs: 17, 23, 30, 37, 50 and 52, respectively.

In some embodiments, an immune complex of the antibody of the invention and soluble human CD154 (shCD154) does not activate platelets, wherein platelet activation is measured by P-selectin surface expression on platelets.

Platelet activation is a well-known process that converts the smooth, nonadherent platelet into a sticky speculated particle that releases and expresses biologically active substances and acquires the ability to bind the plasma protein fibrinogen. Activation may also occur as a result of the physical stimulus of high fluid shear stress, such as that found at the site of a critical arterial narrowing (Quinn et al., 2005, Platelet Function: assessment, diagnosis, and treatment, Humana Press, pp. 3-20). Activation of platelets results in activation of intracellular signaling pathways resulting in upregulation of platelet surface expression of P-selectin and increased binding affinity of fibrinogen to integrin receptors αIIbβ3. Platelet activation may therefore be measured by measuring increased P-selectin surface expression or binding of probe ligand e.g. PAC-1 to αIIbβ3 integrin on platelets using for example flow cytometry. The antibodies of the invention do not activate human platelets when the antibody in complex with shCD154 does not elevate surface expression of P-selectin or increase binding of probe ligand (e.g. PAC-1) to αIIbβ3 integrin in statistically significant manner when compared to the surface expression of P-selectin and increased binding of probe ligand (e.g. PAC-1) to αIIbβ3 integrin induced by shCD154.

In some embodiments, the antibody of the invention has at least one of the following properties:
binds to CD154 with a dissociation constant ($K_D$) of about $5 \times 10^{-9}$ M or less, when the $K_D$ is measured using ProteOn™ XPR36 system at 25° C. in Dulbecco's phosphate buffered saline containing 0.03% polysorbate P20 and 100 µg/ml bovine serum albumin;
inhibits CD154-mediated human B cell proliferation with an $IC_{50}$ value of about $2.7 \times 10^{-9}$M or less; or
inhibits CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1 \times 10^{-8}$ M or less.

In some embodiments, the antibody of the invention binds CD154 with a dissociation constant ($K_D$) of about $5 \times 10^{-9}$ M or less, about $1 \times 10^{1}$ M or less, about $5 \times 10^{-10}$ M or less, about $1 \times 10^{-10}$ M or less, about $5 \times 10^{-11}$ M or less, or about $1 \times 10^{-11}$ M or less.

In some embodiments, the antibody specifically binding CD154 cross-reacts with *Macaca fascicularis* (cyno) CD154 or *Callithrix jacchus* (marmoset) CD154.

The affinity of an antibody to human, cyno or marmoset CD154 may be determined experimentally using any suitable method. Such methods may utilize ProteOn™ XPR36, Biacore 3000 or KinExA® instrumentation, ELISA or competitive binding assays known to those skilled in the art. The measured affinity of a particular antibody to CD154 may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn™ (measured as standard deviation, SD) can typically be within 5-33% for measurements within the typical limits of detection. Therefore the term "about" reflects the typical standard deviation in the assay. For example, the typical SD for a $K_D$ of $1 \times 10^{-9}$ M is up to $\pm 0.33 \times 10^{-9}$M.

In some embodiments, the antibody of the invention inhibits CD154-mediated human B cell proliferation with an $IC_{50}$ value of about $2.7 \times 10^{1}$ M or less.

In the B cell proliferation assay, $1 \times 10^{5}$ human tonsil B cells may be cultured with 100 ng/ml recombinant human IL-21, 0.5 µg/ml trimeric recombinant soluble human CD154 expressed as a leucine zipper fusion protein and anti-CD154 antibodies in a range of 0.000064-25 µg/ml in a final volume of 200 µl/well. After 2 days incubation methyl (−3H)-Thymidine (0.5 µCi/well) may be added to the cultures and effect of the antibodies on human B cell proliferation may be determined after overnight incubation.

In some embodiments, the antibody of the invention inhibits CD154-induced expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1 \times 10^{-8}$ M or less.

In some embodiments, the antibody of the invention inhibits CD154-induced expression of secreted embryonic alkaline phosphatase (SEAP) under NF-κB-inducible IFN-β minimal promoter in HEK293 cells stably expressing SEAP and human CD40 with an $IC_{50}$ value of between about $2.1 \times 10^{-8}$ M and $5.4 \times 10^{-10}$ M.

The cells that may be used are for example HEK-Blue™ CD40L cells (InvivoGen, San Diego, Calif.). Human CD154 may be provided as trimeric soluble CD154-leucine zipper fusion protein. Signal from the secreted alkaline phosphatase may be detected and an $IC_{50}$ may be calculated for the inhibition using well known methods.

In some embodiments, the antibody of the invention binds a first CD154 monomer and a second CD154 monomer simultaneously in a CD154 homotrimer.

In some embodiments, the antibody of the invention binds at least one, two, three, four, five, six, seven or eight CD154 residues in the first CD154 monomer within amino acid residues 182-207 of CD154 of SEQ ID NO: 1.

In some embodiments, the antibody of the invention binds at least one, two, three, four, five, six, seven or eight CD154 residues in the second CD154 monomer within amino acid residues 176-253 of CD154 of SEQ ID NO: 1.

In some embodiments, the antibody of the invention binds residues E182, S185, Q186, A187, P188, S214, A215 and 8207 in the first CD154 monomer, wherein residue numbering is according to SEQ ID NO: 1.

In some embodiments, the antibody of the invention binds residues T176, F177, C178, Q220, S248, H249, G250 and F253 in the second CD154 monomer, wherein residue numbering is according to SEQ ID NO: 1.

"Within" means that the antibody binds only residues inside the amino acid stretches 182-207, 176-354 or 182-207 and 176-354.

Such exemplary antibody is the antibody C4LB89. Since antibody C4LB235 and C4LB236 variable regions differ by one amino acid residue in the LCDR2 when compared to those of C4LB89, and since C4LB231 and C4LB232 have identical VH/VL sequences with C4LB89, it is expected that also these antibodies bind the same CD154 epitope as C4LB89.

In some embodiments, the antibody of the invention binds human CD154 with paratope residues that reside in the VH of the antibody.

"Paratope residue" is a residue in the antibody VH or VL that resides within 4 Å from the CD154 residues. Paratope residues may be identified from crystal structures of the complex of antibody with CD154.

An exemplary antibody that binds CD154 with VH paratope residues only without VL in contact with antigen is an antibody that comprises the VH and the VL of antibody C4LB89. Since C4LB235 and C4LB236 variable regions differ by one amino acid residue in the LCDR2 when compared to those of C4LB89, and since C4LB231 and C4LB232 have identical VH/VL sequences with C4LB89, it is expected that also these antibodies bind CD154 with VH residues only. Antibodies that bind CD154 within residues 182-207 or 176-354 of SEQ ID NO: 1 or residues E182, S185, Q186, A187, P188, S214, A215 and R207 in the first CD154 monomer and residues T176, F177, C178, Q220, S248, H249, G250 and F253 in the second CD154 monomer in the CD154 homotrimer are incapable of activating platelets even when capable of engaging with FcγR, including FcγRIIa. Therefore, these antibodies may have an improved safety provide when compared to other antibodies that specifically bind CD154.

In some embodiments, the antibody the invention comprises a heavy chain variable region (VH) of SEQ ID NO: 59, optionally the VH comprising one, two, three, four, five, six, seven, eight, nine, ten, eleven, twelve, thirteen, fourteen or fifteen amino acid substitutions.

In some embodiments, the antibody of the invention comprises the heavy chain variable region (VH) of SEQ ID NO: 59.

The antibody comprising the HCDR1, the HCDR2 and the HCDR3 of SEQ ID NOs: 17, 23 and 30, respectively, or having the HCDRs of VH of SEQ ID NO: 59 or the VH of SEQ ID NO: 59 binds CD154 with the antibody VH only. Therefore, the VH of SEQ ID NO: 59 or the VH comprising the HCDR1, the HCDR2 and the HCDR3 of SEQ ID NOs: 17, 23 and 30, respectively, may be combined with any light chain variable region (VL) sequence and the binding of the resulting antibody to CD154 may be tested using assays described herein to generate an antibody that specifically binds CD154.

For example, the VH comprising the HCDR1, the HCDR2 and the HCDR3 of SEQ ID NOs: 17, 23 and 30, respectively, or the VH of SEQ ID NO: 59 may be used to screen for VL domains capable of forming a two-domain specific antigen-binding fragment capable of binding to CD154. The screening may be accomplished by phage display screening methods using for example hierarchical dual combinatorial approach disclosed in PCT Publ. No. WO1992/01047. In this approach, an individual colony containing either a H or L chain clone, for example VH of SEQ ID NO: 59, is used to infect a complete library of clones encoding the other chain (L or H), and the resulting two-chain specific antigen-binding domain is selected in accordance with phage display techniques as described herein and tested for its binding and antagonistic activity towards CD154.

Alternatively, the VH or SEQ ID NO: 59 or the VH comprising the HCDR1, the HCDR2 and the HCDR3 of SEQ ID NOs: 17, 23 and 30, respectively, may be combined with VL domains of existing CD154 antibodies or CD154 antibodies described herein, and the resulting antibody is tested for its binding and antagonistic activity towards CD154.

In some embodiments, the antibody of the invention comprises a light chain variable region (VL) of SEQ ID NOs: 65, 66, 67, 68, 69, 70, 71, 72 or 73, optionally the VL comprising one, two, three, four, five, six, seven, eight, nine, ten, eleven, twelve, thirteen, fourteen or fifteen amino acid substitutions.

In some embodiments, the antibody of the invention comprises the VH of SEQ ID NO: 59 and the VL or SEQ ID NOs: 65, 66, 67, 68, 69, 70, 71, 72 or 73.

In some embodiments, the antibody of the invention comprises a light chain variable region (VL) of SEQ ID NOs: 66, 72 or 73, optionally the VL comprising one, two, three, four, five, six, seven, eight, nine, ten, eleven, twelve, thirteen, fourteen or fifteen amino acid substitutions.

In some embodiments, the antibody of the invention comprises the VH of SEQ ID NO: 59 and the VL of SEQ ID NO: 66.

In some embodiments, the antibody of the invention comprises the VH of SEQ ID NO: 59 and the VL of SEQ ID NO: 72.

In some embodiments, the antibody of the invention comprises the VH of SEQ ID NO: 59 and the VL of SEQ ID NO: 73.

In some embodiments, the antibody of the invention comprising at least one substitution in an Fc region, wherein the antibody does not activate human platelets.

In some embodiments, the antibody of the invention has reduced binding to FcγRI, FcγRIIa, FcγRIIb, FcγRIIIa or FcγRIIIb.

"Reduced binding" refers to reduced binding of the antibodies of the invention having at least one substitution in the Fc region to an FcγR receptor when compared to the binding of the parental antibody without the substitution to the same FcγR receptor. "Reduced binding" may be at least about 100-fold, at least about 500-fold, at least about 1000-fold, at least about 5000-fold, at least about 10,000-fold, or at least about 20,000-fold reduced binding. In practice, antibodies exhibiting "reduced binding" to a particular FcγR refer to antibodies that have statistically insignificant effector function mediated by the particular FcγR.

In some embodiments, the antibody of the invention comprises at least one substitution in the Fc region.

In some embodiments, the at least one substitution in the Fc region is a substitution L234A, L235A, G237A, P238S, M252Y, S254T, T256E, H268A, A330S or P331S, wherein residue numbering is according to the EU Index.

In some embodiments, the antibody of the invention comprises substitutions L234A, L235A, G237A, P238S, H268A, A330S or P331S in the Fc region, wherein residue numbering is according to the EU Index.

In some embodiments, the at least one substitution in the Fc region is a substitution V234A, G237A, P238S, M252Y, S254T, T256E H268A, V309L, A330S or P331S, wherein residue numbering is according to the EU Index.

In some embodiments, the antibody of the invention comprises substitutions V234A, G237A, P238S, H268A, V309L, A330S and P331S in the Fc region, wherein residue numbering is according to the EU Index.

The invention also provides for an antagonistic antibody or an antigen binding portion thereof specifically binding CD154 of SEQ ID NO: 1, comprising a heavy chain of SEQ ID NO: 80 and a light chain of SEQ ID NO: 81.

The invention also provides for an antagonistic antibody or an antigen binding portion thereof specifically binding CD154 of SEQ ID NO: 1, comprising a heavy chain of SEQ ID NO: 82 and a light chain of SEQ ID NO: 81.

The invention also provides for an antagonistic antibody or an antigen binding portion thereof specifically binding CD154 of SEQ ID NO: 1, comprising a heavy chain of SEQ ID NO: 83 and a light chain of SEQ ID NO: 81.

```
(C4LB89 VH on IgG1sigma: C4LB231 HC)
                                       SEQ ID NO: 80
QVQLVQSGAEVKKPGSSVKVSCKASGGTFSSYGISWVRQAPGQGLEWMG

WISPIFGNTNYAQKFQGRVTITADESTSTAYMELSSLRSEDTAVYYCAR

SRYYGDLDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPEAAGASSVFLFP

PKPKDTLMISRTPEVTCVVVDVSAEDPEVKFNWYVDGVEVHNAKTKPRE

EQYNSTYRVVSVLTVLHQDWLNGKEYKCKVSNKALPSSIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK
```

```
(Light chain of C4LB89 and C4LB231)
                                       SEQ ID NO: 81
DIQMTQSPSSLSASVGDRVTITCRASQSISSYLNWYQQKPGKAPKLLIY

YANSLQSGVPSRFSGSGSGTDFTLTISSLQPEDFATYYCQQSDSIPWTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC (C4LB89 VH on IgG1sigmaYTE)
                                       SEQ ID NO: 82
QVQLVQSGAEVKKPGSSVKVSCKASGGTFSSYGISWVRQAPGQGLEWMG

WISPIFGNTNYAQKFQGRVTITADESTSTAYMELSSLRSEDTAVYYCAR

SRYYGDLDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPEAAGASSVFLFP

PKPKDTLYITREPEVTCVVVDVSAEDPEVKFNWYVDGVEVHNAKTKPRE

EQYNSTYRVVSVLTVLHQDWLNGKEYKCKVSNKALPSSIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK (C4LB89 VH on IgG2sigma)
                                       SEQ ID NO: 83
QVQLVQSGAEVKKPGSSVKVSCKASGGTFSSYGISWVRQAPGQGLEWMG

WISPIFGNTNYAQKFQGRVTITADESTSTAYMELSSLRSEDTAVYYCAR

SRYYGDLDYWGQGTLVTVSSASTKGPSVFPLAPCSRSTSESTAALGCLV

KDYFPEPVTVSWNSGALTSGVHTFPAVLQSSGLYSLSSVVTVPSSNFGT

QTYTCNVDHKPSNTKVDKTVERKCCVECPPCPAPPAAASSVFLFPPKPK

DTLMISRTPEVTCVVVDVSAEDPEVQFNWYVDGVEVHNAKTKPREEQFN

STFRVVSVLTVLHQDWLNGKEYKCKVSNKGLPSSIEKTISKTKGQPREP

QVYTLPPSREEMTKNQVSLTCLVKGFYPSDIAVEWESNGQPENNYKTTP

PMLDSDGSFFLYSKLTVDKSRWQQGNVFSCSVMHEALHNHYTQKSLSLS

PGK
```

Immune effector properties of the antibodies of the invention may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. may be provided and/or controlled by modifying residues in the Fc responsible for these activities. For example, Fc substitutions V234A/G237A/P238S, V234A/G237A/H268Q, H268A/V309L/A330S/P331 or V234A/G237A/P238S/H268AN309L/A330S/P331S (Intl. Pat. Publ. No. WO11/066501) or L234A/L235A/G237A/P238S/H268A/A330S/P331S may be introduced to the antibodies of the invention.

Binding of the antibodies of the invention to FcγRI, FcγRIIa, FcγRIIb, FcγRIIIa and FcγRIIIb may be evaluated using recombinant soluble forms or cell-associated forms of the Fcγ receptors. For example, direct or indirect, e.g., competitive binding, measurements may be applied for assessing relative affinities and avidities of the antibodies of the invention to various FcγR. In an exemplary assay, test antibody binding to soluble FcγR captured on a plate is evaluated using competitive binding between 1 μg/ml biotinylated human IgG1 and serial dilutions of test antibody pre-complexed with antigen.

In some embodiments, the antibody of the invention has reduced antibody dependent cellular cytotoxicity (ADCC), antibody-dependent cellular phagocytosis" ("ADCP") and/or complement dependent cytotoxicity (CDC).

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcγRIIIa. To assess ADCC activity of the antibodies of the invention, the antibody may be added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include D1.1 Jurkat cells (ATCC® CRL-10915™) or T cells expressing CD154.

"Antibody-dependent cellular phagocytosis" ("ADCP") refers to a mechanism of elimination of antibody-coated target cells by internalization by phagocytic cells, such as macrophages or dendritic cells. ADCP may be evaluated using monocyte-derived macrophages as effector cells and D1.1 Jurkat cells expressing CD154 engineered to express GFP or other labeled molecule as target cells. Effctor:target cell ratio may be for example 4:1. Effector cells may be incubated with target cells for 4 hours with or without the test CD154 antibody. After incubation, cells may be detached using accutase. Macrophages may be identified with anti-CD11b and anti-CD14 antibodies coupled to a fluorescent label, and percent phagocytosis may be determined based on % GFP fluorescent in the CD11$^+$CD14$^+$ macrophages using standard methods.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of CD154-expressing cells may be measured for example by plating Jurkat cells in an appropriate medium, adding anti-CD154 antibodies into the mixture, followed by addition of pooled human serum. After incubation period, percentage (%) lysed cells may be detected as % propidium iodide stained cells in FACS assay using standard methods.

"Reduced ADCC", "reduced CDC" and "reduced ADCP" refers to antibody-induced ADCC, CDC and/or ADCP that is statistically insignificant in standard assays that measure ADCC, CDC and/or ADCP, such as assays described herein and in assays described in U.S. Pat. No. 8,871,204.

The antibodies of the invention with a desired affinity and neutralization profile may be selected from libraries of variants or fragments by panning with human CD154 or marmoset CD154 and optionally by further antibody affinity maturation. In an exemplary panning campaign, phage libraries may be panned with marmoset CD154. Alternatively, antibodies of the invention may be generated by immunizing mice with human CD154 or marmoset CD154 or both, and screening the hybriomas for binding to human CD154, and subsequently assessing the antagonistic properties of the antibodies using methods described herein.

In some embodiments, the antibody of the invention competes for binding to CD154 with an antibody comprising the VH of SEQ ID NO: 59 and the VL of SEQ ID NO: 66.

Competition between specific binding to CD154 with antibodies of the invention comprising certain VH and VL sequences may be assayed in vitro using well known methods. For example, binding of MSD Sulfo-Tag™ NHS-ester-labeled antibody to CD154 in the presence of an unlabeled antibody maybe assessed by ELISA, or Biacore analyses or flow cytometry may be used to demonstrate competition with the antibodies of the current invention. The antibody competes for binding to CD154 with a reference antibody (e.g. an antibody comprising the VH of SEQ ID NO: 59 and the VL of SEQ ID NO: 66) when the antibody inhibits binding of the reference antibody to CD154 by 80% or more, for example 85% or more, 90% or more, or 95% or more.

In some embodiments, the VH of SEQ ID NO: 59 may be combined with the VL of any of the anti-CD154 antibodies described in Int. Pat. Publ. Nos. WO1993/08207, WO1994/10308, WO1996/40918, WO1993/009812, WO1999/051258, WO1995/006480, WO1995/006481, WO1995/006666, WO2001/002057, WO1997/017446, WO1999/012566, WO2001/068860, WO2005/003175, WO2006/033702, WO2006/030220, WO2008/118356, WO2012/052205, WO2012/138768, WO2012/138768, WO2013/055745 and WO2013/056068 to generate an antagonistic anti-CD154 antibody. The binding and antagonistic activity of the resulting antibodies may be tested using assays and protocols described herein.

The invention also provides for an antagonistic antibody specifically binding a CD154 of SEQ ID NO: 1, comprising the HCDR1, the HCDR2 and the HCDR3 of
  SEQ ID NOs: 16, 22 and 29, respectively;
  SEQ ID NOs: 17, 23 and 30, respectively;
  SEQ ID NOs: 16, 24 and 31, respectively;
  SEQ ID NOs: 18, 25 and 32, respectively;
  SEQ ID NOs: 19, 26 and 33, respectively;
  SEQ ID NOs: 20, 27 and 34, respectively; or
  SEQ ID NOs: 21, 28 and 35, respectively.

The invention also provides for an antagonistic antibody specifically binding CD154 of SEQ ID NO: 1, comprising the HCDR1, the HCDR2 and the HCDR3 of
  SEQ ID NOs: 16, 22 and 29, respectively;
  SEQ ID NOs: 17, 23 and 30, respectively;
  SEQ ID NOs: 16, 24 and 31, respectively;
  SEQ ID NOs: 18, 25 and 32, respectively;
  SEQ ID NOs: 19, 26 and 33, respectively;
  SEQ ID NOs: 20, 27 and 34, respectively; or
  SEQ ID NOs: 21, 28 and 35, respectively, and the LCDR1, the LCDR2 and the LCDR3 of
  SEQ ID NOs: 36, 43 and 51, respectively;
  SEQ ID NOs: 37, 44 and 52, respectively;
  SEQ ID NOs: 38, 45 and 53, respectively;
  SEQ ID NOs: 39, 46 and 54, respectively;
  SEQ ID NOs: 40, 47 and 55, respectively;
  SEQ ID NOs: 41, 47 and 56, respectively;
  SEQ ID NOs: 42, 48 and 57, respectively;
  SEQ ID NOs: 37, 49 and 52, respectively; or
  SEQ ID NOs: 37, 50 and 52, respectively.

In some embodiments, the antibody of the invention comprises the HCDR1, the HCDR2 and the HCDR3 of SEQ ID NOs: 16, 22 and 29, respectively, and the LCDR1, the LCDR2 and the LCDR3 of SEQ ID NOs: 36, 43 and 51, respectively; or the VH of SEQ ID NO: 58 and the VL of SEQ ID NO: 65.

In some embodiments, the antibody of the invention comprises the HCDR1, the HCDR2 and the HCDR3 of SEQ ID NOs: 17, 23 and 30, respectively, and the LCDR1, the LCDR2 and the LCDR3 of SEQ ID NOs: 37, 44 and 52, respectively; or the VH of SEQ ID NO: 59 and the VL of SEQ ID NO: 66.

In some embodiments, the antibody of the invention comprises the HCDR1, the HCDR2 and the HCDR3 of SEQ ID NOs: 16, 24 and 31, respectively, and the LCDR1, the LCDR2 and the LCDR3 of SEQ ID NOs: 38, 45 and 53, respectively; or the VH of SEQ ID NO: 60 and the VL or SEQ ID NO: 67.

In some embodiments, the antibody of the invention comprises the HCDR1, the HCDR2 and the HCDR3 of SEQ ID NOs: 18, 25 and 32, respectively, and the LCDR1, the LCDR2 and the LCDR3 of SEQ ID NOs: 39, 46 and 54, respectively; or the VH of SEQ ID NO: 61 and the VL or SEQ ID NO: 68.

In some embodiments, the antibody of the invention comprises the HCDR1, the HCDR2 and the HCDR3 of SEQ ID NOs: 19, 26 and 33, respectively, and LCDR1, the LCDR2 and the LCDR3 of SEQ ID NOs: 40, 47 and 55, respectively; or the VH of SEQ ID NO: 62 and the VL or SEQ ID NO: 69.

In some embodiments, the antibody of the invention comprises the HCDR1, the HCDR2 and the HCDR3 of SEQ ID NOs: 20, 27 and 34, respectively, and the LCDR1, the LCDR2 and the LCDR3 of SEQ ID NOs: 41, 47 and 56, respectively; or the VH of SEQ ID NO: 63 and the VL or SEQ ID NO: 70.

In some embodiments, the antibody of the invention comprises the HCDR1, the HCDR2 and the HCDR3 of SEQ ID NOs: 21, 28 and 35, respectively, and the LCDR1, the LCDR2 and the LCDR3 of SEQ ID NOs: 42, 48 and 57, respectively; or the VH of SEQ ID NO: 64 and the VL or SEQ ID NO: 71.

In some embodiments, the antibody of the invention comprises the HCDR1, the HCDR2 and the HCDR3 of SEQ ID NOs: 17, 23 and 30, respectively, and LCDR1, the LCDR2 and the LCDR3 of SEQ ID NOs: 37, 49 and 52, respectively; or the VH of SEQ ID NO: 59 and the VL or SEQ ID NO: 72.

In some embodiments, the antibody of the invention comprises the HCDR1, the HCDR2 and the HCDR3 of SEQ ID NOs: 17, 23 and 30, respectively, and the LCDR1, the LCDR2 and the LCDR3 of SEQ ID NOs: 37, 50 and 52, respectively; or the VH of SEQ ID NO: 59 and the VL or SEQ ID NO: 73.

In some embodiments, the antibody of the invention comprises the VH and the VL wherein the VH comprises the amino acid sequence of SEQ ID NOs: 58, 59, 60, 61, 62, 63 or 64.

In some embodiments, the antibody of the invention comprises the VH and the VL, wherein the VL comprises the amino acid sequence of SEQ ID NOs: 65, 66, 67, 68, 69, 70, 71, 72 or 73.

In some embodiments, the antibody of the invention comprises the VH of SEQ ID NOs: 58, 59, 60, 61, 62, 63 or 64, and the VL of SEQ ID NOs: 65, 66, 67, 68, 69, 70, 71, 72 or 73.

In some embodiments, the antibody of the invention comprises the HCDR1, HCDR2 and HCDR3 amino acid sequences of the VH of SEQ ID NOs: 65, 66, 67, 68, 69, 70, 71, 72 or 73, and the LCDR1, LCDR2 and LCDR3 amino acid sequences of the VL of SEQ ID NOs: 65, 66, 67, 68, 69, 70, 71, 72 or 73, wherein the CDRs are defined according to Kabat, Chothia and/or IMGT.

Variants of the antibodies of the invention comprising the VH or the VL amino acid sequences shown in Table 8, Table 9 and Table 14 are within the scope of the invention. For example, variants may comprise one, two, three, four, five, six, seven, eight, nine, ten, eleven, twelve, thirteen, fourteen or fifteen amino acid substitutions in the VH and/or the VL that do not adversely affect the antibody properties. In some embodiments, the sequence identity may be about 90%, 91%, 92%, 93%, 94%, 95%, 96%, 97%, 98% or 99% to the VH or the VL amino acid sequence of the invention.

The percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences.

The percent identity between two amino acid sequences may be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J. Mol. Biol.* 48:444-453 (1970)) algorithm which has been incorporated into the GAP program in the GCG software package (available at www_gcg_com), using either a Blossum 62 matrix or a PAM250 matrix, and a gap weight of 16, 14, 12, 10, 8, 6, or 4 and a length weight of 1, 2, 3, 4, 5, or 6.

In some embodiments, the antibody of the invention comprises the VH that is at least 90%, 90%, 92%, 93%, 94%, 95%, 96%, 97%, 98%, 99% or 100% identical to the VH of SEQ ID NOs: 58, 59, 60, 61, 62, 63 or 64, wherein the antibody exhibits one or more of the following properties:
  an immune complex of the antibody and shCD154 does not activate platelets,
    wherein platelet activation is measured by P-selectin surface expression on platelets;
  binds to CD154 with a dissociation constant ($K_D$) of about $5\times10^{-9}$ M or less, when the $K_D$ is measured using ProteOn™XPR36 system using experimental design described in Example 1, affinity measurements;
  inhibits CD154-mediated human B cell proliferation with an $IC_{50}$ value of about $2.7\times10^{-9}$M or less; or
  inhibits CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about 2.1×10' M or less.

In some embodiments, the antibody of the invention comprises the VL that is at least 90%, 90%, 92%, 93%, 94%, 95%, 96%, 97%, 98%, 99% or 100% identical to the VL of SEQ ID NOs: 65, 66, 67, 68, 69, 70, 71, 72 or 73, wherein the antibody exhibits one or more of the following properties:
  an immune complex of the antibody and shCD154 does not activate platelets, wherein platelet activation is measured by P-selectin surface expression on platelets;

binds to CD154 with a dissociation constant ($K_D$) of about $5 \times 10^{-9}$ M or less, when the $K_D$ is measured using ProteOn™ XPR36 system using experimental design described in Example 1, affinity measurements;

inhibits CD154-mediated human B cell proliferation with an $IC_{50}$ value of about $2.7 \times 10^{-9}$M or less; or inhibits CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1 \times 10^{-8}$ M or less.

In some embodiments, the antibody of the invention comprises the VH that is at least 90%, 90%, 92%, 93%, 94%, 95%, 96%, 97%, 98%, 99% or 100% identical to the VH of SEQ ID NOs: 58, 59, 60, 61, 62, 63 or 64 and the VL that is at least 90%, 90%, 92%, 93%, 94%, 95%, 96%, 97%, 98%, 99% or 100% identical to the VL of SEQ ID NOs: 65, 66, 67, 68, 69, 70, 71, 72 or 73, wherein the antibody exhibits one or more of the following properties:

an immune complex of the antibody and shCD154 does not activate platelets, wherein platelet activation is measured by P-selectin surface expression on platelets;

binds to CD154 with a dissociation constant ($K_D$) of about $5 \times 10^{-9}$ M or less, when the $K_D$ is measured using ProteOn™ XPR36 system using experimental design described in Example 1, affinity measurements;

inhibits CD154-mediated human B cell proliferation with an $IC_{50}$ value of about $2.7 \times 10^{-9}$M or less; or inhibits CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1 \times 10^{-8}$ M or less.

In some embodiments, the antibody of the invention comprises the VH that is at least 90%, 91%, 92%, 93%, 94%, 95%, 96%, 97%, 98%, 99% or 100% identical to the VH of SEQ ID NOs: 58.

In some embodiments, the antibody of the invention comprises the VH that is at least 90%, 91%, 92%, 93%, 94%, 95%, 96%, 97%, 98%, 99% or 100% identical to the VH of SEQ ID NOs: 59.

In some embodiments, the antibody of the invention comprises the VH that is at least 90%, 91%, 92%, 93%, 94%, 95%, 96%, 97%, 98%, 99% or 100% identical to the VH of SEQ ID NOs: 60.

In some embodiments, the antibody of the invention comprises the VH that is at least 90%, 91%, 92%, 93%, 94%, 95%, 96%, 97%, 98%, 99% or 100% identical to the VH of SEQ ID NOs: 61.

In some embodiments, the antibody of the invention comprises the VH that is at least 90%, 91%, 92%, 93%, 94%, 95%, 96%, 97%, 98%, 99% or 100% identical to the VH of SEQ ID NOs: 62.

In some embodiments, the antibody of the invention comprises the VH that is at least 90%, 91%, 92%, 93%, 94%, 95%, 96%, 97%, 98%, 99% or 100% identical to the VH of SEQ ID NOs: 63.

In some embodiments, the antibody of the invention comprises the VH that is at least 90%, 91%, 92%, 93%, 94%, 95%, 96%, 97%, 98%, 99% or 100% identical to the VH of SEQ ID NOs: 64.

In some embodiments, the antibody of the invention comprises the VL that is at least 90%, 91%, 92%, 93%, 94%, 95%, 96%, 97%, 98%, 99% or 100% identical to the VL of SEQ ID NOs: 65.

In some embodiments, the antibody of the invention comprises the VL that is at least 90%, 91%, 92%, 93%, 94%, 95%, 96%, 97%, 98%, 99% or 100% identical to the VL of SEQ ID NOs: 66.

In some embodiments, the antibody of the invention comprises the VL that is at least 90%, 91%, 92%, 93%, 94%, 95%, 96%, 97%, 98%, 99% or 100% identical to the VL of SEQ ID NOs: 67.

In some embodiments, the antibody of the invention comprises the VL that is at least 90%, 91%, 92%, 93%, 94%, 95%, 96%, 97%, 98%, 99% or 100% identical to the VL of SEQ ID NOs: 68.

In some embodiments, the antibody of the invention comprises the VL that is at least 90%, 91%, 92%, 93%, 94%, 95%, 96%, 97%, 98%, 99% or 100% identical to the VL of SEQ ID NOs: 69.

In some embodiments, the antibody of the invention comprises the VL that is at least 90%, 91%, 92%, 93%, 94%, 95%, 96%, 97%, 98%, 99% or 100% identical to the VL of SEQ ID NOs: 70.

In some embodiments, the antibody of the invention comprises the VL that is at least 90%, 91%, 92%, 93%, 94%, 95%, 96%, 97%, 98%, 99% or 100% identical to the VL of SEQ ID NOs: 71.

In some embodiments, the antibody of the invention comprises the VL that is at least 90%, 91%, 92%, 93%, 94%, 95%, 96%, 97%, 98%, 99% or 100% identical to the VL of SEQ ID NOs: 72.

In some embodiments, the antibody of the invention comprises the VL that is at least 90%, 91%, 92%, 93%, 94%, 95%, 96%, 97%, 98%, 99% or 100% identical to the VL of SEQ ID NOs: 73.

In some embodiments, the antibody the invention comprises the VH of SEQ ID NO: 58 and the VL or SEQ ID NO: 65, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 59 and the VL or SEQ ID NO: 66, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 60 and the VL or SEQ ID NO: 67, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 61 and the VL or SEQ ID NO: 68, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 62 and the VL or SEQ ID NO: 69, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 63 and the VL or SEQ ID NO: 70, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 64 and the VL or SEQ ID NO: 71, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 59 and the VL or SEQ ID NO: 72, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the VH of SEQ ID NO: 59 and the VL or SEQ ID NO: 73, wherein the VH, the VL or both the VH and the VL optionally comprise one, two, three, four, five, six, seven, eight, nine, ten, eleven, twelve, thirteen, fourteen or fifteen amino acid substitutions.

In some embodiments, the antibody of the invention comprises the HCDR1, the HCDR2, the HCDR3, the LCDR1, the LCDR2 and the LCDR3 amino acid sequences, shown in Table 8, Table 9 and Table 14, or conservative modifications thereof, and wherein the antibodies retain the desired functional properties of the antagonistic antibodies specifically binding CD154.

In some embodiments, the antibody of the invention comprises the HCDR1, the HCDR2 and the HCDR3 of SEQ ID NOs: 16, 22 and 29, respectively, and conservative modifications thereof.

In some embodiments, the antibody of the invention comprises the HCDR1, the HCDR2 and the HCDR3 of SEQ ID NOs: 17, 23 and 30, respectively, and conservative modifications thereof.

In some embodiments, the antibody of the invention comprises the HCDR1, the HCDR2 and the HCDR3 of SEQ ID NOs: 16, 24 and 31, respectively, and conservative modifications thereof.

In some embodiments, the antibody of the invention comprises the HCDR1, the HCDR2 and the HCDR3 of SEQ ID NOs: 18, 25 and 32, respectively, and conservative modifications thereof In some embodiments, the antibody of the invention comprises the HCDR1, the HCDR2 and the HCDR3 of SEQ ID NOs: 19, 26 and 33, respectively, and conservative modifications thereof.

In some embodiments, the antibody of the invention comprises the HCDR1, the HCDR2 and the HCDR3 of SEQ ID NOs: 20, 27 and 34, respectively, and conservative modifications thereof.

In some embodiments, the antibody of the invention comprises the HCDR1, the HCDR2 and the HCDR3 of EQ ID NOs: 21, 28 and 35, respectively, and conservative modifications thereof.

In some embodiments, the antibody of the invention comprises the LCDR1, the LCDR2, and the LCDR3 of SEQ ID NOs: 36, 43 and 51, respectively, and conservative modifications thereof.

In some embodiments, the antibody of the invention comprises the LCDR1, the LCDR2, and the LCDR3 SEQ ID NOs: 37, 44 and 52, respectively, and conservative modifications thereof.

In some embodiments, the antibody of the invention comprises the LCDR1, the LCDR2, and the LCDR3 SEQ ID NOs: 38, 45 and 53, respectively, and conservative modifications thereof.

In some embodiments, the antibody of the invention comprises the LCDR1, the LCDR2, and the LCDR3 SEQ ID NOs: 39, 46 and 54, respectively, and conservative modifications thereof.

In some embodiments, the antibody the invention comprises the LCDR1, the LCDR2, and the LCDR3 SEQ ID NOs: 40, 47 and 55, respectively, and conservative modifications thereof.

In some embodiments, the antibody of the invention comprises the LCDR1, the LCDR2, and the LCDR3 SEQ ID NOs: 41, 47 and 56, respectively, and conservative modifications thereof.

In some embodiments, the antibody of the invention comprises the LCDR1, the LCDR2, and the LCDR3 SEQ ID NOs: 42, 48 and 57, respectively, and conservative modifications thereof.

In some embodiments, the antibody of the invention comprises the LCDR1, the LCDR2, and the LCDR3 SEQ ID NOs: 37, 49 and 52, respectively, and conservative modifications thereof.

In some embodiments, the antibody of the invention comprises the LCDR1, the LCDR2, and the LCDR3 SEQ ID NOs: 37, 50 and 52, respectively, and conservative modifications thereof.

The antibodies of the invention comprising certain HCDR1, HCDR2, HCDR3, LCDR1, LCDR2 and LCDR3 sequences and conservative modifications thereof exhibit one or more of the following properties:

an immune complex of the antibody and shCD154 does not activate platelets, wherein platelet activation is measured by P-selectin surface expression on platelets;

bind to CD154 with a dissociation constant ($K_D$) of about $5\times10^{-9}$ M or less, when the $K_D$ is measured using ProteOn™ XPR36 system using experimental design described in Example 1, affinity measurements;

inhibit CD154-mediated human B cell proliferation with an $IC_{50}$ value of about $2.7\times10^{-9}$M or less; or inhibit CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1\times10'$ M or less.

"Conservative modification" refers to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., Acta Physiol. Scand. Suppl. 643:55-67, 1998; Sasaki et al., Adv. Biophys. 35:1-24, 1998). Amino acid substitutions to the antibodies of the invention may be made by well-known methods for example by PCR mutagenesis (U.S. Pat. No. 4,683,195). Alternatively, libraries of variants may be generated using known methods, for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

Although the embodiments illustrated in the Examples comprise pairs of variable regions, one from a heavy chain and one from a light chain, a skilled artisan will recognize that alternative embodiments may comprise single heavy or light chain variable regions. The single variable region may be used to screen for variable domains capable of forming a two-domain specific antigen-binding fragment capable of for example specifically binding to CD154. The screening may be accomplished by phage display screening methods using for example hierarchical dual combinatorial approach disclosed in Int. Pat. Publ. No. WO1992/01047 as described herein.

Antibodies of the invention may be generated using various technologies. For example, the hybridoma method of Kohler and Milstein, Nature 256:495, 1975 may be used to generate monoclonal antibodies. In the hybridoma method, a mouse or other host animal, such as a hamster, rat or monkey, is immunized with human, marmoset or cyno CD154 or fragments of CD154, such as soluble form of CD154, followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals may be used to produce the antibodies of the invention. For example, Balb/c mice may be used to generate antibodies. The antibodies made in Balb/c mice and other non-human animals may be humanized using various technologies to generate more human-like sequences. Exemplary humanization techniques including selection of human acceptor frameworks are known and include CDR grafting (U.S. Pat. No. 5,225,539), SDR grafting (U.S. Pat. No. 6,818,749), Resurfacing (Padlan, Mol Immunol 28:489-499, 1991), Specificity Determining Residues Resurfacing (U.S. Pat. Publ. No. 20100261620), human-adaptation (or human framework adaptation) (U.S. Pat. Publ. No. US2009/0118127), Superhumanization (U.S. Pat. No. 7,709,226) and guided selection (Osbourn et al (2005) Methods 36:61-68, 2005; U.S. Pat. No. 5,565,332). In these methods, CDRs of parental antibodies are transferred onto human frameworks that may be selected based on their overall homology to the parental frameworks, based on framework CDR length, homology or canonical structure information, or a combination thereof.

Humanized antibodies may be further optimized to improve their selectivity or affinity to a desired antigen by incorporating altered framework support residues to preserve binding affinity (backmutations) by techniques such as those disclosed as described in Int. Pat. Publ. No. WO90/007861 and in Int. Pat. Publ. No. WO92/22653, or by introducing variation to any of the CDRs to improve for example affinity of the antibody.

Transgenic mice carrying human immunoglobulin (Ig) loci in their genome may be used to generate human antibodies against a target protein, and are described in for example Int. Pat. Publ. No. WO90/04036, U.S. Pat. No. 6,150,584, Int. Pat. Publ. No. WO99/45962, Int. Pat. Publ. No. WO02/066630, Int. Pat. Publ. No. WO02/43478, Lonberg et al (1994) Nature 368:856-9; Green et al (1994) Nature Genet. 7:13-21; Green & Jakobovits (1998) Exp. Med. 188:483-95; Lonberg and Huszar (1995) Int. Rev. Immunol. 13:65-93; Bruggemann et al (1991) Eur. J Immunol. 21:1323-1326; Fishwild et al (1996) Nat. Biotechnol. 14:845-851; Mendez et al (1997) Nat. Genet. 15:146-156; Green (1999) Immunol. Methods 231:11-23; Yang et al (1999) Cancer Res. 59:1236-1243; Brüggemann and Taussig (1997) Curr. Opin. Biotechnol. 8:455-458; Int. Pat. Publ. No. WO02/043478). The endogenous immunoglobulin loci in such mice may be disrupted or deleted, and at least one complete or partial human immunoglobulin locus may be inserted into the mouse genome using homologous or non-homologous recombination, using transchromosomes, or using minigenes. Companies such as Regeneron (www_regeneron_com), Harbour Antibodies (www_harbourantibodies_com), Open Monoclonal Technology, Inc. (OMT) (www_omtinc_net), KyMab (www_kymab_com), Trianni (www.trianni_com) and Ablexis (www_ablexis_com) may be engaged to provide human antibodies directed against a selected antigen using technology as described above.

Human antibodies may be selected from a phage display library, where the phage is engineered to express human immunoglobulins or portions thereof such as Fabs, single chain antibodies (scFv), or unpaired or paired antibody variable regions (Knappik et al., J. Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). The antibodies of the invention may be isolated for example from phage display library expressing antibody heavy and light chain variable regions as fusion proteins with bacteriophage pIX coat protein as described in Shi et al., J Mol Biol 397:385-96, 2010 and Int. Pat. Publ. No. WO09/085462). The libraries may be screened for phage binding to human, marmoset and/or cyno CD154 and the obtained positive clones may be further characterized, the Fabs isolated from the clone lysates, and expressed as full length IgGs. Such phage display methods for isolating human antibodies are described in for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

The antibodies of the invention may be human or humanized.

In some embodiments, the antibody of the invention comprises a VH framework derived from human germline gene VH1_1-69, VH4_4-39, VH1_1-02 or VH4_4-59.

In some embodiments, the antibody of the invention comprises a VL framework derived from human germline gene VKIV_B3, VKI_O12 or VL3_3R.

The antibodies of the invention may be of IgA, IgD, IgE, IgG or IgM type. The antibodies of the invention may be of IgG1, IgG2, IgG3, IgG4 type.

The antibodies of the invention may further be engineered to generate modified antibody with similar or altered properties when compared to the parental antibody. The VH, the VL, the VH and the VL, the constant regions, VH framework, VL framework, or any or all of the six CDRs may be engineered in the antibodies of the invention.

The antibodies of the invention may be engineered by CDR grafting. One or more CDR sequences of the antibodies of the invention may be grafted to a different framework sequence. CDR grafting may be done using methods described herein. In some embodiments, the antibodies of the invention comprise a VH that comprises the HDCR1 of SEQ ID NOs: 16, 17, 18, 19, 20 or 21, the HCDR2 of SEQ ID NOs: 22, 23, 24, 25, 26, 27 or 28, the HCDR3 of SEQ ID NOs: 29, 30, 31, 32, 33, 34 or 35 and the VL that comprises the LCDR1 of SEQ ID NOs: 36, 37, 38, 39, 40, 41 or 42, the LCDR2 of SEQ ID NOs: 43, 44, 45, 6, 47, 48, 49 or 50 and/or the LCDR3 of SEQ ID NOs: 51, 52, 53, 54, 55, 56 or 57, wherein the VH framework is not derived from VH1_1-69, VH4_4-39, VH1_1-02 or VH4_4-59, and the VL framework is not derived from VKIV_B3, VKI_O12 or VL3_3R. The framework sequences to be used may be obtained from public DNA databases or published references that include germline antibody gene sequences. For example, germline DNA and the encoded protein sequences for human heavy and light chain variable region genes can be found at IMGT®, the international ImMunoGeneTics information System® www-imgt_org. Framework sequences that may be used to replace the existing framework sequences in the antibodies of the invention are those that show the highest percent identity to C4LB5, C4LB89, C4LB94, C4LB150, C4LB189, C4LB191, C4LB199, C4LB231, C4LB232, C4LB35 and C4LB256.

The framework sequences of the parental and engineered antibodies may further be modified, for example by back-mutations to restore and/or improve binding of the resulting antibody to the antigen as described for example in U.S. Pat. No. 6,180,370. The framework sequences of the parental and engineered antibodies may further be modified by mutating one or more residues within the framework region, or even within one or more CDR regions, to remove T-cell epitopes to thereby reduce the potential immunogenicity of the antibody. This approach is also referred to as "deimmunization" and described in further detail in U.S. Pat. Publ. No. 20030153043.

The CDR residues of the antibodies of the invention may be mutated to improve one or more binding properties of the antibody of interest. Site-directed mutagenesis or PCR-mediated mutagenesis may be performed to introduce the mutation(s) and the effect on antibody binding, or other functional property of interest, may be evaluated in in vitro or in vivo assays as described herein and provided in the Examples. Exemplary substitutions that may be introduced are conservative modifications as discussed supra. Moreover, typically no more than one, two, three, four or five residues within a CDR region are altered.

Fc substitutions may be made to the antibody of the invention to modulate antibody half-life. For example, one or more of the substitutions M252Y, S254T and T256E may be introduced to increase the half-life of the resulting antibody (Dall'Acqua et al., J Biol Chem 281:23514-240, 2006).

Additionally, antibodies of the invention may be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention may be conjugated to polyethylene glycol (PEGylated) to improve their pharmacokinetic profiles. Conjugation may be carried out by techniques known to those skilled in the art. Conjugation of therapeutic antibodies with PEG has been shown to enhance pharmacodynamics while not interfering with function (Knigh et al., Platelets 15:409-18, 2004; Leong et al., Cytokine 16:106-19, 2001; Yang et al., Protein Eng. 16:761-70, 2003).

Antibodies or fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., *J Mol Biol* 305:989-1010, 2001). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al., Biopharm 13:36-46, 2000). A number of studies have found correlation between the ranking of the physical stability of formulations measured as thermal stability by DSC and physical stability measured by other methods (Gupta et al., AAPS PharmSci 5E8, 2003; Zhang et al., J Pharm Sci 93:3076-89, 2004; Maa et al., Int J Pharm 140:155-68, 1996; Bedu-Addo et al., *Pharm Res* 21:1353-61, 2004; Remmele et al., Pharm Res 15:200-8, 1997). Formulation studies suggest that a Fab $T_m$ has implication for long-term physical stability of a corresponding mAb.

In some embodiments, the antibody of the invention is a bispecific antibody.

In some embodiments, the antibody of the invention is a multispecific antibody.

The monospecific antibodies specifically binding CD154 of the invention may be engineered into bispecific antibodies which are also encompassed within the scope of the invention. The VL and/or the VH regions of the antibodies of the invention may be engineered using published methods into single chain bispecific antibodies as structures such as TandAb® designs (Int. Pat. Publ. No. WO1999/57150; U.S. Pat. Publ. No. 2011/0206672) or into bispecific scFVs as structures such as those disclosed in U.S. Pat. No. 5,869,620; Int. Pat. Publ. No. WO1995/15388, lnt. Pat. Publ. No. WO1997/14719 or Int. Pat. Publ. No. WO2011/036460.

The VL and/or the VH regions of the antibodies of the invention may be engineered into bispecific full length antibodies, where each antibody arm binds a distinct antigen or epitope. Such bispecific antibodies may be made by modulating the CH3 interactions between the two antibody heavy chains to form bispecific antibodies using technologies such as those described in U.S. Pat. No. 7,695,936; Int. Pat. Publ. No. WO2004/111233; U.S. Pat. Publ. No. 2010/0015133; U.S. Pat. Publ. No. 2007/0287170; Int. Pat. Publ. No. WO2008/119353; U.S. Pat. Publ. No. 2009/0182127; U.S. Pat. Publ. No. 2010/0286374; U.S. Pat. Publ. No. 2011/0123532; Int. Pat. Publ. No. WO2011/131746; Int. Pat. Publ. No. WO2011/143545; or U.S. Pat. Publ. No. 2012/0149876.

For example, bispecific antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L. Additional bispecific structures into which the VL and/or the VH regions of the antibodies of the invention may be incorporated are for example Dual Variable Domain Immunoglobulins (DVD) (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441). DVDs are full length antibodies comprising the heavy chain having a structure VH1-linker-VH2-CH and the light chain having the structure VL1-linker-VL2-CL; linker being optional.

The invention also provides for an antagonistic antibody that specifically binds CD154 of SEQ ID NO: 1 having certain VH and VL sequences, wherein the antibody VH is encoded by a first polynucleotide and the antibody VL is encoded by a second synthetic polynucleotide. The polynucleotide may be a complementary deoxynucleic acid (cDNA), and may be codon optimized for expression in suitable host. Codon optimization is a well-known technology.

In some embodiments, the polynucleotides encoding the antibody VH or VL of the invention comprise the sequences of SEQ ID NOs: 76, 77, 78 or 79.

(encoding VH of C4LB231)

SEQ ID NO: 76

GACATCCAGATGACCCAGAGCCCCAGCAGCCTGAGCGCCAGCGTGGGCG

ACAGAGTGACCATCACCTGTCGGGCCAGCCAGAGCATCAGCAGCTACCT

GAACTGGTATCAGCAGAAGCCCGGCAAGGCCCCCAAGCTGCTGATCTAC

TACGCCAACAGCCTGCAGAGCGGCGTGCCCAGCAGATTCAGCGGCAGCG

GCTCCGGCACCGACTTCACCCTGACCATCAGCAGCCTGCAGCCCGAGGA

CTTCGCCACCTACTACTGCCAGCAGAGCGACAGCATCCCCTGGACCTTC

GGCCAGGGCACCAAGGTGGAAATCAAG (encoding VL of C4LB231)

SEQ ID NO: 77

CAGGTCCAGCTGGTGCAGTCTGGCGCCGAAGTGAAGAAACCCGGCAGCA

GCGTGAAGGTGTCCTGCAAGGCCAGCGGCGGCACCTTCAGCAGCTACGG

CATCAGCTGGGTCCGACAGGCCCCAGGACAGGGCCTGGAATGGATGGGC

TGGATCAGCCCCATCTTCGGCAACACCAACTACGCCCAGAAATTCCAGG

GCAGAGTGACCATCACCGCCGACGAGAGCACCAGCACCGCCTACATGGA

ACTGAGCAGCCTGCGGAGCGAGGACACCGCCGTGTACTACTGCGCCAGA

AGCCGGTACTACGGCGACCTGGACTACTGGGGCCAGGGCACCCTGGTCA

CCGTGTCCTCT (encoding VH of C4LB191)

SEQ ID NO: 78

CAGGTGCAGCTGGTGCAGAGCGGCGCTCAGGTGCAGCTGGTGCAGTCTG

GCGCCGAAGTGAAGAAACCTGGCGCCAGCATGAAGGTGTCCTGCAAGGC

CAGCGGCTACACCTTCACCGACTACTACATCCACTGGGTGCGCCAGGCC

CCAGGCCAGGGACTGGAATGGGTGGGACGGTTCAACCCCAACAGCGGCG

ACACCAACGGCGCCCAGAAATTCCAGGGCAGAGTGACCATGACCCGGGA

CACCAGCATCAGCACCGCCTACATGGAACTGACCCGGCTGCGGAGCGAC

GACACCGCCGTGTACCACTGTGCCAGAGAGGGCGAGCTGGCCGGCATCT

TCTTCGACTACTGGGGCCAGGGCACCCTGGTGACAGTGTCCAGC (encoding VL of C4LB191)

SEQ ID NO: 79

AGCTACGAGCTGACCCAGCCCCCCAGCGTGTCCGTGTCTCCTGGCCAGA

CCGCCAGCATCACCTGTAGCGGCGACAAGCTGGGCGACAAATACGTGTC

CTGGAACCACCAGAAGCCCGGCCAGAGCCCCGTGCTGGTGATCTACCAG

GACCGGAAGAGGCCCAGCGGCATCCCCGAGAGATTCAGCGGCAGCAACA

GCGGCAACACCGCCACCCTGACCATCAGCGGCACCCAGGCCATGGACGA

GGCCGACTACTACTGCCAGGCCTGGGACAGCAGCACCGTGGTGTTCGGC

GGAGGCACCAAGCTGACCGTGCTG

The invention also provides for an isolated polynucleotide encoding any of the antibody heavy chain variable regions, the antibody light chain variable regions, the antibody heavy chains and/or the antibody light chains of the invention. Certain exemplary polynucleotides are disclosed herein, however, other polynucleotides which, given the degeneracy of the genetic code or codon preferences in a given expression system, encode the antibodies of the invention are also within the scope of the invention. Exemplary polynucleotides are for example polynucleotides having the sequences shown in SEQ ID NOs: 76, 77, 78 AND 79. The polynucleotide sequences encoding the VH or the VL or a fragment thereof of the antibody of the invention may be operably linked to one or more regulatory elements, such as a promoter or enhancer, that allow expression of the nucleotide sequence in the intended host cell. The polynucleotide may be a cDNA.

The invention also provides for a vector comprising the polynucleotide of the invention. Such vectors may be plasmid vectors, viral vectors, vectors for baculovirus expression, transposon based vectors or any other vector suitable for introduction of the synthetic polynucleotide of the invention into a given organism or genetic background by any means. For example, polynucleotides encoding light and/or heavy chain variable regions of the antibodies of the invention, optionally linked to constant regions, are inserted into expression vectors. The light and/or heavy chains may be cloned in the same or different expression vectors. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a eukaryotic cell, exemplary promoters include light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Selection of the appropriate vector and promoter is well within the level of ordinary skill in the art.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

The invention also provides for a host cell comprising one or more vectors of the invention. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells.

*Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC®), Manassas, Va., CRL-1581), NSO (European Collection of Cell Cultures (ECACC), Salisbury, Wiltshire, UK, ECACC No. 85110503), FO (ATCC® CRL-1646) and Ag653 (ATCC® CRL1580™) murine cell lines. An exemplary human myeloma cell line is U266 (ATTC® CRL-TIB-196m). Other useful cell lines include those derived from Chinese Hamster Ovary (CHO) cells such as CHO-K1SV (Lonza Biologics, Walkersville, Md.), CHO-K1 (ATCC® CRL-61™) or DG44.

The invention also provides for a method of producing an antibody of the invention comprising culturing the host cell of the invention in conditions that the antibody is expressed, and recovering the antibody produced by the host cell. Methods of making antibodies and purifying them are well known in the art. Once synthesized (either chemically or recombinantly), the whole antibodies, their dimers, individual light and/or heavy chains, or other antibody fragments such as VH and/or VL, may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody may be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules, etc. other than the subject antibody.

The invention also provides for a method for producing an antagonistic antibody specifically binding CD154 of SEQ ID NO: 1, comprising:

incorporating the first polynucleotide encoding the VH of the antibody and the second polynucleotide encoding the VL of the antibody into an expression vector;

transforming a host cell with the expression vector;

culturing the host cell in culture medium under conditions wherein the VL and the VH are expressed and form the antibody; and recovering the antibody from the host cell or culture medium.

The polynucleotides encoding certain VH or VL sequences of the invention may be incorporated into vectors using standard molecular biology methods. Host cell transformation, culture, antibody expression and purification are done using well known methods.

Methods of Treatment

Antagonistic antibodies specifically binding CD154 of the invention, for example antibodies C4LB5, C4LB89, C4LB94, C4LB150, C4LB189, C4LB191, C4LB199, C4LB231, C4LB232, C4LB35 and C4LB236, may be used for the treatment and/or prevention of any condition or disease wherein antagonizing the effects of CD154 may be therapeutically effective and may reduce the symptoms of the disease. Examples thereof include the treatment of allergic, autoimmune, cancer, transplant, GVHD, inflammatory and other conditions, especially conditions wherein the induction of tolerance and/or the suppression of humoral immunity are therapeutically desirable. Diseases that may be treated with the antibodies of the invention are immune-mediated inflammatory diseases or autoimmune diseases such as arthritis, systemic lupus erythematosus (SLE), inflammatory bowel disease, transplantation, kidney transplantation, skin transplantation, bone marrow transplantation, graft versus host disease (GVHD), immune thrombocytopenia (ITP), multiple sclerosis, thyroiditis, type I diabetes or atherosclerosis.

Beyond simply blocking CD154-CD40 interactions, anti-CD154 therapy leads to the induction of immunologic tolerance (Gordon et al., Diabetes 47: 1199-1206, 1988); Markees et al., Transplantation 64: 329-335, 1997; Jarvinen et al., Transplantation 76: 1375-1379, 2003; Quezada et al., Blood 102: 1920-1926, 2003; Frleta et al., J Immunother 26: 72-84, 2003; Elster et al., Transplantation 72: 1473-1478, 2001; Benda et al., Cell Transplantation 11: 715-720, 2002; Wekerle and Sykes, Annual review of medicine 2001. 52: 353-370[19]; Camirand et al., Transplantation 73: 453-461, 2002).

The invention also provides for a method of treating an immune-mediated inflammatory disease or an autoimmune disease, comprising administering a therapeutically effective amount of the antibody of the invention to a subject in need thereof for a time sufficient to treat the immune-mediated inflammatory disease or autoimmune disease.

The invention also provides for a method of treating arthritis, comprising administering a therapeutically effective amount of the antibody of the invention to a subject in need thereof for a time sufficient to treat arthritis.

In some embodiments, arthritis is juvenile arthritis, rheumatoid arthritis, psoriatic arthritis, Reiter's syndrome, ankylosing spondylitis, or gouty arthritis.

The invention also provides for a method of treating lupus, comprising administering a therapeutically effective amount of the antibody of the invention to a subject in need thereof for a time sufficient to treat lupus.

In some embodiments, lupus is systemic lupus erythematosus (SLE) or cutaneous lupus erythematosus (CLE).

In some embodiments, the subject has lupus nephritis.

The invention also provides for a method of treating inflammatory bowel disease, comprising administering a therapeutically effective amount of the antibody of the invention to a subject in need thereof for a time sufficient to treat inflammatory bowel disease.

In some embodiments, inflammatory bowel disease is Crohn's disease.

In some embodiments, inflammatory bowel disease is ulcerative colitis.

"Treatment" or "treat" refers to therapeutic treatment. Individuals in need of treatment include those subjects diagnosed with the disorder or a symptom of the disorder. Subjects that may be treated also include those prone to or susceptible to have the disorder, of those in which the disorder is to be prevented. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. Beneficial clinical result include, in a subject who has received treatment, for example reduced proliferation of B cells or dendritic cells, reduction of inflammatory cytokines, adhesion molecules, proteases, immunoglobulins (in instances where the CD40 bearing cell is a B cell), combinations thereof, increased production of anti-inflammatory proteins, a reduction in the number of autoreactive cells, an increase in immune tolerance, inhibition of autoreactive cell survival, and/or a decrease in one or more symptoms mediated by stimulation of CD40-expressing cells by CD154.

Clinical response may be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

Exemplary antibodies that may be used in the methods of the invention comprise the VH, the VL, the HCDR and/or the LCDR regions as shown in Table 2, Table 3, Table 4, Table 5, Table 6, table 7, Table 8, Table 9, Table 13 and Table 14, and antibodies C4LB5, C4LB89, C4LB94, C4LB150, C4LB189, C4LB191, C4LB199, C4LB231, C4LB232, C4LB35 and C4LB236.

The methods of the invention may be used to treat a subject belonging to any animal classification. Examples of subjects that may be treated include mammals such as humans, rodents, dogs, cats and farm animals.

The antibodies of the invention may be useful in the preparation of a medicament for such treatment, wherein the medicament is prepared for administration in dosages defined herein.

The antibodies of the invention may be administered in combination a second therapeutic agent.

The second therapeutic agent may be any known therapy for autoimmune and inflammatory diseases, including any agent or combination of agents that are known to be useful, or which have been used or are currently in use, for treatment of autoimmune and inflammatory diseases. Such therapies and therapeutic agents include surgery or surgical procedures (e.g. splenectomy, lymphadenectomy, thyroidectomy, plasmapheresis, leukophoresis, cell, tissue, or organ transplantation, intestinal procedures, organ perfusion, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy.

The second therapeutic agent may be a corticosteroid, an antimalarial drug, an immunosuppressant, a cytotoxic drug, or a B-cell modulator.

In some embodiments, the second therapeutic agent is prednisone, prednisolone, methylprednisolone, deflazcort, hydroxychloroquine, azathioprine, methotrexate, cyclophosphamide, mycophenolate mofetil (MMF), mycophenolate sodium, cyclosporine, leflunomide, tacrolimus, RITUXAN® (rituximab), or BENLYSTA® (belimumab).

In some embodiments, the antibodies of the invention are administered in combination with a second therapeutic agent. Exemplary second therapeutic agents are corticosteroids, nonsteroidal anti-inflammatory drugs (NSAIDs), salicylates, hydroxychloroquine, sulfasalazine, cytotoxic drugs, immunosuppressive drugs immunomodulatory antibodies, methotrexate, cyclophosphamide, mizoribine, chlorambucil, cyclosporine, tacrolimus (FK506; ProGrafrM), mycophenolate mofetil, and azathioprine (6-mercaptopurine), sirolimus (rapamycin), deoxyspergualin, leflunomide and its malononitriloamide analogs; anti-CTLA4 antibodies and Ig fusions, anti-B lymphocyte stimulator antibodies (e.g., LYMPHOSTAT-BTM) and CTLA4-Ig fusions (BLyS-1g), anti-CD80 antibodies, anti-T cell antibodies such as anti-CD3 (OKT3), anti-CD4, corticosteroids such as, for example, clobetasol, halobetasol, hydrocortisone, triamcinolone, betamethasone, fluocinole, fluocinonide, prednisone, prednisolone, methylprednisolone; non-steroidal anti-inflammatory drugs (NSAIDs) such as, for example, sulfasalazine, medications containing mesalamine (known as 5-ASA agents), celecoxib, diclofenac, etodolac, fenprofen, flurbiprofen, ibuprofen, ketoprofen, meclofamate, meloxicam, nabumetone, naproxen, oxaprozin, piroxicam, rofecoxib, salicylates, sulindac, and tolmetin; phosphodiesterase-4 inhibitors, anti-TNFα antibodies REMICADE® (infliximab), SIMPONI® (golimumab) and HUMIRA® (adalimumab), thalidomide or its analogs such as lenalidomide.

The antibodies of the invention may be administered in combination with a second therapeutic agent simultaneously, sequentially or separately.

Treatment effectiveness or RA may be assessed using effectiveness as measured by clinical responses defined by the American College of Rheumatology criteria, the European League of Rheumatism criteria, or any other criteria. See for example, Felson et al. (1995) Arthritis Rheum. 38: 727-35 and van Gestel et al. (1996) Arthritis Rheum. 39: 34-40.

Administration/Pharmaceutical Compositions

The invention provides for pharmaceutical compositions of the antagonistic antibodies specifically binding CD154 of the invention and a pharmaceutically acceptable carrier. For therapeutic use, the antibodies the invention may be prepared as pharmaceutical compositions containing an effective amount of the antibody as an active ingredient in a pharmaceutically acceptable carrier. The term "carrier" refers to a diluent, adjuvant, excipient, or vehicle with which the active compound is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 5%, 10%, 15%, 20%, 25%, 30%, 35%, 40%, 45% or 50% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration of the antibodies of the invention in the methods of the invention may be any suitable route such as parenteral administration, e.g., intradermal, intramuscular, intraperitoneal, intravenous or subcutaneous, transmucosal (oral, intranasal, intravaginal, rectal) or other means appreciated by the skilled artisan, as well known in the art.

The antibodies of the invention may be administered to a subject by any suitable route, for example parentally by intravenous (i.v.) infusion or bolus injection, intramuscularly or subcutaneously or intraperitoneally. i.v. infusion may be given over for, example, 15, 30, 60, 90, 120, 180, or 240 minutes, or from 1, 2, 3, 4, 5, 6, 7, 8, 9, 10, 11 or 12 hours.

The dose given to a subject having an immune-mediated inflammatory disease or an autoimmune disease such as rheumatoid arthritis is sufficient to alleviate or at least partially arrest the disease being treated ("therapeutically effective amount") and may be sometimes 0.005 mg/kg to about 100 mg/kg, e.g. about 0.05 mg/kg to about 20 mg/kg or about 0.1 mg/kg to about 20 mg/kg, or about 1 mg to about 20 mg/kg, or about 4 mg/kg, about 8 mg/kg, about 16 mg/kg or about 24 mg/kg, or, e.g., about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat the immune-mediated inflammatory disease, such as rheumatoid arthritis, but 9, 10, 11, 12, 13, 14, 15, 16, 17, 18, 19, 20 or more doses may be given.

The administration of the antibodies of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the antibodies of the invention may be administered at 0.1 mg/kg, at 1 mg/kg, at 5 mg/kg, at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The antibodies of the invention may be provided by maintenance therapy, such as, e.g., once a week for a period of 6 months or more.

For example, the antibodies of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The antibodies of the invention may also be administered prophylactically in order to reduce the risk of developing the immune-mediated inflammatory disease or an autoimmune disease such as arthritis or rheumatoid arthritis, and/or delay the onset of the immune-mediated inflammatory disease of the autoimmune disease.

Thus, a pharmaceutical composition of the invention for intramuscular injection may be prepared to contain 1 ml sterile buffered water, and between about 1 ng to about 100 mg/kg, e.g. about 50 ng to about 30 mg/kg or more preferably, about 5 mg to about 25 mg/kg, of the antibody of the invention.

For example, a pharmaceutical composition comprising the antibodies of the invention for intravenous infusion may be made up to contain about 200 ml of sterile Ringer's solution, and about 8 mg to about 2400 mg, about 400 mg to about 1600 mg, or about 400 mg to about 800 mg of the antibodies of the invention for administration to a 80 kg patient. Methods for preparing parenterally administrable compositions are well known and are described in more detail in, for example, "Remington's Pharmaceutical Science", 15th ed., Mack Publishing Company, Easton, Pa.

The "therapeutically effective amount" of the antibodies of the invention effective in the treatment of an immune-mediated inflammatory disease or an autoimmune disease may be determined by standard research techniques. For example, in vitro assays may be employed to help identify optimal dosage ranges. Optionally, the dosage of the antibodies of the invention that may be effective in the treatment of immune-mediated inflammatory diseases or autoimmune diseases such as arthritis or rheumatoid arthritis may be determined by administering the antibodies to relevant animal models well known in the art. Selection of a particular effective dose may be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The antibodies of the invention may be tested for their efficacy and effective dosage using any of the models described herein.

The antibodies of the invention may be lyophilized for storage and reconstituted in a suitable carrier prior to use. This technique has been shown to be effective with conventional protein preparations and well known lyophilization and reconstitution techniques can be employed.

Anti-Idiotypic Antibodies

The present invention provides for an anti-idiotypic antibody binding to the antibody of the invention.

The invention also provides for an anti-idiotypic antibody specifically binding the antibody comprising the VH of SEQ ID NO: 58 and the VL or SEQ ID NO: 65.

The invention also provides for an anti-idiotypic antibody specifically binding the antibody comprising the VH of SEQ ID NO: 59 and the VL or SEQ ID NO: 66.

The invention also provides for an anti-idiotypic antibody specifically binding the antibody comprising the VH of SEQ ID NO: 60 and the VL or SEQ ID NO: 67.

The invention also provides for an anti-idiotypic antibody specifically binding the antibody comprising the VH of SEQ ID NO: 61 and the VL or SEQ ID NO: 68.

The invention also provides for an anti-idiotypic antibody specifically binding the antibody comprising the VH of SEQ ID NO: 62 and the VL or SEQ ID NO: 69.

The invention also provides for an anti-idiotypic antibody specifically binding the antibody comprising the VH of SEQ ID NO: 63 and the VL or SEQ ID NO: 70.

The invention also provides for an anti-idiotypic antibody specifically binding the antibody comprising the VH of SEQ ID NO: 64 and the VL or SEQ ID NO: 71.

The invention also provides for an anti-idiotypic antibody specifically binding the antibody comprising the VH of SEQ ID NO: 59 and the VL or SEQ ID NO: 72.

The invention also provides for an anti-idiotypic antibody specifically binding the antibody comprising the VH of SEQ ID NO: 59 and the VL or SEQ ID NO: 73.

An anti-idiotypic (Id) antibody is an antibody which recognizes the antigenic determinants (e.g. the paratope or CDRs) of the antibody. The Id antibody may be antigen-blocking or non-blocking. The antigen-blocking Id may be used to detect the free antibody in a sample (e.g. CD154 antibody of the invention described herein). The non-blocking Id may be used to detect the total antibody (free, partially bond to antigen, or fully bound to antigen) in a sample. An Id antibody may be prepared by immunizing an animal with the antibody to which an anti-Id is being prepared.

An anti-Id antibody may also be used as an immunogen to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to the antibodies specifically binding HLA-DR antibodies.

Immunoconjugates

An "immunoconjugate" refers to the antibody of the invention conjugated to one or more heterologous molecule(s).

In some embodiments, the antibody of the invention is conjugated to one or more cytotoxic agents. Exemplary such cytotoxic agents include chemotherapeutic agents or drugs, growth inhibitory agents, toxins (e.g., protein toxins, enzymatically active toxins of bacterial, fungal, plant, or animal origin, or fragments thereof), and radioactive isotopes.

In some embodiments, an immunoconjugate is an antibody-drug conjugate (ADC) in which the antibody of the invention is conjugated to one or more drugs, such as to a maytansinoid (see, e.g., U.S. Pat. Nos. 5,208,020, 5,416, 06)); an auristatin such as monomethylauristatin drug moieties DE and DF (MMAE and MMAF) (see, e.g., U.S. Pat. Nos. 5,635,483 and 5,780,588, and 7,498,298), a dolastatin, a calicheamicin or derivative thereof (see, e.g., U.S. Pat. Nos. 5,712,374, 5,714,586, 5,739, 116, 5,767,285, 5,770, 701, 5,770,710, 5,773,001, and 5,877,296; Hinman et al., (1993) Cancer Res 53:3336-3342; and Lode et al., (1998) Cancer Res 58:2925-2928); an anthracycline such as daunomycin or doxorubicin (see, e.g., Kratz et al., (2006) Current Med. Chem 13:477-523; Jeffrey et al., (2006) Bioorganic & Med Chem Letters 16:358-362; Torgov et al., (2005) Bioconj Chem 16:717-721; Nagy et al., (2000) Proc Natl Acad Sci USA 97:829-834; Dubowchik et al, Bioorg. & Med. Chem. Letters 12: 1529-1532 (2002); King et al., (2002) J Med Chem 45:4336-4343; and U.S. Pat. No. 6,630,579), methotrexate, vindesine, a taxane such as docetaxel, paclitaxel, larotaxel, tesetaxel, and ortataxel.

In some embodiments, the immunoconjugate comprises the antibody of the invention conjugated to an enzymatically active toxin or fragment thereof, such as diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes.

In some embodiments, the antibody of the invention is conjugated to a radioactive atom to form a radioconjugate. A variety of radioactive isotopes are available for the production of radioconjugates. Examples include At211, I131, I125, Y90, Re186, Re188, Sm153, Bi212, P32, Pb212 and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-I 1, fluorine-19, carbon-13, nitrogen-15, oxygen-17, gadolinium, manganese or iron.

Conjugates of the antibody of the invention and the cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HQ), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., (1987) Science 238: 1098. Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., (1992) Cancer Res 52: 127-131; U.S. Pat. No. 5,208,020) may be used.

The immunoconjugates or ADCs may be prepared with cross-linker reagents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The invention also provides for an immunoconjugate comprising the antibody specifically binding CD154 of SEQ ID NO: 1 of the invention linked to a therapeutic agent or an imaging agent.

The present invention will now be described with reference to the following specific, non-limiting examples.

Example 1. Materials and Methods

Generation of Proteins Used

As endogenous CD154 signals as a trimer, recombinant CD154 was expressed in multiple ways to obtain a functional recombinant trimer. Soluble human CD154 (shCD154; SEQ ID NO: 4), soluble *Callithrix jacchus* (common marmoset; herein referred to as marmoset) CD154 (smCD154; SEQ ID NO: 5) or soluble *Macaca fascicularis* (cynomolgous, herein referred to as cyno) CD154 (scCD154; SEQ ID NO: 6) were cloned and expressed as His6 (SEQ ID NO: 10) fusions (shCD154-his, SEQ ID NO: 7; smCD154-his, SEQ ID NO: 8; scCD154-his, SEQ ID NO: 9) or as a fusion with leucine zipper (ILZ) (SEQ ID NO: 11) (shCD154-ILZ, SEQ ID NO: 12; smCD154-ILZ, SEQ ID NO: 13; scCD154-ILZ, SEQ ID NO: 14). Cloning, expression and protein purification was done using standard methods. Both the His and ILZ fusions were predominantly trimers. smCD154 and smCD154-ILZ were biotinylated using EZ-Link™ Sulfo-NHS-LC-Biotin and Labeling Kit (Thermo, cat no 21327), the success of the biotinylation was analyzed by HABA-avidin assay (Thermo, Cat no 46610) and Octet. Cells expressing human CD40 (SEQ ID NO: 15) were used in some assays. D1.1 Jurkat cells (ATCC® CRL-10915™) endogenously expressing human CD154 were used in some assays.

Human CD154;
SEQ ID NO: 1
MIETYNQTSPRSAATGLPISMKIFMYLLTVFLITQMIGSALFAVYLHRRL

DKIEDERNLHEDFVFMKTIQRCNTGERSLSLLNCEEIKSQFEGFVKDIML

NKEETKKENSFEMQKGDQNPQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVFVNVTDPSQVSHG

TGFTSFGLLKL

Marmoset CD154;
SEQ ID NO: 2
MIETYNQPVPRSAATGPPVSMKIFMYLLTVFLITQMIGSALFAVYLHRRL

DKIEDERNLHEDFVFMKTIQRCNTGERSLSLLNCEEIKSQFEGFVKDIML

NKEEKKKENSFEMQKGDQNPQIAAHVISEASSKTTSVLQWAEKGYYTMSN

NLVTLENGKQLTVKRQGLYYIYAQVTFCSNREASSQAPFIASLCLKPPNR

FERILLRAANTHSSAKPCGQQSIHLGGIFELQPGASVFVNVTDPSQVSHG

TGFTSFGLLKL

Cynomolgus CD154;
SEQ ID NO: 3
MIETYNQPSPRSAATGLPVRMKIFMYLLTIFLITQMIGSALFAVYLHRRL

DKIEDERNLHEDFVFMKTIQRCNTGERSLSLLNCEEIKSQFEGFVKDIML

NKEEKKKENSFEMQKGDQNPQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVFVNVTDPSQVSHG

TGFTSFGLLKL shCD154;
SEQ ID NO: 4
MQKGDQNPQIAAHVISEASSKTTSVLQWAEKGYYTMSNNLVTLENGKQLT

VKRQGLYYIYAQVTFCSNREASSQAPFIASLCLKSPGRFERILLRAANTH

SSAKPCGQQSIHLGGVFELQPGASVFVNVTDPSQVSHGTGFTSFGLLKL smCD154;
SEQ ID NO: 5
MQKGDQNPQIAAHVISEASSKTTSVLQWAEKGYYTMSNNLVTLENGKQLT

VKRQGLYYIYAQVTFCSNREASSQAPFIASLCLKPPNRFERILLRAANTH

SSAKPCGQQSIHLGGIFELQPGASVFVNVTDPSQVSHGTGFTSFGLLKL scCD154;
SEQ ID NO: 6
MQKGDQNPQIAAHVISEASSKTTSVLQWAEKGYYTMSNNLVTLENGKQLT

VKRQGLYYIYAQVTFCSNREASSQAPFIASLCLKSPGRFERILLRAANTH

SSAKPCGQQSIHLGGVFELQPGASVFVNVTDPSQVSHGTGFTSFGLLKL

```
shCD154 -his;
                                         SEQ ID NO: 7
GSHHHHHHGGGSMQKGDQNPQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVFVNVTDPSQVSHG

TGFTSFGLLKL smCD154-his;
                                         SEQ ID NO: 8
GSHHEIRREIGGGSMQKGDQNPQIAAHVISEASSKTTSVLQWAEKGYYTM

SNNLVTLENGKQLTVKRQGLYYIYAQVTFCSNREASSQAPFIASLCLKPP

NRFERILLRAANTHSSAKPCGQQSIHLGGIFELQPGASVFVNVTDPSQVS

HGTGFTSFGLLKL scCD154-his;
                                         SEQ ID NO: 9
GSHHEIRREIGGGSMQKGDQNPQIAAHVISEASSKTTSVLQWAEKGYYTM

SNNLVTLENGKQLTVKRQGLYYIYAQVTFCSNREASSQAPFIASLCLKSP

GRFERILLRAANTHSSAKPCGQQSIHLGGVFELQPGASVFVNVTDPSQVS

HGTGFTSFGLLKL

His6;
                                         SEQ ID NO: 10
HHHHHH

ILZ;
                                         SEQ ID NO: 11
RMKQIEDKIEEILSKIYHIENEIARIKKLIGER shCD154-ILZ;
                                         SEQ ID NO: 12
GSHHHHHHGGGSRMKQIEDKIEEILSKIYHIENEIARIKKLIGERGGGSM

QKGDQNPQIAAHVISEASSKTTSVLQWAEKGYYTMSNNLVTLENGKQLTV

KRQGLYYIYAQVTFCSNREASSQAPFIASLCLKSPGRFERILLRAANTHS

SAKPCGQQSIHLGGVFELQPGASVFVNVTDPSQVSHGTGFTSFGLLKL smCD154-ILZ;
                                         SEQ ID NO: 13
GSHHHHHHGGGSRMKQIEDKIEEILSKIYHIENEIARIKKLIGERGGGSM

QKGDQNPQIAAHVISEASSKTTSVLQWAEKGYYTMSNNLVTLENGKQLTV

KRQGLYYIYAQVTFCSNREASSQAPFIASLCLKPPNRFERILLRAANTHS

SAKPCGQQSIHLGGIFELQPGASVFVNVTDPSQVSHGTGFTSFGLLKL scCD154-ILZ;
                                         SEQ ID NO: 14
GSHHHHHHGGGSRMKQIEDKIEEILSKIYHIENEIARIKKLIGERGGGSM

QKGDQNPQIAAHVISEASSKTTSVLQWAEKGYYTMSNNLVTLENGKQLTV

KRQGLYYIYAQVTFCSNREASSQAPFIASLCLKSPGRFERILLRAANTHS

SAKPCGQQSIHLGGVFELQPGASVFVNVTDPSQVSHGTGFTSFGLLKL human CD40;
                                         SEQ ID NO: 15
MVRLPLQCVLWGCLLTAVHPEPPTACREKQYLINSQCCSLCQPGQKLVSD

CTEFTETECLPCGESEFLDTWNRETHCHQHKYCDPNLGLRVQQKGTSETD

TICTCEEGWHCTSEACESCVLHRSCSPGFGVKQIATGVSDTICEPCPVGF

FSNVSSAFEKCHPWTSCETKDLVVQQAGTNKTDVVCGPQDRLRALVVIPI

IFGILFAILLVLVFIKKVAKKPTNKAPHPKQEPQEINFPDDLPGSNTAAP

VQETLHGCQPVTQEDGKESRISVQERQ
```

Affinity Measurements

Affinity measurements using Surface Plasmon Resonance (SPR) were performed using a ProteOn™ XPR36 system (BioRad). A biosensor surface was prepared by coupling anti-Human IgG Fc (Jackson cat #109-005-098) to the modified alginate polymer layer surface of a GLC chip (BioRad, Cat #176-5011) using the manufacturer instructions for amine-coupling chemistry. Approximately 4700 RU (response units) of test antibodies were immobilized. The kinetic experiments were performed at 25° C. in running buffer (DPBS+0.03% polysorbate P20+100 μg/ml BSA). To perform kinetic experiments, 100 RU of antibodies were captured followed by injections of analytes (shCD154-his and smCD154-his) at concentrations ranging from 0.391 nM to 100 nM (in a 4-fold serial dilution). The association phase was monitored for 3 minutes at 50 μL/min followed by 15 minutes of buffer flow (dissociation phase). The chip surface was regenerated with two 18 second pulses of 100 mM $H_3PO_4$ (Sigma, Cat #7961) at 100 μL/min.

The collected data were processed using ProteOn™ Manager software. First, the data was corrected for background using inter-spots. Then, double reference subtraction of the data was performed by using the buffer injection for analyte injections. The kinetic analysis of the data was performed using a Langmuir 1:1 binding model.

CD154-Induced Ramos Cell Activation

Ability of the anti-CD154 antibodies to inhibit Ramos cell activation was assessed using CD54 as a marker for cellular activation. Ramos cells (Burkitt's lymphoma cells, ATCC® CRL-1596™) maintained according to vendor protocol were seeded into a 96 well v-bottom plate at $2.0 \times 10^5$ cells/well in complete growth medium in 100 μl/well. The test antibodies at concentrations 0.2, 2 or 20 μg/ml were pre-incubated with 40 ng/ml smCD154-his for 1 h at room temperature (RT) and then added to the cells. The plate was covered and incubated overnight (37° C., 5% $CO_2$). On the following day the assay plate was spun down and the spent treatment medium removed. The resulting cell pellets were washed with cold PBS/2% FBS and then cells stained with PE labelled anti-CD54 (ICAM-1) antibody or appropriate isotype control for 1 h at 4° C. The cells were washed with cold PBS/2% FBS, resuspended in 100 μl/well cold PBS/2% FBS and the fluorescent signal (yellow channel) measured on a flow cytometer. Antibodies were determined to be antagonists when they met the criteria: % potency relative to 5C8 antibody >5% 5C8 potency, where % potency refers to the normalized percent inhibition relative to 5C8 at the highest concentration tested.

NF-κB-SEAP Reporter Gene Assay

Ability of the anti-CD154 antibodies to inhibit CD154-induced CD40 downstream signaling pathways were assessed using HEK-Blue™ CD40L cells (Invivogen), engineered to express human CD40 and transfected with a secreted embryonic alkaline phosphatase (SEAP) reporter gene under the control of NF-κB-inducible promoter (IFN-β minimal promoter). The cells were stimulated with either human or cyno CD154, or with Jurkat cells. HEK-Blue™ CD40L cells were maintained according to the vendor's protocol and all activity assays were performed in DMEM supplemented with 10% heat-inactivated fetal bovine serum and 1× Glutamax. The cells were seeded into 96 well tissue culture plates at a cell density of 2.5 or $5×10^4$ cells per well in 100 µl volume and incubated overnight (37° C., 5% $CO_2$). On the following day 4× solutions of shCD154-His or shCD154-ILZ, or D1.1 Jurkat cells were pre-incubated with 4× solutions of anti-CD154 antibodies (at appropriate concentrations) at a 1:1 ratio to yield 2× solutions of CD154: antibody pre-complex mixtures. The CD154:antibody mixtures were incubated at RT for 1 h, while the D1.1 Jurkat: mAb mixture was incubated at 37° C. and 5% $CO_2$ for 1 h. At the end of the pre-complex incubation period, 100 µl/well of the 2× pre-complex solutions were added to the 96 well assay plate containing HEK-Blue™ CD40L cells; the final assay volume was 200 µl/well with final CD154 concentrations of 80 ng/ml shCD154-His, or 40 ng/ml shCD154-ILZ, or $2.5-6.0×10^4$ D1.1 Jurkat cells. After 16-24 h of treatment time (37° C., 5% $CO_2$) the supernatants were analyzed for phosphatase (SEAP) activity by measuring absorbance (650 nm) of 40 µl/well of supernatants that was incubated with 160 µl/well of QUANTI-Blue™ (Invivogen) at 37° C. for 30-60.

Jurkat Cell-Mediated Dendritic Cell Activation Assay

Ability of the anti-CD154 antibodies to inhibit Jurkat-cell mediated activation of DC was evaluated by measuring reduced production of various cytokines by the DC. Human monocytes (Biologic Specialties) were cultured with 50 ng/ml IL-4 and GM-CSF for six days. The cells were replenished with fresh media (with IL-4 and GM-CSF) on day 3. The immature DCs (iDCs) ($CD1a^+$ $CD14^{low}$ $CD83^-$) were used in cell assays on day 6. $2.5×10^5$ D1.1 Jurkat cells (irradiated at 1000 rads) were incubated with 0.000064-25 µg/ml µg/ml anti-CD154 antibodies for 15-20 minutes then co-cultured with $2.5×10^4$ iDCs in a final volume of 200 µl/well in a 96-well round bottom plate. After 48 hour incubation supernatants were harvested for cytokine analysis.

Jurkat Cell-Mediated B Cell Activation Assay

Ability of the anti-CD154 antibodies to inhibit Jurkat-cell mediated B cell activation was evaluated by assessing the effect of the antibodies on B cell proliferation. $1×10^5$ D1.1 Jurkat cells (irradiated at 5000 rads) were co-cultured with $1×10^5$ human tonsil B cells in the presence of IL-21 (100 ng/ml) and 0.0077 ng/ml-15 µg/ml of anti-CD154 antibodies in a final volume of 200 µl/well in a 96-well round bottom plate. After 2 days incubation methyl (−3H)-Thymidine (0.5 µCi/well) were added to the cultures and human B cell proliferation was determined after overnight incubation.

CD154-Mediated B Cell Activation Assay

Ability of the anti-CD154 antibodies to inhibit recombinant CD154-mediated B cell activation was evaluated in human or cynomolgus B cells. $1×10^5$ human tonsil B cells or cynomolgus monkey spleen cells were cultured with 100 ng/ml rhIL-21, 0.5 µg/ml shCD154-ILZ, and 0.0077 ng/ml-15 µg/ml of anti-CD154 antibodies in a final volume of 200 µl/well in a 96-well round bottom plate. After 2 days incubation methyl (−3H)-Thymidine (0.5 µCi/well) were added to the cultures and human B cell proliferation was determined after overnight incubation.

Example 2. Isolation of Anti-CD154 Antibodies from Phage Display Libraries

CD154 binding Fabs were selected from de novo pIX phage display libraries as described in Shi et al., J Mol Biol 397:385-96, 2010; Int. Pat. Publ. No. WO2009/085462; U.S. Pat. Publ. No. US2010/0021477). Briefly, the libraries were generated by diversifying human scaffolds where germline VH genes IGHV1-69*01, IGHV3-23*01, and IGHV5-51*01 were recombined with the human IGHJ-4 minigene via the H3 loop, and human germline VLkappa genes O12 (IGKV1-39*01), L6 (IGKV3-11*01), A27 (IGKV3-20*01), and B3 (IGKV4-1*01) were recombined with the IGKJ-1 minigene to assemble complete VH and VL domains. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et al., J Mol Biol 397:385-96, 2010. The scaffolds utilized to generate libraries were named according to their human VH and VL germline gene origin. The three heavy chain libraries were combined with the four germline light chains or germline light chain libraries to generate 12 unique VH: VL combinations for panning experiments against smCD154 or cells expressing full-length cyno CD154.

The libraries were panned against either full length cyno CD154 (SEQ ID NO: 3) expressed stably in CHO-s cells or biotinylated and nonbiotinylated smCD154 (SEQ ID NO: 5). After several rounds of panning, a polyclonal phage ELISA using smCD154 as antigens was performed to detect the specific enrichment of individual panning experiments. The phage collected from those panning experiments which demonstrated enrichment for binders to smCD154were further screened with a monoclonal Fab ELISA in which Fab proteins expressed from individual Fab clones were used as binders to nonbiotinylated smCD154 directly coated on the plate. The Fab clones with binding signal four times higher than the negative control Fabs were selected to be screened in full IgG format. Select Fabs were cloned into IgG2sigma/ κappa backbone and characterized further using for binding to D1.1 Jurkat cells. IgG2sigma is a silent Fc and has substitutions V234A, G237A, P238S, H268A, V309L, A330S and P331S when compared to the wild type IgG2. IgG2sigma is described in U.S. Pat. No. 8,961,967.

Example 3. Generation of Anti-CD154 Antibodies in Rats

Anti-CD154 antibodies were generated using transgenic rats expressing human immunoglobulin loci, the OmniRat®; OMT, Inc. The OmniRat® endogenous immunoglobulin loci are replaced by human Igκ and Igλ loci and a chimeric human/rat IgH locus with V, D and J segments of human origin linked to the rat $C_H$ locus. The IgH locus contains 22 human $V_H$s, all human D and $J_H$ segments in natural configuration linked to the rat $C_H$ locus. Generation and characterization of the OmniRat® is described in Osborn, et al. J Immunol 190: 1481-1490, 2013; and Int. Pat. Publ. No. WO2014/093908.

OmniRat® was immunized with smCD154 by the repetitive immunization at multiple sites (RIMMS) protocol. Following a 45 day immunization regimen, lymph nodes were harvested from all four rats and used to generate hybridomas. Hybridoma supernatants in 96-well plates were screened via binding ELISA to identify mAbs which exhibited binding to smCD154, from which hybridoma supernatants exhibiting an assay signal greater than 3-fold the negative control average were selected.

Select antibodies were cloned as full length IgG2sigma/λ. Antibodies demonstrating antagonist activity in CD154-induced Ramos cell activation were selected for further characterization.

Example 4. Characterization of the Antibodies

Several anti-CD154 antibodies obtained from phage display or transgenic animals expressing human immunoglobulin loci which demonstrated antagonistic activity as described in Examples 2 and 3 were sequenced and further characterized for their binding to human and cyno dendritic cells, for their ability to inhibit human and cyno dendritic and B cell functions, and for antibody effector functions. The VH and the VL regions of the antibodies were sequenced using standard methods.

Table 2 shows the HCDR1 amino acid sequences of select antibodies.

Table 3 shows the HCDR2 amino acid sequences of select antibodies.

Table 4 shows the HCDR3 amino acid sequences of select antibodies.

Table 5 shows the LCDR1 amino acid sequences of select antibodies.

Table 6 shows the LCDR2 amino acid sequences of select antibodies.

Table 7 shows the LCDR3 amino acid sequences of select antibodies.

Table 8 shows the VH amino acid sequences of select antibodies.

Table 9 shows the VL amino acid sequences of select antibodies

TABLE 2

| mAb ID | HCDR1 Sequence | SEQ ID NO: |
| --- | --- | --- |
| C4LB5 | SYAIS | 16 |
| C4LB89 | SYGIS | 17 |
| C4LB94 | SYAIS | 16 |
| C4LB150 | SYSFYWG | 18 |
| C4LB189 | AYYIH | 19 |
| C4LB191 | DYYIH | 20 |
| C4LB199 | SFIYYWG | 21 |

TABLE 3

| mAb ID | HCDR2 Sequence | SEQ ID NO: |
| --- | --- | --- |
| C4LB5 | GIIPIFGTANYAQKFQG | 22 |
| C4LB89 | WISPIFGNTNYAQKFQG | 23 |
| C4LB94 | GISPYFGNTNYAQKFQG | 24 |
| C4LB150 | SLYYSGSTYYNPSLKS | 25 |

TABLE 3-continued

| mAb ID | HCDR2 Sequence | SEQ ID NO: |
| --- | --- | --- |
| C4LB189 | RINPDSGGTDYAQRFQG | 26 |
| C4LB191 | RFNPNSGDTNGAQKFQG | 27 |
| C4LB199 | CIYSSGGTYYNPSLKS | 28 |

TABLE 4

| mAb ID | HCDR3 Sequence | SEQ ID NO: |
| --- | --- | --- |
| C4LB5 | GASVWDGPAEVFDY | 29 |
| C4LB89 | SRYYGDLDY | 30 |
| C4LB94 | DTGVVVGAFYLDY | 31 |
| C4LB150 | LQLGTTTDYFDH | 32 |
| C4LB189 | DWNYYDGSGYFGPGYYGLDV | 33 |
| C4LB191 | EGELAGIFFDY | 34 |
| C4LB199 | LWLGTTTDYFDY | 35 |

TABLE 5

| mAb ID | LCDR1 Sequence | SEQ ID NO: |
| --- | --- | --- |
| C4LB5 | KSSQSVLASSNNENFLA | 36 |
| C4LB89 | RASQSISSYLN | 37 |
| C4LB94 | KSSQSVLYSSNNKNYLA | 38 |
| C4LB150 | SGDELGDKFAC | 39 |
| C4LB189 | SGDKLGDKYVC | 40 |
| C4LB191 | SGDKLGDKYVS | 41 |
| C4LB199 | SGDKLGDKFAC | 42 |

TABLE 6

| mAb ID | LCDR2 Sequence | SEQ ID NO: |
| --- | --- | --- |
| C4LB5 | SASTRES | 43 |
| C4LB89 | YANSLQS | 44 |
| C4LB94 | WASTRES | 45 |
| C4LB150 | QENKRPS | 46 |
| C4LB189 | QDRKRPS | 47 |

TABLE 6-continued

LCDR2

| mAb ID | Sequence | SEQ ID NO: |
|---|---|---|
| C4LB191 | QDRKRPS | 47 |
| C4LB199 | QDDKRPS | 48 |

TABLE 7

LCDR3

| mAb ID | Sequence | SEQ ID NO: |
|---|---|---|
| C4LB5 | QQAYTTPFT | 51 |
| C4LB89 | QQSDSIPVVT | 52 |
| C4LB94 | QQYYSTPLT | 53 |
| C4LB150 | QAWDSDTAV | 54 |
| C4LB189 | QAWDSGTVV | 55 |
| C4LB191 | QAWDSSTVV | 56 |
| C4LB199 | QAWDSNTVV | 57 |

TABLE 8

VH

| mAb ID | VH name | Sequence | SEQ ID NO: |
|---|---|---|---|
| C4LB5 | C4LH12 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGASVWDGPAEVFDYWGQGTLVTVSS | 58 |
| C4LB89 | C4LH165 | QVQLVQSGAEVKKPGSSVKVSCKASGGTFSSYGISWVRQAPGQGLEVVMGWISPIFGNTNYAQKFQGRVTITADESTSTAYMELSSLRSEDTAVYYCARSRYYGDLDYWGQGTLVTVSS | 59 |
| C4LB94 | C4LH99 | QVQLVQSGAEVKKPGSSVKVSCKASGGTFSSYAISWVRQAPGQGLEWMGGISPYFGNTNYAQKFQGRVTITADESTSTAYMELSSLRSEDTAVYYCARDTGWVGAFYLDYWGQGTLVTVSS | 60 |
| C4LB150 | C4LH201 | QLQLQESGPGLVKPSETLSLTCTVSGGSISSYSFYWGWIRQPPGQGLEWIGSLYYSGSTYYNPSLKSRATMSVVTSKTQFSLNLNSVTAADTAVYYCARLQLGTTTDYFDHWGQGTLVTVSS | 61 |
| C4LB189 | C4LH240 | QVQLVQSGAEVKKPGASVKVSCKASGYTFAAYYIHWVRQAPGQGLEVVMGRINPDSGGTDYAQRFQGRVTMTRDTSISTAYMELSRLRSDDTAVFYCARDWNYYDGSGYFGPGYYGLDVWGQGTTVTVSS | 62 |
| C4LB191 | C4LH242 | QVQLVQSGAEVKKPGASMKVSCKASGYTFTDYYIHWVRQAPGQGLEVVVGRFNPNSGDTNGAQKFQGRVTMTRDTSISTAYMELTRLRSDDTAVYHCAREGELAGIFFDYWGQGTLVTVSS | 63 |

TABLE 8-continued

VH

| mAb ID | VH name | Sequence | SEQ ID NO: |
|---|---|---|---|
| C4LB199 | C4LH250 | QVQLQESGPGLVKPSETLSLTCTVSGDSISSFIYYWGWIRQPPGKGLDVVVGCIYSSGGTYYNPSLKSRVTISVDTSKNQFSLKLPSVTAADTAVYYCARLWLGTTTDYFDYWGQGTLVTVSS | 64 |

TABLE 9

VL

| mAb ID | VL | Sequence | SEQ ID NO: |
|---|---|---|---|
| C4LB5 | C4LL8 | DIVMTQSPDSLAVSLGERATINCKSSQSVLASSNNENFLAWYQQKPGQPPKLLIYSASTRESGVPDRFSGSGSGTDFTLTISSLQAEDVAVYYCQQAYTTPFTFGQGTKVEIK | 65 |
| C4LB89 | C4LL49 | DIQMTQSPSSLSASVGDRVTITCRASQSISSYLNWYQQKPGKAPKLLIYYANSLQSGVPSRFSGSGSGTDFTLTISSLQPEDFATYYCQQSDSIPVVTFGQGTKVEIK | 66 |
| C4LB94 | PH9L2 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK | 67 |
| C4LB150 | C4LL82 | SYELTQPPSVSVSPGQTASITCSGDELGDKFACWYQQKPGQSPVLVIWQENKRPSGIPERFSGSNSGNTATLTISGTQAMDEADYYCQAWDSDTAVFGGGTKLTVL | 68 |
| C4LB189 | C4LL116 | SYELTQPPSVSVSPGQTASVTCSGDKLGDKYVCWYQRKPGQSPVLVIYQDRKRPSGIPERFSGSNSGNTATLTISGTQAIDEADYYCQAWDSGTVVFGRGTKLTVL | 69 |
| C4LB191 | IAPL39 | SYELTQPPSVSVSPGQTASITCSGDKLGDKYVSWNHQKPGQSPVLVIYQDRKRPSGIPERFSGSNSGNTATLTISGTQAMDEADYYCQAWDSSTVVFGGGTKLTVL | 70 |
| C4LB199 | C4LL125 | SYELTQPPSVSVSPGQTVSITCSGDKLGDKFACWYQQKPGQSPVVVIYQDDKRPSGIPERFSGSTSGNTATLTISGTQAMDEADYYCQAWDSNTVVFGGGTKLTVL | 71 |

The antibodies inhibited function of both endogenous CD154 provided on Jurkat cells (D1.1 Jurkat cells in Table 10) and recombinantly expressed human CD154 trimer (expressed as shCD154-ILZ or shCD154-his) as measured using the NF-κB SEAP reporter gene assay. The antibodies inhibited signaling with $IC_{50}$ values ranging from 0.08-21.15 nM. The $IC_{50}$ values for select antibodies in the assay are shown in Table 10. The range of $IC_{50}$ values in the table for each antibody represent the lowest and the highest $IC_{50}$ values obtained from separate experiments, while the singular value indicates the antibody was tested in one experiment, or only one valid $IC_{50}$ value was available.

TABLE 10

| mAb ID | NF-κB SEAP reporter gene assay; IC$_{50}$ (nM) | | |
|---|---|---|---|
| | D1.1 Jurkat* | shCD154-ILZ* | shCD154-his* |
| C4LB5 | 1.55 | 0.54 | 1.03-1.37 |
| C4LB89 | 0.08-0.32 | 1.91-2.44 | 3.93-5.69 |
| C4LB94 | 0.13 | 4.37 | 7.57-21.15 |
| C4LB150 | 3.57 | 4.95 | 8.87-9.81 |
| C4LB189 | 2.06 | 1.63 | 6.51-13.60 |
| C4LB191 | | | 2.19-3.46 |
| C4LB199 | 1.21 | 1.09 | 2.00-2.70 |

*CD154 format used to induce signaling

The ability of the antibodies to inhibit dendritic cell activation was assessed using IL-12p40 secretion as a marker for DC activation. The antibodies inhibited DC activation induced by endogenous CD154 provided on Jurkat cells with IC$_{50}$ values ranging from 0.02 to 0.49 nM. Table 11 shows the IC$_{50}$ values for select antibodies in the assay. The IC$_{50}$ range in the Table represents the lowest and the highest IC$_{50}$ value obtained in separate experiments across 2-4 donors with 1-6 repetitions.

TABLE 11

| mAb ID | Jurkat cell-mediated dendritic cell activation assay; IC$_{50}$ (nM) |
|---|---|
| C4LB5 | 0.32-0.49 |
| C4LB89 | 0.02-0.09 |
| C4LB94 | 0.07-0.09 |
| C4LB150 | 0.25-0.30 |
| C4LB189 | 0.15-0.16 |
| C4LB191 | 0.38-0.39 |
| C4LB199 | 0.19-0.20 |

The ability of the antibodies to inhibit human or cyno B cell activation was measured using B cell proliferation as readout. The antibodies inhibited both endogenous CD154 (D1.1 Jurkat cells) and recombinant human CD154 trimer (shCD154-ILZ) induced proliferation with IC$_{50}$ values ranging from 0.01-5.35 nM. Table 12 shows the IC$_{50}$ values for various antibodies obtained in human or cyno B cell activation assay. The IC$_{50}$ range in the table represents the lowest and the highest IC$_{50}$ value obtained in separate experiments across 2-4 donors with 1-6 repetitions. A singular IC$_{50}$ value in the Table indicates availability of one valid IC$_{50}$ value.

TABLE 12

| mAb ID | B cell activation assay; IC$_{50}$ (nM) | | |
|---|---|---|---|
| | D1.1 Jurkat cells/ human B cells* | shCD154-ILZ/ human B cells* | shCD154-ILZ/ cyno B cell* |
| C4LB5 | 0.19-0.28 | 2.74 | 5.35 |
| C4LB89 | 0.01-0.02 | 0.20-0.48 | 0.13-0.44 |
| C4LB94 | 0.01-0.03 | 0.07-0.14 | 0.30-0.31 |
| C4LB150 | 0.27-0.31 | nd | 1.14-2.00 |
| C4LB189 | 0.47-0.65 | nd | 4.35-5.16 |
| C4LB191 | 0.64-1.00 | nd | 0.25-0.36 |
| C4LB199 | 0.04-0.27 | nd | 1.89-2.31 | nd: not done
*CD154 format used to induce signaling/source of B cells

Example 5. Engineering of Antibodies to Minimize Post-Translational Modification Risk The VL of antibody C4LB89 contained a putative deamination site in LCDR2 (N52-S53 in the light chain C4LL49, SEQ ID NO: 66). Substitutions were individually made to each position (N52S and S53T) in the VL. The mutated light chains were co-expressed with the parental heavy chain C4LH165 (SEQ ID NO: 59) to generate antibodies C4LB235 and C4LB236 as IgG2sigma/κ. The amino acid sequences of the LCDR2 and VL of C4LB235 and C4LB236 are shown in Table 13 and Table 14, respectively. C4LB235 comprises the HCDRs of SEQ ID NOs: 17, 23 and 30, the LCDRs of SEQ ID NOs 37, 49 and 52, the VH of SEQ ID NO: 59 and the VL of SEQ ID NO: 72. C4LB236 comprises the HCDRs of SEQ ID NOs: 17, 23 and 30, the LCDRs of SEQ ID NOs 37, 50 and 52, the VH of SEQ ID NO: 59 and the VL of SEQ ID NO: 73.

TABLE 13

| | LCDR2 | |
|---|---|---|
| mAb ID | Sequence | SEQ ID NO: |
| C4LB235 | YASSLQS | 49 |
| C4LB236 | YANTLQS | 50 |

TABLE 14

| | | VL | |
|---|---|---|---|
| mAb ID | VL | Sequence | SEQ ID NO: |
| C4LB235 | C4LL160 | DIQMTQSPSSLSASVGDRVTI TCRASQSISSYLNVVYQQKPG KAPKLLIYYASSLQSGVPSRF SGSGSGTDFTLTISSLQPEDF ATYYCQQSDSIPVVTFGQGTK VEIK | 72 |
| C4LB236 | C4LL161 | DIQMTQSPSSLSASVGDRVTI TCRASQSISSYLNVVYQQKPG KAPKLLIYYANTLQSGVPSRF SGSGSGTDFTLTISSLQPEDF ATYYCQQSDSIPVVTFGQGTK VEIK | 73 |

Both antibodies were tested for their ability to inhibit cyno B cell proliferation. C4LB235 showed similar potency to C4LB89, while C4LB236 showed reduced potency compared to C4LB89.

Example 6. Effector Silent Anti-CD154 Antibodies do not Induce Platelet Activation Anti-CD154 antibodies have been developed in the clinic with positive outcomes in patients with autoimmune diseases, however, due to incidents of thromboembolism (TE) further clinical development of the antibodies were halted. Humanized 5c8 antibody (IgG1/κ) is anti-CD154 antibody which in the clinic induced TE (Yazdany et al., Lupus 13:377-380, 2004). It is hypothesized that thromboembolism (TE) mediated by humanized 5c8 is a result of platelet activation and aggregation from formation of high-ordered anti-CD154/CD154 immune complexes (IC) that cross-link platelets by binding Fc to platelet FcγRIIa receptor. In vitro, engineered 5c8 antibody with silenced Fc (D265A substitution in IgG1) lacking FcγRIIa receptor binding did not activate platelets (Xie et al., J Immunol 192:4083-4092, 2014).

Anti-CD154 antibodies with abolished binding to at least FcγRIIa and having reduced effector functions may thus be more suitable as a therapeutic with a reduced risk for TE.

To that end, effector silent anti-CD154 antibodies were generated with various Fc substitutions and tested for their effect on platelet activation.

VH and VL of the humanized 5c8 antibody (Karpusas et al., Structure 9: 321-329, 2001) were cloned as IgG1sigma/κ, IgG1sigmaYTE/κ, IgG2sigma/κ or IgG2sigmaYTE/κ to evaluate effect of the Fc on platelet activation; the resulting antibodies were named 5c8IgG1sigma, 5c8IgG1sigmaYTE, 5c8IgG2sigma and 5c8IgG2sigmaYTE). IgG1sigma contains substitutions L234A, L235A, G237A, P238S, H268A, A330S, and P331S when compared to the wild type IgG1. IgG1sigmaYTE contains L234A, L235A, G237A, P238S, M252Y, S254T, T256E H268A, A330S and P331S substitutions. IgG2sigma contains V234A, G237A, P238S, H268A, V309L, A330S and P331S substitutions. IgG2sigmaYTE contains V234A, G237A, P238S, M252Y, S254T, T256E, H268A, V309L, A330S and P331S substitutions. Residue numbering is according to the EU Index. Antibodies with IgG2sigma backbone lack effector functions and binding to FcγR as described in U.S. Pat. No. 8,961,967. YTE substitution (M252Y, S254T, T256E) is described in Dall'Acqua et al., J Biol Chem 281:23514-24, 2006.

VH and the VL domains of the humanized 5c8 are shown in SEQ ID NOs: 74 and 75, respectively.

SEQ ID NO: 74
QVQLVQSGAEVVKPGASVKLSCKASGYIFTSYYMYWVKQAPGQGLEWIGE
INPSNGDTNFNEKFKSKATLTVDKSASTAYMELSSLRSEDTAVYYCTRSD
GRNDMDSWGQGTLVTVSS

SEQ ID NO: 75
DIVLTQSPATLSVSPGERATISCRASQRVSSSTYSYMHWYQQKPGQPPKL
LIKYASNLESGVPARFSGSGSGTDFTLTISSVEPEDFATYYCQHSWEIPP
TFGGGTKLEIK

5c8IgG1sigma, 5c8IgG1sigmaYTE, 5c8IgG2sigma and 5c8IgG2sigmaYTE were tested for their effect on platelet activation.

Blood from healthy human donors, pre-screened for low response to shCD154 alone, was used. Platelet activation was evaluated by flow cytometry using validated platelet activation markers PAC-1 (activated GPIIb/IIIa) and CD62p (P-selectin). Briefly, whole blood (WB) was added to modified Tyrodes-HEPES buffer containing 1 mM $CaCl_2$), and anti-PAC1 and anti-CD62p antibodies with or without FcγRIIa blocking antibody (clone IV.3, StemCell Technologies #60012) were added to the mixture and incubated for 25 minutes. Pre-formed immune complexes of soluble CD154 (PeproTech, cat #310-02; SEQ ID NO: 4 or Tonbo Biosciences, cat #21-7088)/antibody at molar ratio of 3:1 CD154: anti-CD154 were added to the mixture and incubated for another 20 minutes; platelets were fixed in 1% formalin followed by FACS analysis. Platelet activation for each condition was assessed as % of gated platelets (CD61 positive events) expressing PAC-1 and CD62p; 5000 CD61 expressing events (platelets) were captured and analyzed for each treatment condition. Results of the experiment are shown in FIG. 1. CD154/5c8IgG1 (wild-type IgG1) IC activated platelets, while CD154 IC with 5c8-IgG1sigma, 5c8IgG1sigmaYTE, 5c8IgG2sigma and 5c8IgG2sigma-YTE did not activate platelets. Platelet activation with ADP was not inhibited by the immune complexes (data not shown). None of the antibodies alone activated platelets (data not shown).

Figure 2:
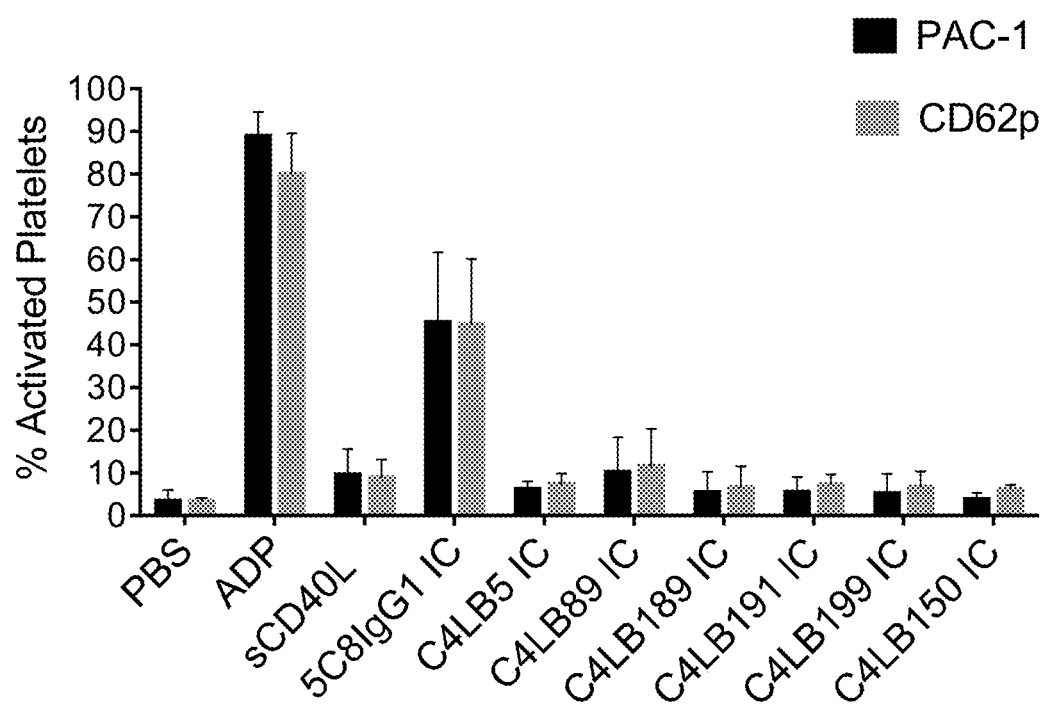
FIG. 2 shows that immune complexes (IC) of shCD154 (sCD40L in the Figure) and effector silent IgG2sigma/κ anti-CD154 antibodies C4LB5, C4LB89, C4LB189, C4LB191, C4LB199 and C4LB150 do not activate platelets. Platelet activation was assessed as % of total platelets expressing PAC-1 and CD62p. IC of shCD154 and 5c8IgG1 (5c8IgG1 IC) activated platelets. ADP: positive control. Five donors were evaluated for platelet activation. The results are shown as mean of each experiment±SD.

Anti-CD154 antibodies C4LB5, C4LB89, C4LB94, C4LB150, C4LB189, C4LB191, C4LB199 (all IgG2sigma effector silent mAbs) were also tested in platelet activation assay to confirm the antibodies had abolished binding to FcγRIIa and did not activate platelets. FIG. 2 shows the results of the experiment, demonstrating that immune complexes of CD154 in complex with C4LB5, C4LB89, C4LB150, C4LB189, C4LB191 or C4LB199 failed to activate platelets. CD154/C4LB94 IC induced PAC-1 on platelets. The results demonstrate that anti-CD154 antibodies with IgG1sigma, IgG1sigmaYTE, IgG2sigma or IgG2sigmaYTE isotypes in general may not activate platelets, and may therefore have an improved safety profile over the antibodies on wild type IgG1.

Example 7. Effect of Isotype Switching on Antibody Properties

Variable regions of antibody C4LB89 were cloned as IgG1sigma/κ and IgG1sigmaYTE isotypes to assess possible differences in functionality and developability. The new antibodies were named C4LB231 (IgG1sigma) and C4LB232 (IgG1sigmaYTE).

The resulting IgG1sigma and IgG1sigmaYTE antibodies were compared to the parental antibody in their functionality. C4LB231 and C4LB232 were comparable in function to the parental C4LB89. Table 15 shows the $IC_{50}$ values or a range of the $IC_{50}$ values for each antibody in the functional assays as indicated in the Table. The $IC_{50}$ range in the table represents the lowest and the highest $IC_{50}$ value obtained in experiments across 2-4 donors with 1-6 repetitions. A singular $IC_{50}$ value in the table indicates availability of one valid $IC_{50}$ value.

TABLE 15

| Assay | CD154 format used to induce signaling | mAb C4LB231 | mAb C4LB232 |
|---|---|---|---|
| NF-κB SEAP reporter gene assay; $IC_{50}$ (nM) | D1.1 Jurkat | | 0.27 |
| NF-κB SEAP reporter gene assay; $IC_{50}$ (nM) | shCD154-ILZ | 1.21 | 1.25-1.45 |
| NF-κB SEAP reporter gene assay; $IC_{50}$ (nM) | shCD154-his | 2.15 | 1.77-1.99 |
| Jurkat cell-mediated dendritic cell activation assay; IL-12p40 $IC_{50}$ (nM) | D1.1 Jurkat | 0.02-0.04 | 0.03-0.03 |
| human B cell proliferation $IC_{50}$ (nM) | D1.1 Jurkat | 0.01-0.01 | 0.01-0.01 |
| human B cell proliferation $IC_{50}$ (nM) | shCD154-ILZ | 0.38-0.67 | 0.42-0.74 |
| cyno B cell proliferation $IC_{50}$ (nM) | shCD154-ILZ | 0.25-0.55 | 0.20-0.55 |

Figure 3:
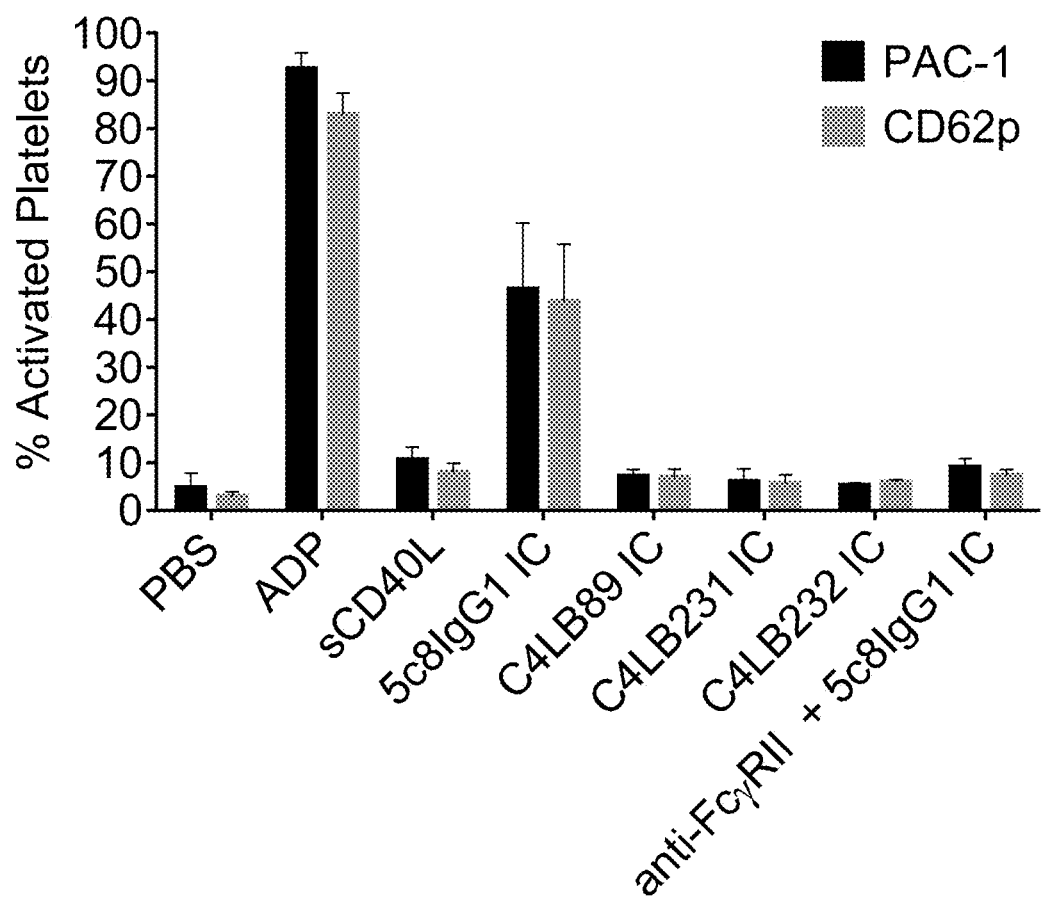
FIG. 3 shows that immune complexes (IC) of shCD154 (sCD40L) and anti-CD154 antibodies C4LB89 (IgG2sigma/κ), C4LB231 (IgG1sigma/κ) and C4LB232 (IgG1sigma/κ) do not activate platelets. Platelet activation was assessed as % of total platelets expressing PAC-1 and CD62p. 5c8-IgG1 IC activated platelets, which activation was blocked by an anti-FcγIIa antibody, indicating that platelet activation of CD15415c8-IgG1 IC is mediated by FcγRIIa on platelets. ADP: positive control. PBS: negative control. Five donors were evaluated for platelet activation. The results are shown as mean of each experiment±SD.

C4LB231 and C4LB232 were also tested for their effect on platelets. Neither shCD154:C4LB231 nor shCD154: C4LB232 ICs activated platelets over the baseline. CD154/5c8IgG1 IC activated platelets, and the activation was blocked in the presence of IV.3, demonstrating that platelet activation was mediated by IC binding to FcγRIIa. FIG. 3 shows the results of the experiment.

Example 8. Anti-CD154 Antibodies Bind Human CD154 with High Affinity

Affinity measurements were done using ProteOn™ as described in Example 1. The on-rate, off-rate and affinity are shown in Table 16. The parameters reported in this table were obtained from a 1:1 Langmuir binding model for all samples, except C4LB94 and C4LB150 that fitted with two-states binding model.

TABLE 16

| Sample | ka (1/Ms) | kd (1/s) | $K_D$ (M) |
| --- | --- | --- | --- |
| C4LB5 | 5.70E+05 | 1.78E−04 | 3.12E−10 |
| C4LB89 | 1.61E+06 | 3.80E−04 | 2.35E−10 |
| C4LB94 | 1.58E+06 | 3.29E−03 | 2.09E−09 |
| C4LB150 | 2.27E+06 | 6.17E−03 | 2.72E−09 |
| C4LB189 | 3.55E+05 | 2.06E−04 | 5.81E−10 |
| C4LB191 | 5.62E+06 | 1.76E−04 | 3.13E−11 |
| C4LB199 | 1.60E+06 | 4.04E−04 | 2.53E−10 |

Example 9. Crystal Structure of Marmoset CD154 in Complex with C4LB89

The epitope of antibody C4LB89 was identified using X-ray crystallography. The His-tagged Fab fragment of C4LB89 and the His-tagged soluble form of marmoset CD40L (smCD154-his) were expressed in HEK293 GnTI cells and purified using affinity and size-exclusion chromatography. The smCD154:C4LB89 complex was incubated overnight at 4° C., concentrated, and separated from the uncomplexed species using size-exclusion chromatography. The complex was crystallized by the vapor-diffusion method from solution containing 16% PEG 3350, 0.2 M ammonium citrate, 0.1 M MES, pH 6.5. The crystals belong to the cubic space group P213 with unit cell dimensions of 162.1 Å. The structure of the complex was determined by the molecular replacement method using the crystal structures of the C4LB89 Fab and CD40L (PDB entry 1ALY) as search models.

Figure 4:
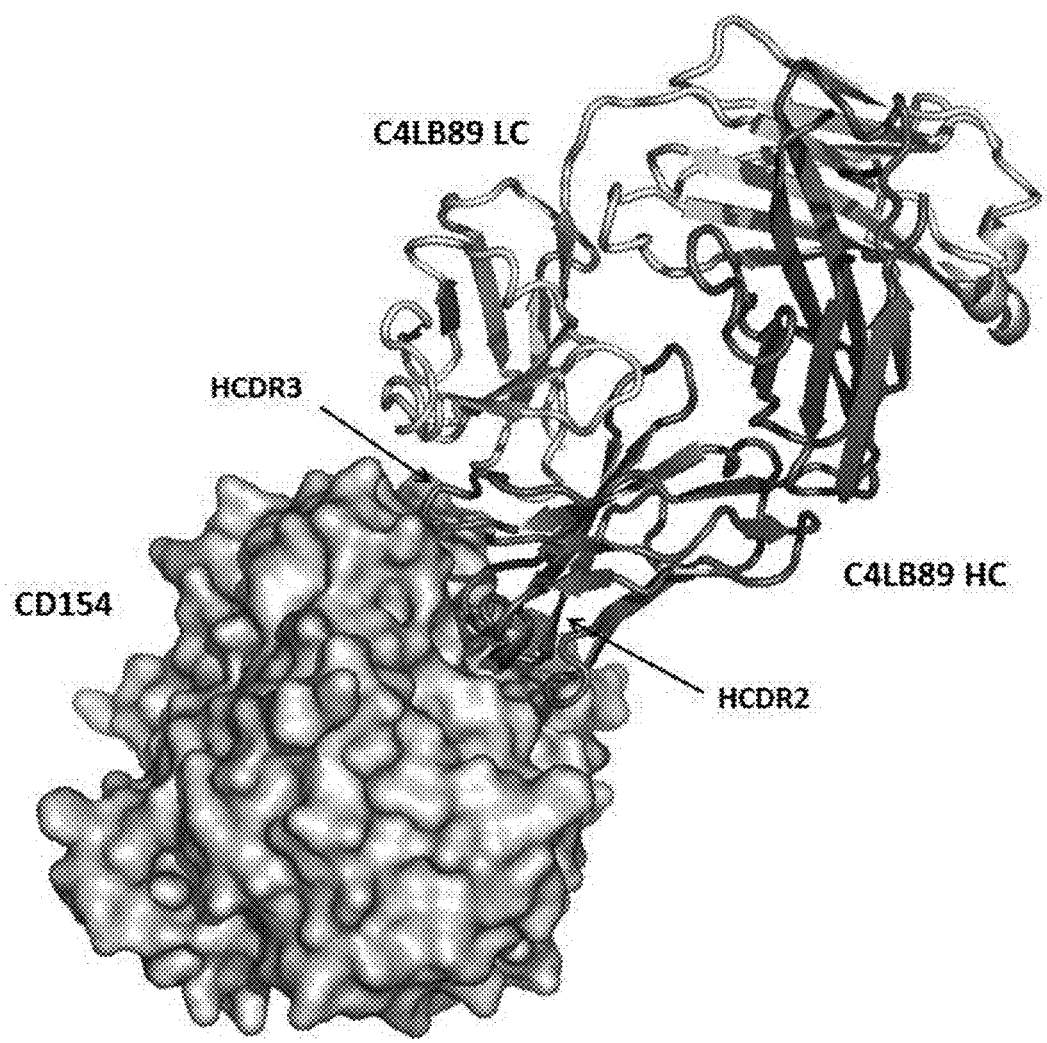
FIG. 4 shows the interaction surface between CD154 and C4LB89. Aromatic residues F55, Y101 and Y102 in HCDR2 and HCDR3 contribute to most interactions (residue numbering according to SEQ ID NO: 59). Light chain of C4LB89 does not contribute to binding.
Figure 5:
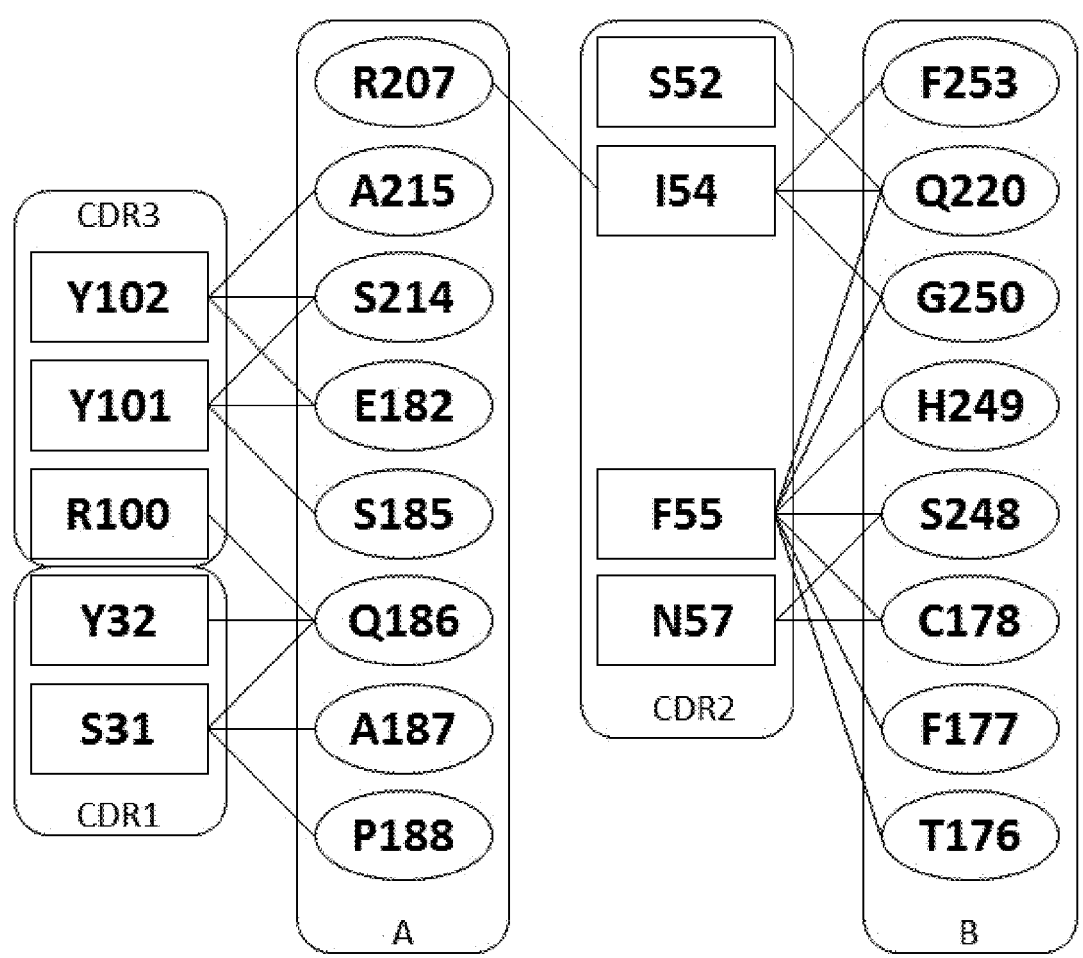
FIG. 5 shows a two-dimensional cartoon of epitope and paratope residues identified from crystal structure of marmoset CD154 in complex with C4LB89. The epitope residues are circled with an ellipse and the paratope residues in heavy chain HCDR1, HCDR2 and HCDR3 are shown (indicated as CDR1, CDR2 and CDR3 in the Figure). The antibody binds simultaneously to two CD154 monomers A and B. Epitope residue numbering is according to human CD154 (SEQ ID NO: 1) and paratope residue numbering is according to heavy chain variable region of C4LB89 (SEQ ID NO: 59).

The smCD154:C4LB89 complex is a symmetric trimer sitting on the crystallographic 3-fold axis. C4LB89 binds mCD154 at the interface between two subunits at the epitope distal from the cell surface. The epitope includes 16 residues, 8 from each of two CD154 subunits. The epitope residues are E182, S185, Q186, A187, P188, S214, A215 and R207 in the first CD154 subunit and T176, F177, C178, Q220, S248, H249, G250 and F253 in the second CD154 subunit. Epitope residue numbering is according to full length human CD154 of SEQ ID NO: 1. The paratope is defined as antibody residues within 4 Å from the CD154 residues. The C4LB89 paratope includes 9 residues from the heavy chain of C4LB89: S31 and Y32 from HCDR1, S52, I54, F55 and N57 from HCDR2 and R100, Y101 and Y102 from HCDR3. Paratope residue numbering is according to C4LB89 VH of SEQ ID NO: 59. The light chain is not involved in contacts with mCD154. Based on the number of contacts, F55 in HCDR2 is a key antigen recognition element. F55 makes contact to CD154 residues T176, F177, C178, Q220, S248, H249, G250 and F253. HCDR3 residues Y101 and Y102 also contribute to binding. FIG. 4 shows the HCDR2 and HCDR3 contact residues and lack of binding of the LC to CD154. FIG. 5 shows a cartoon of the epitope and paratope residues.

Human and marmoset soluble CD154 proteins differ by 8 amino acid residues only. All mCD154 C4LB89 epitope residues are conserved in human. Therefore, it is expected that the epitope is conserved between marmoset and human CD154. The alignment of the full length human and marmoset CD154 proteins are shown in FIG. 6.

Example 10. Platelet Activation by Anti-CD154 Antibodies is Epitope Dependent C4LB89 variable regions (VH of SEQ ID NO: 59 and VL of SEQ ID NO: 66) were cloned as IgG1/κ, resulting in C4LB237 antibody. C4LB237 was confirmed to retain binding human CD154 (Table 17) as measured using ProteOn™ as described in Example 1. The affinity of C4LB237 to human CD154 was 23.6±5.4 pM. Switching isotype of the VH/VL derived from C4LB89 from IgG2sigma to IgG1 appeared to change the binding affinity of the resulting antibody.

As expected, C4LB237 bound human FcγRIIa and FcγRIIIa with a $K_D$ of 0.994 μM and 0.146 μM, respectively. C4LB237 showed comparable potency to C4LB231 and higher potency than C4LB89 in NF-κB SEAP reporter gene assay when shCD154-his was used to induce signaling (Table 18).

Figure 7:
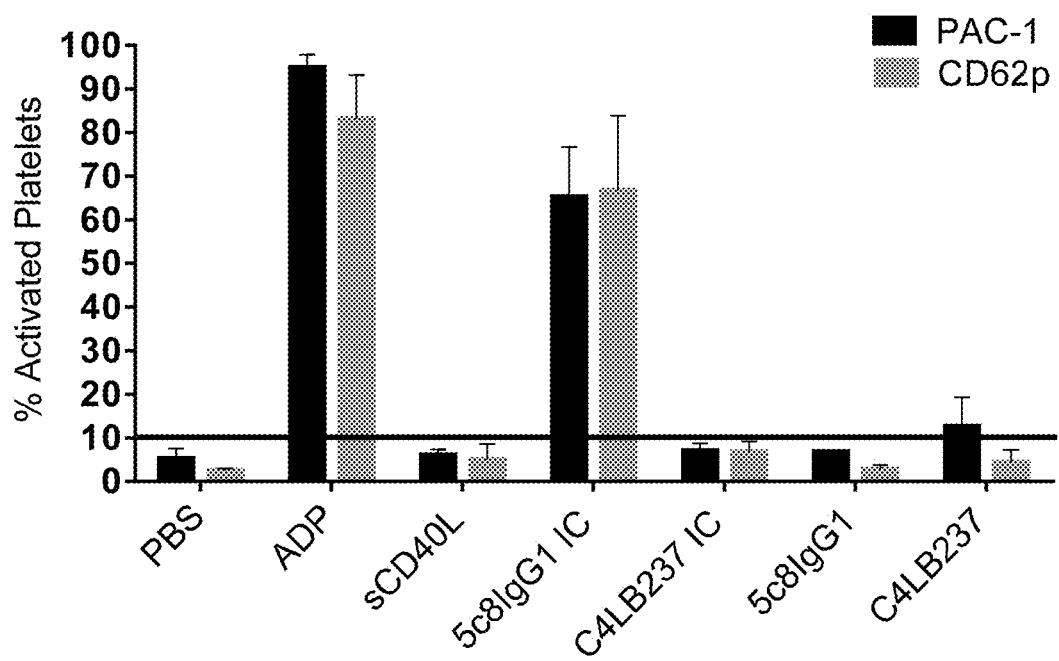
FIG. 7 shows that immune complexes (IC) of shCD154 (sCD40L in the Figure) and an IgG1/κ anti-CD154 antibody C4LB237 do not activate platelets, whereas IC of shCD154 and another IgG1 antibody 5c8 activate platelets. Antibodies alone had no effect on platelet activation, which was assessed as % of total platelets expressing PAC-1 and CD62p. ADP: positive control. PBS: negative control. Five donors were evaluated for platelet activation. The results are shown as mean of each experiment±SD. n=4 in each group.

C4LB237 was tested for its effect on platelet activation. shCD154:C4LB237 ICs did not activate platelets over the baseline, as shown in FIG. 7. This result suggests that in addition to the Fc, the epitope of the antibody contributes to the ability or inability of the antibody to activate platelets.

TABLE 17

| Sample | ka (1/Ms) $10^6$ | kd (1/s) $10^{-05}$ | $K_D$ (pM) |
| --- | --- | --- | --- |
| C4LB231 (n = 8) | 2.53 ± 0.15 | 7.81 ± 0.69 | 31.0 ± 3.3 |
| C4LB232 (n = 8) | 2.54 ± 0.15 | 8.89 ± 0.91 | 35.2 ± 5.2 |
| C4LB237 (n = 4) | 2.59 ± 0.20 | 6.05 ± 0.98 | 23.6 ± 5.4 |

TABLE 18

| mAb | $IC_{50}$ (nM) | 95% CI $IC_{50}$ (nM) |
| --- | --- | --- |
| C4LB231 | 2.32 | 2.11-2.55 |
| C4LB237 | 2.56 | 2.43-2.70 |
| C4LB89 | 6.22 | 5.27-7.34 |

Example 11. Engineering Neutral Mutations on C4LB89

Analyses of the crystal structure of C4LB89 in complex with CD154 revealed positions in the CDRs of C4LB89 which may be mutated without affecting the overall structure of the complex and which therefore are expected not to affect properties of the C4LB89 antibody. These neutral mutations on the light chain CDRs are listed in Table 19 and in the heavy chain CDRS in Table 20. The numbering of the residues that can be mutated is shown both on the individual CDRs and the VL or the VH. For example, residue Q4 on LCDR1 of SEQ ID NO: 37 (RASQSISSYLN) may be mutated to A, C, D, E, F, G, H, I, K, L, M, N, R, S, T, V, W or Y with the expectation that the characteristics of the antibody do not change substantially. The corresponding residue in the VL of SEQ ID NO: 66 is Q27.

Mutations shown in Table 19 or Table 20 are made singularly or in combination onto C4LB89 using standard methods. The resulting VH/VL pairs are expressed and the mutated antibodies isolated and characterized using methods described herein.

TABLE 19

| C4LB89 LCDR | C4LB89 LCDR residue | C4LB89 VL (SEQ ID NO: 66) residue | Possible substitutions |
|---|---|---|---|
| LCDR1 SEQ ID NO: 37 (RASQSISSYLN), | Q4 | Q27 | A, C, D, E, F, G, H, I, K, L, M, N, R, S, T, V, W, Y |
| | S5 | S28 | A, C, D, E, F, G, H, I, K, L, M, N, Q, R, T, V, W, Y |
| | S7 | S30 | A, C, D, E, F, G, H, I, K, L, M, N, Q, R, T, V, W, Y |
| | S8 | S3 | A, C, D, E, F, G, H, I, K, L, M, N, Q, R, T, V, W, Y |
| CDR2 of SEQ ID NO: 44 (YANSLQS) | A2 | A51 | S |
| | N3 | N52 | A, C, D, E, F, G, H, I, K, L, M, Q, R, S, T, V, W, Y |
| | S4 | S53 | A, C, D, E, F, G, H, I, K, L, M, N, Q, R, T, V, W, Y |
| | L5 | L54 | A, C, D, E, F, G, H, I, K, M, N, Q, R, S, T, V, W, Y |
| | Q6 | Q55 | E, D, N |
| | S7 | S56 | A, C, D, E, F, G, H, I, K, L, M, N, Q, R, T, V, W, Y |
| LCDR3 of SEQ ID NO: 52 (QQSDSIPWT), | S3 | S91 | A |
| | D4 | D92 | N |
| | S5 | S93 | A, C, D, E, F, G, H, I, K, L, M, N, Q, R, T, V, W, Y |
| | I6 | I94 | A, C, D, E, G, K, L, M, N, Q, R, S, T, V |

TABLE 20

| C4LB89 HCDR | C4LB89 HCDR residue | C4LB89 VH (SEQ ID NO: 59) Residue position | Possible substitutions |
|---|---|---|---|
| HCDR1 SEQ ID NO: 17 (SYGIS) | S1 | S31 | A, C, D, E, G, I, K, L, M, N, Q. R, T, V |
| | I4 | I34 | M, L, V |
| | S5 | S35 | A |
| HCDR2 of SEQ ID NO: 23 (WISPIFGNTNYA QKFQG) | S3 | S52 | A, T, V |
| | I5 | I54 | V, T, L Q, E |
| | N8 | N57 | A, C, D, E, F, G, H, I, K, L, M, Q, R, S, T, V, W, Y |
| | T9 | T58 | A, C, D, E, F, G, H, I, K, L, M, N, Q, R, S, V, W, Y |
| | N10 | N59 | A, C, D, E, F, G, H, I, K, L, M. Q, R, S, T, V, W, Y |
| HCDR3 of SEQ ID NO: 30 (SRYYGDLDY), | S1 | S99 | A, M |
| | R2 | R100 | A, S, Q, K |
| | R7 | L105 | M |

Example 12. Evaluation of Platelet Activation and Higher Order Immune Complex Formation Upon evaluation of the crystal structure data for Fab region and shCD154 complex for C4LB231 and 5C8IgG1 earlier experiments with SC-HPLC and DLS as well as review of the platelet activation data, it was hypothesized that slight differences in binding of anti-CD154 antibodies with the shCD154 trimer may facilitate higher order immune complex formation: 1) the C4LB231 Fab binds between 2 subunits of the sCD154 trimer while 5C8 Fab binds 1 subunit of sCD154, 2) the C4LB231 Fab appears to be more rigid in this conformation than the 5c8 Fab 3) and the angle of binding of the anti-CD154 antibody with sCD154.

In order to further evaluate the role of the antibody epitope mediating platelet activation and higher order immune complex formation with shCD154, the VH and the VL of various anti-CD154 antibodies were cloned and expressed as Fc silent IgG2sigma and IgG1sigma isotypes or as IgG1. The generated antibodies are shown in Table 21. Platelet activation assays were done as described in Example 6. For the higher order immune complex formation evaluations via size exclusion high performance liquid chromatography (SE-HPLC) and dynamic light scattering (DLS), the antibodies were complexed with shCD154 at 1:1 (aka 10:10) and 10:1 molar ratios to evaluate if there were concentration dependent differences in immune complexation.

TABLE 21

| Antibody name | Isotype | VH SEQ ID NO: | VL SEQ ID NO: |
|---|---|---|---|
| 5C8IgG2sigma (C4LB71) | IgG2σ | 74 | 75 |
| 5C8IgG1 (MSCB8) | IgG1 | | |
| C4LB89 | IgG2σ | 59 | 66 |
| C4LB231 | IgG1σ | | |
| C4LB237 | IgG1 | | |
| C4LB119 | IgG2σ | 84 | 85 |
| C4LB290 | IgG1σ | | |
| C4LB287 | IgG1 | | |
| C4LB83 | IgG2σ | 86 | 87 |
| C4LB288 | IgG1 | | |
| C4LB94 | IgG2σ | 60 | 67 |
| C4LB234 | IgG1σ | | |
| C4LB289 | IgG1 | | |

IgG2σ: IgG2sigma

IgG1σ: IgG1sigma

SEQ ID NO: 84 VH of C4LB119
QVQLVQSGAEVKKPGSSVKVSCKASGGTFSSYYISWVRQAPGQGLEWMG
AIDPYFGYANYAQKFQGRVTITADESTSTAYMELSSLRSEDTAVYYCAR
TGLNYGGFDYWGQGTLVTVSS

SEQ ID NO: 85 VL of C4LB119
EIVLTQSPATLSLSPGERATLSCRASQSVSSYLAWYQQKPGQAPRLLIY
DASNRATGIPARFSGSGSGTDFTLTISSLEPEDFAVYYCQQRSNWPLTF
GQGTKVEIK

SEQ ID NO: 86 VH of C4LB83
QVQLVQSGAEVKKPGSSVKVSCKASGGTFSSYAISWVRQAPGQGLEWMG
WIIPIFGNTNYAQKFQGRVTITADESTSTAYMELSSLRSEDTAVYYCAR
EKDFRGYTKLDYWGQGTLVTVSS

SEQ ID NO: 87 VL of C4LB83
DIQMTQSPSSLSASVGDRVTITCRASQSINNWLNWYQQKPGKAPKLLIY
AASSLQSGVPSRFSGSGSGTDFTLTISSLQPEDFATYYCQQSFSFPYTF
GQGTKVEIK

C4LB83 and C4LB119 binding characteristics and functionality was assessed using protocols described in Example 1 and are shown in Table 22.

TABLE 22

| Antibody | ka (1/Ms) | kd (1/s) | $K_D$ (M) | B cell activation assay IC$_{50}$ (nM)* |
|---|---|---|---|---|
| C4LB83 | 2.10E+06 | 4.70E−03 | 2.23E−09 | 0.64-1.09 |
| C4LB119 | 1.84E+06 | 8.80E−03 | 4.79E−09 | 0.81-2.03 |

*shCD154-ILZ induced activation of human B cells. The range indicates the lowest and highest IC$_{50}$ value obtained in separate experiments across 2 donors Methods

SE-HPLC

Immune complexes of antibodies shown in Table 21 and Alexafluo-448 labeled shCD154 were prepared at 1:1 and 10:1 antibody:shCD154 molar ratio in 110 µL of 1×PBS and incubated at 37° C. for 30 min. 100 µL of each sample were injected to column (Agilent, 1100/1200 system) for each run, which contained 5 µg of AF488 labeled shCD154 and 15 µg (1:1 ratio), or 150 µg (10:1 ratio) of anti-CD154 mAb. Molecular weight was calculated based on the retention time of the standards (Bio-Rad). The relationship between the molecular weight and retention time of the protein satisfies the equation:

$$\log(M)=b-cT,$$

where M is the molecular weight, T is the retention time, and b and c are constants. A linear curve of log(M) and T was obtained from the standard SE-HPLC chromatogram by least squares fitting, with $R^2$=0.9928.

DLS

DLS measurement is based on light scattering principles and molecular or Brownian Motion. Brownian motion, a typically behavior of molecules in solution, causes light scattered to be both in and out of phase, resulting in constructive and destructive interferences. The result is that the intensity of the scattered light fluctuates with time. During DLS or QELS (quasi-electric light scattering) analysis, this time-dependent fluctuation in the scattered light intensity is captured by a fast photon counter. The fluctuations are directly proportional to the rate of diffusion. Resolution of the correlation data using the Stokes-Einstein equation yields the hydrodynamic radius. Unlike SEC-MALS, or SEC, where sample resolution can distinguish between monomer and dimer, DLS is only able to resolve species that are separated by a size factor of ~4, therefore monomer and tetramer will begin to be resolved; however monomer through dimer will not, but will report a weighted average of the mixture.

Stokes-Einstein equation: $R_h=kT/6\pi\eta D$; wherein

D=diffusion coefficient, k=Boltzmann's constant

T=temperature

η=viscosity

Antibodies alone at 10 µM or immune complexes of antibodies shown in Table 21 and shCD154 were prepared at 10:1 or 10:10 molar concentrations of antibody:shCD154 (10 µM antibody with either 1 µM or 10 µM shCD154) in PBS. All samples were prepared in glass vials with vial inserts (250 µL deactivated glass with polymer feet, Agilent cat #5181-8872), and samples were added in the following order: PBS, mAb, shCD154. Samples were mixed by gentle vortexing then incubated at RT, with rocking (Nutating Mixer (VWR) ~30 rev/min for approximately 23 hr. If needed, antibodies were first concentrated using standard methods.

Particle sizes and species distribution in all samples were determined on a DynaPro® Plate Reader DLS instrument (Wyatt Technologies Corporation) at 23° C. DLS consistency was first validated using BSA (data not shown). Measurements were made by introducing 30 µL of sample in each of 3 wells for (triplicate measurements). DLS measurements were acquired in a DynaPro® plate reader. Twenty 5-sec acquisitions were performed on each sample, and laser power was automatically adjusted by the instrument. Parameters used for data analysis included a viscosity at 23° C. for PBS of 1.019 cP and a refractive index value at 589 nm & 23° C. for PBS of 1.333. A globular protein model was used by the program. Signals were bucketed into peaks, where Peak1 was 0.1-10 nm, Peak2 was 10-100 nm, Peak3 was 100-1000 nm and Peak4 was 1000-5000 nm. Visible precipitates (if formed) in the sample were noted. Data analysis was performed using Dynamics software (Wyatt Technology Inc.). Plots of percent mass versus species radius (Rh) were generated. Peak radius, polydispersity, percent mass and percent intensity were calculated and recorded.

Results

Platelet Activation

Ability of the immune complexes of shCD154 and antibodies expressed as Fc silent IgG2sigma or IgG1sigma, or as wild-type IgG1 to activate platelets were assessed. 5c8 antibody cloned on various IgG scaffolds was used as a control. FIG. 3 shows that 5c8IgG1:shCD154 immune complexes activated platelets in FcγRIIa-dependent manner, as an anti-FcγRIIa antibody inhibited 5c8IgG1-mediated platelet activation. 5c8 VH/VL regions cloned on effector silent Fc, IgG1sigma or IgG2sigma lost their ability to activate platelets (FIG. 1). These results are consistent to what has been described earlier. However, unexpectedly, experiments conducted in Example 10 demonstrated that immune complexes with wild-type IgG1 antibody (C4LBB237: shCD154) did not activate platelets (FIG. 7), prompting further studies into possible epitope dependency of platelet activation.

The VH/VL regions of 4 distinct antibodies were cloned as IgG2sigma, IgG1sigma or wild-type IgG1 in order to evaluate the effect of the epitope and/or Fc on platelet activation as well as on formation of higher order immune complexes. Contrary to what has been disclosed earlier in literature, it was found that platelet activation was in some cases mediated by the antibody epitope independent on FcγRIIa-mediated cross-linking.

Figure 8A:
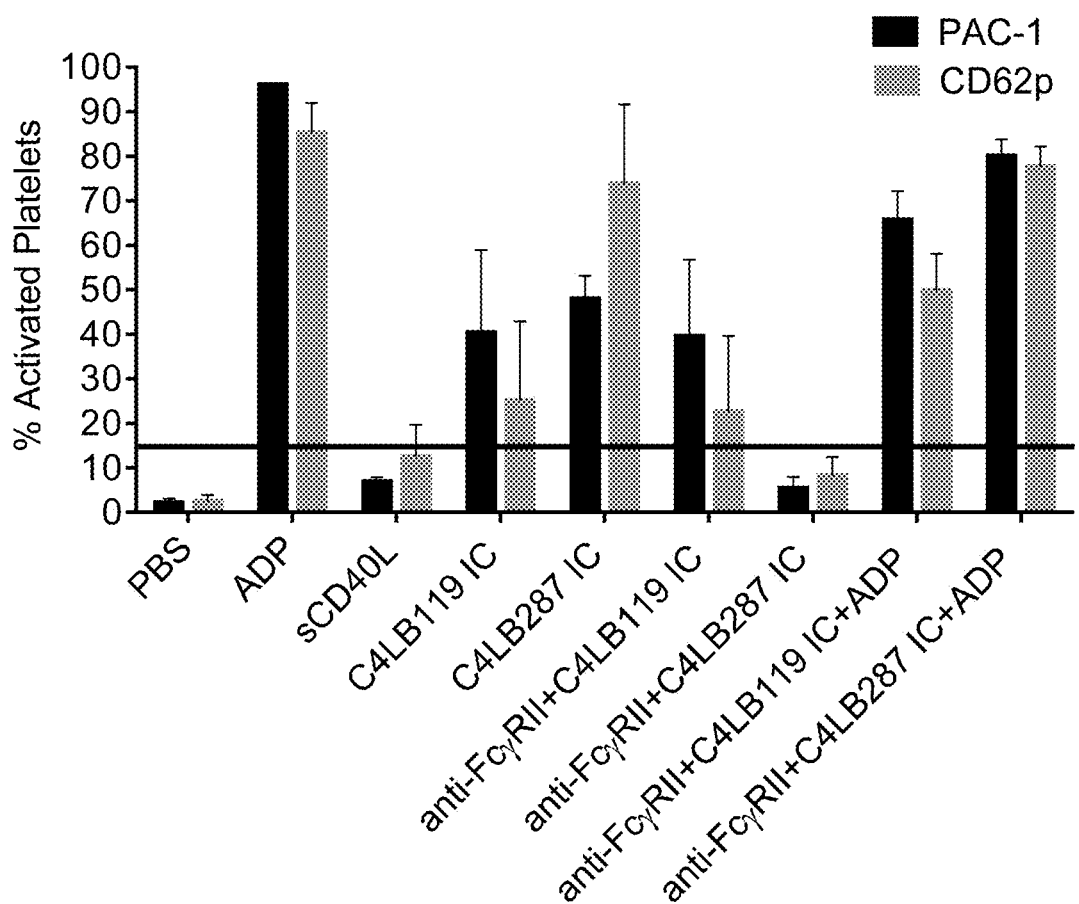
FIG. 8A shows that immune complexes (IC) of shCD154 (sCD40L in the Figure) and a Fc silent C4LB119 activate platelets in FcγRIIa-independent manner, whereas IC of shCD154 and antibody with C4LB119 VH/VL domains expressed on IgG1 (C4LB287) activated platelets in FcγRIIa-dependent manner. ADP: positive control. PBS: negative control.
Figure 8B:
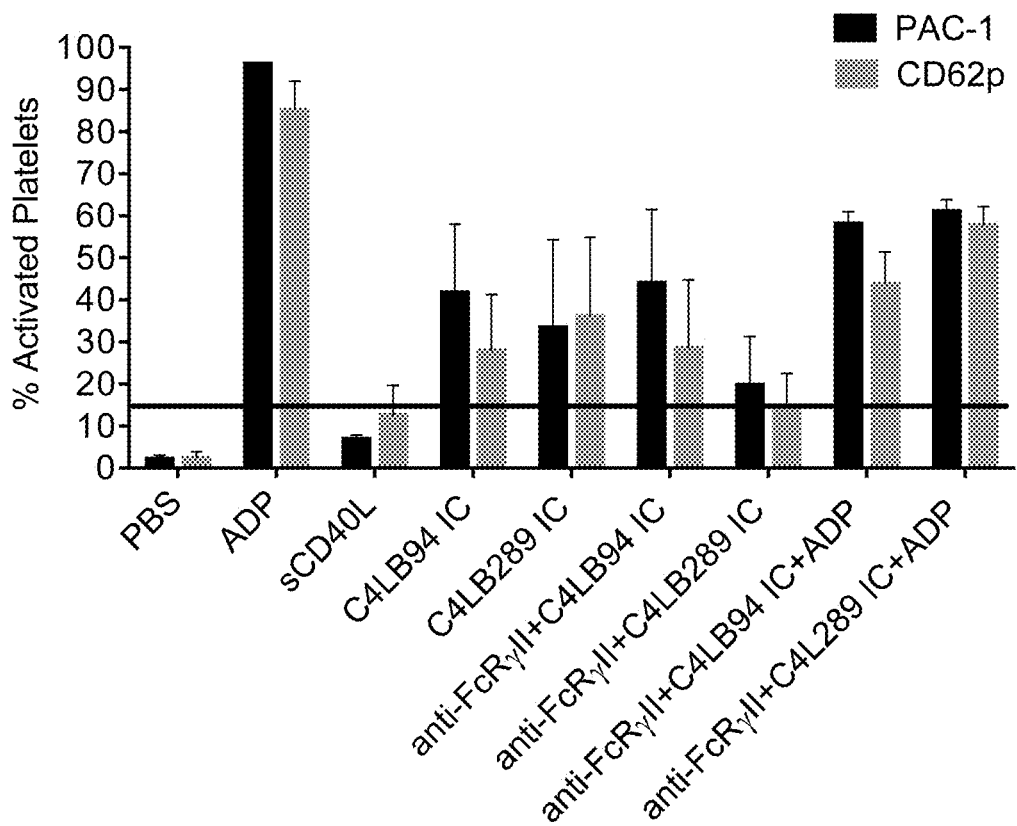
FIG. 8B shows that immune complexes (IC) of shCD154 (sCD40L in the Figure) and a Fc silent C4LB94 activate platelets in FcγRIIa-independent manner, whereas IC of shCD154 and antibody with C4LB94 VH/VL domains expressed on IgG1 (C4LB289) activated platelets in FcγRIIa-dependent manner. ADP: positive control. PBS: negative control.
Figure 8C:
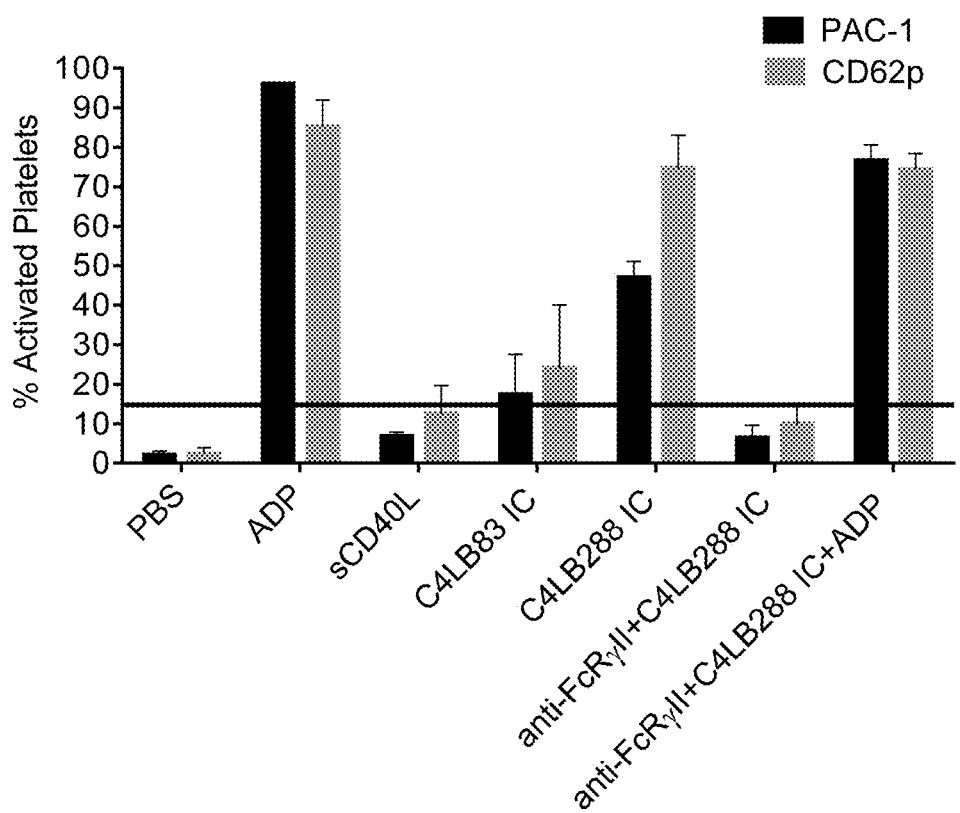
FIG. 8C shows that immune complexes (IC) of shCD154 (sCD40L in the Figure) and a Fc silent C4LB83 moderately activate platelets, whereas IC of shCD154 and antibody with C4LB83 VH/VL domains expressed on IgG1 (C4LB288) activated platelets in FcγRIIa-dependent manner. ADP: positive control. PBS: negative control.

FIG. 8A, FIG. 8B and FIG. 8C shows the summary of the analyses. Immune complexes of Fc silent antibodies C4LB119 (FIG. 8A) and C4LB94 (FIG. 8B) activated platelets in FcγRIIa-independent manner, as pre-block with an anti-FcγRIIa antibody failed to inhibit platelets activation. IC of C4LB83, also an Fc silent antibody, moderately activated platelets (FIG. 8C). IC of antibodies with identical VH/VL domains cloned on wild-type IgG1 in each case activated platelets in FcγRIIa-mediated fashion (C4LB278 in FIG. 8A, C4LB289 in FIG. 8B, and C4LB288 in FIG. 8C). Therefore, several antibodies were identified which mediated platelet activation despite of having a silent Fc. One VH/VL domain pair was identified which mediated platelet activation neither on silent (C4LB231) nor wild-type IgG1 (C4LB237). These data demonstrate that antibody epitope plays a role in mediating platelet aggregation.

Higher Order Immune Complex Formation

SE-HPLC and DLS were used to further evaluate the presence of higher order immune complex formation and the approximate size of these immune complexes between anti-CD154 antibodies shown in Table 21 and shCD154. As shCD154 is a trimer in solution, the expected stoichiometry of the antibody:shCD154 trimer in solution is 3:1. For SE-HPLC, heavier and thus larger immune complexes would have shorter retention times, while lighter and thus smaller immune complexes would have longer retention times, with the exception of very large immune complexes that are unable to elute off the column and evidenced by low % recovery. For DLS, the larger the radius (Rh) value the larger the immune complex. Plate DLS techniques cannot resolve IgG monomers, dimers, trimers and tetramers. Thus Rh values obtained will be a weighted average of monomer-tetramer, therefore Rh values that are closer to 6.5 could represent solutions of mAbs containing higher ordered species, typically dimer. Where binding of mAb to shCD154 is stoichiometric two species may be present—the 3:1 complex (~500 kDa) and unbound antibody (~150 kDa) which corresponds to Rh values of ~8.8 nm and 5-6.5 nm for the 3:1 complex and free mAb respectively. Neither technique can exactly resolve the molecular weight of the immune complexes, but can allow comparative sizes. Table 23 shows the relationship of retention time and hydrodynamic radii to approximate molecular weights.

TABLE 23

| Immune Complex | Approximate Molecular Weight (kDa) | SE-HPLC Retention time (min) | DLS Hydrodynamic Radius (nm) |
|---|---|---|---|
| mAb | 150 | ~9 min | 5 to 6.5 |
| mAb:shCD154 (trimer) | 550 | ~7 min | ~8.8 |
| Higher order immune complexes | ~1000 | <7 min | ~12 |

DLS mAbs in the absence of CD154 and antibody:shCD154 immune complex sizes were evaluated in conditions in which antibody:shCD154 complexes were formed in excess of antibody (10:1 molar ratio) and at equivalent concentration (1:1 molar ratio). Under the conditions where antibody is in excess, the antibody typically saturates CD154 sites to form the immune complex, and excess unbound antibody is present. Under equivalent concentration, no free antibody or free shCD154 is present. The Rh values obtained for each mAb in the absence of sh CD154 and in the presence of sh CD154 at 10:1 and 10:10 molar ratios are shown in Table 24.

A typical mAb with a nominal MW of 150 kDa yields an Rh value of 5.0-6.5 nm. IgG dimers, often seen during size exclusion chromatography, cannot be resolved by plate DLS techniques. The Rh values obtained will be a weighted average of monomer-tetramer, therefore Rh values that are closer to 6.5 could represent solutions of mAbs containing higher ordered species, typically dimer.

For mAbs in the absence of CD154, expected Rh values of 5.5-6.3 nm were observed for all mAbs except C4LB287 and C4LB234, with $R_h$ values of 6.9, and 7.1 nm, respectively, suggested that these antibodies have inherent aggregation tendencies.

The Rh values for the antibody:shCD154 complexes formed at 10:1 ratio were generally less than about 8.8 nm, indicative of the 3:1 stochiometric complex without formation of higher order immune complexes, except for 5c8IgG2sigma (C4LB71) and C4LB234 ($R_h$ values 8.9 and 9.3 nm respectively), indicating that higher order immune complexes were formed.

Increasing shCD154 concentration to 10 μM resulted in antibody:shCD154 immune complexes with elevated Rh when compared to the complexes with 1 μM CD154 (10:1 antibody:CD154 ratio). Some of the antibody:shCD154 complexes demonstrated heterogeneicity with high molecular weight secondary species present ranging from 7-25% of the total mass. C4LB71, 5C8IgG1, C4LB89, C4LB119, C4LB94, C4LB234 and C4LB289 IC Rh values were 22.1, 615, 56.3, 45.0, 18.3, 18.7 and 19.6 nm respectively. In addition, C4LB89, C4LB119, C4LB83, C4LB228 also formed species 900-4000 nm, and C4LB89 and C4LB119 formed precipitates indicating very large immune complexes. Species near 12 nm Rh typically correspond to a mass of 1,000 kDa, therefore these mAbs form very large immune complexes with CD154 under these conditions.

TABLE 24

| Antibody | Isotype | Hydrodynamic radius (Rh), nm | | |
|---|---|---|---|---|
| | | 10:0* | 10:1* | 10:10* |
| 5c8IgG2σ (C4LB71) | IgG2σ | 5.8 | 8.9 | 22.1 |
| 5c8IgG1 | IgG1 | 5.7 | 8.3 | 19.6 |
| C4LB89 | IgG2σ | 5.9 | 5.3, (4082) | 615 ppt |
| C4LB231 | IgG1σ | 5.9 | 8.2 | 10.5 |

TABLE 24-continued

| | | Hydrodynamic radius (Rh), nm | | |
|---|---|---|---|---|
| Antibody | Isotype | 10:0* | 10:1* | 10:10* |
| C4LB237 | IgG1 | 6.1 | 7.4 | 9.8 |
| C4LB119 | IgG2σ | 6.3 | 8.0 | 56.3 ppt |
| C4LB290 | IgG1σ | 6.1 | 8.3 | 13.3 |
| C4LB287 | IgG1 | 6.9 | 8.2 | 12.9 |
| C4LB83 | IgG2σ | 6 | 6.1 | 14.5, (3632) |
| C4LB288 | IgG1 | 6.1 | 6.6 | 10.9 |
| C4LB94 | IgG2σ | 6.1 | 6.9 | 45 |
| C4LB234 | IgG1σ | 7.1 | 9.3, (83) | 5.3, (18.3) |
| C4LB289 | IgG1 | 5.6, | 7.8, (17, 1350) | 3.7, (18.7) |

*Antibody:shCD154 ratio
Rh of secondary species were included in parenthesis if the % mass was ≥25%
ppt: solution precipitated
IgG2σ: IgG2sigma
IgG1σ: IgG1sigma

SE-HPLC

Table 25 shows the Retention time, recovery rate, and estimated molecular weight (MW) of anti-CD154 antibodies alone and in immune complex with shCD154 obtained from the SE-HPLC analyses. A typical antibody has a MW of about 150 kD, and shCD154 trimer has a MW of about 50 kDa. Therefore, a mAb:shCD154 trimer complex with 3:1 stoichiometry has an expected MW of about 500 kDa.

TABLE 25

| mAb ID | Type | Ratio* | Retention Time (min) | Peak Area | % Recovery | MW (kDa) |
|---|---|---|---|---|---|---|
| 5c8IgG2σ (C4LB71) | IgG2σ | 1:1 | 6.24 | 6887 | 85.2 | 1596.8 |
| | | 10:1 | 6.28 | 7348 | 90.9 | 1538.2 |
| 5c8IgG1 | IgG1 | 1:1 | 7.3 | 1096 | 55.7 | 592.8 |
| | | 10:1 | 6.92 | 3280 | 69.2 | 845.6 |
| C4LB89 | IgG2σ | 1:1 | 6.19 | 356 | 16.9** | 1673.2 |
| | | 10:1 | 6.35 | 3662 | 45.3** | 1440.8 |
| C4LB231 | IgG1σ | 1:1 | 6.97 | 6766 | 83.8 | 807 |
| | | 10:1 | 6.97 | 7181 | 88.9 | 807 |
| C4LB237 | IgG1 | 1:1 | 6.99 | 6506 | 80.5 | 792.1 |
| | | 10:1 | 6.99 | 7977 | 98.7 | 792.1 |
| C4LB119 | IgG2σ | 1:1 | 9.59 | 307 | 5.6** | 69.7 |
| | | 10:1 | 8.02 | 4667 | 8.3** | 302.4 |
| C4LB290 | IgG1σ | 1:1 | 7.01 | 4957 | 61.4 | 777.4 |
| | | 10:1 | 7.01 | 6983 | 86.4 | 777.4 |
| C4LB287 | IgG1 | 1:1 | 7 | 5937 | 73.5 | 784.7 |
| | | 10:1 | 7.02 | 8011 | 99.2 | 770.2 |
| C4LB83 | IgG2σ | 1:1 | 7.86 | 5193 | 64.3 | 351.2 |
| | | 10:1 | 7.84 | 3355 | 86.9 | 357.8 |
| C4LB288 | IgG1 | 1:1 | 7.62 | 4169 | 70.6 | 439.5 |
| | | 10:1 | 7.37 | 5582 | 95.5 | 555.2 |
| C4LB94 | IgG2σ | 1:1 | 6.01 | 3233 | 40.0** | 1979.9 |
| | | 10:1 | 6.02 | 7748 | 95.9 | 1961.5 |
| C4LB234 | IgG1σ | 1:1 | 6.26 | 5534 | 86.6 | 1567.3 |
| | | 10:1 | 6.53 | 7922 | 98.1 | 1217.6 |
| C4LB289 | IgG1 | 1:1 | 6.25 | 5800 | 83.5 | 1582 |
| | | 10:1 | 6.53 | 7958 | 98.5 | 1217.6 |

*(mAb:CD154)
**Recovery rate <50% Antibodies with identical VH/VL are separated into groups divided by empty rows
IgG2σ: IgG2sigma
IgG1σ: IgG1sigma All antibodies formed an immune complex with shCD154. C4LB231, C4LB237, C4LB290, C4LB287 (all IgG1sigma) formed an immune complex with sCD154 and eluted at 7.0 min however C4LB290 and C4LB287 had lower % recoveries at the 1:1 condition compared to the 10:1 condition while C4LB231 and C4LB237 had higher % recoveries (>80%). C4LB289 (IgG1), C4LB234 (IgG1sigma), 5c8IgG1sigma (C4LB71) and C4LBB94 (IgG2sigma) eluted earlier at 6.2 to 6.5 min indicating larger complexes were formed than with the aforementioned mAbs. 5c8IgG1 had a broad peak at the expected retention time for the 3:1 mAb:shCD154 trimer immune complex, however the broad peak and lower recovery (56% at the 1:1 condition) indicated that higher order immune complexes may have formed which may have either interacted with or did not enter the column. C4LB89 and C4LB119 (both IgG2sigma) formed complex with shCD154 and eluted with a broad peak and very low recovery (6-17% at the 1:1 condition), likely due to the formation of large complexes which did not enter the column. In general, antibodies on IgG2sigma isotypes formed larger immune complexes when compared to the antibodies on IgG1sigma or IgG1.

Table 26 shows a summary of antibody characteristics. Overall, the platelet activation data, the SE-HPLC and DLS data together indicate that platelet activation is not entirely attributed to an active Fc. The data indicates that antibodies with silent Fc such as IgG1sigma and IgG2sigma are capable of forming larger size immune complexes greater than that of the expected 3:1 mAb to shCD154 trimer complex and that some antibodies on silent Fc are capable of platelet activation. The data supports a conclusion that both the VH/VL domains (e.g. the epitope the antibody binds to) and the higher order immune complex formation contribute to platelet activation.

TABLE 26

| Antibody | Isotype | Platelet activation** | Platelet activation independent on FcγRIIa | IC SE-HPLC RT (min) | | IC DLS Rh (nm) | |
|---|---|---|---|---|---|---|---|
| | | | | 10:1* | 1:1* | 10:1* | 10:10* |
| 5c8IgGσ (C4LB71) | IgG2σ | No | | 6.3 | 6.2 | 8.9 | 22.1 |
| 5c8IgG1σ | IgG1σ | No | | | | | |
| 5c8IgG1 | IgG1 | Yes | No | 6.9 | 7.3 | 8.3 | 19.6 |
| C4LB89 | IgG2σ | No | | 6.4# | 6.2# | 5.3, 4082^ | 615 p |
| C4LB231 | IgG1σ | No | | 7.0 | 7.0 | 8.2 | 10.5 |
| C4LB237 | IgG1 | No | | 7.0 | 7.0 | 7.4 | 9.8 |
| C4LB119 | IgG2σ | Yes | Yes | 8.0# | 9.6# | 8.0 | 56.3 p |
| C4LB290 | IgG1σ | | | 7.0 | 7.0 | 8.3 | 13.3 |
| C4LB287 | IgG1 | Yes | No | 7.0 | 7.0 | 8.2 | 12.9 |
| C4LB83 | IgG2σ | Marginal | Yes | 7.8 | 7.9 | 6.1 | 14.5, 3632^ |

TABLE 26-continued

| Antibody | Isotype | Platelet activation** | Platelet activation independent on FcγRIIa | IC SE-HPLC RT (min) 10:1* | 1:1* | IC DLS Rh (nm) 10:1* | 10:10* |
|---|---|---|---|---|---|---|---|
| C4LB288 | IgG1 | Yes | No | 7.4 | 7.6 | 6.6 | 10.9 |
| C4LB94 | IgG2σ | Yes | Yes | 6.0 | 6.0# | 6.9 | 45 |
| C4LB234 | IgG1σ | | | 6.5 | 6.3 | 9.3 | 5.3, 18.3^ |
| C4LB289 | IgG1 | Yes | No | 6.5 | 6.3 | 7.8 | 3.7, 18.7 |

*antibody:shCD154 ratio
**assessment using either PAC-1 or CD62p expression
SE-HPLC % recovery <50%
^Rh of secondary species were included if the % mass was ≥25%
p: solution precipitated
IgG2σ: IgG2sigma
IgG1σ: IgG1sigma

We claim:

1. An isolated antagonistic antibody or an antigen binding portion thereof specifically binding human CD154 of SEQ ID NO: 1, comprising a light chain complementarity determining region (LCDR) 1 of SEQ ID NO: 37 (RASQSISSYLN), a LCDR2 of SEQ ID NO: 44 (YANSLQS), a LCDR3 of SEQ ID NO: 52 (QQSDSIPWT), a heavy chain complementarity determining region (HCDR) 1 of SEQ ID NO: 17 (SYGIS), a HCDR2 of SEQ ID NO: 23 (WISPIFGNTNYAQKFQG), and a HCDR3 of SEQ ID NO: 30 (SRYYGDLDY), wherein optionally:

a) the LCDR1 residue Q4 is mutated to A, C, D, E, F, G, H, I, K, L, M, N, R, S, T, V, W or Y;
b) the LCDR1 residue S5 is mutated to A, C, D, E, F, G, H, I, K, L, M, N, Q, R, T, V, W or Y;
c) the LCDR1 residue S7 is mutated to A, C, D, E, F, G, H, I, K, L, M, N, Q, R, T, V, W or Y;
d) the LCDR1 residue S8 is mutated to A, C, D, E, F, G, H, I, K, L, M, N, Q, R, T, V, W or Y;
e) the LCDR2 residue A2 is mutated to S;
f) the LCDR2 residue N3 is mutated to A, C, D, E, F, G, H, I, K, L, M, Q, R, S, T, V, W or Y;
g) the LCDR2 residue S4 is mutated to A, C, D, E, F, G, H, I, K, L, M, N, Q, R, T, V, W or Y;
h) the LCDR2 residue L5 is mutated to A, C, D, E, F, G, H, I, K, M, N, Q, R, S, T, V, W or Y;
i) the LCDR2 residue Q6 is mutated to E, D or N;
j) the LCDR2 residue S7 is mutated to A, C, D, E, F, G, H, I, K, L, M, N, Q, R, T, V, W or Y;
k) the LCDR3 residue S3 is mutated to A;
l) the LCDR3 residue D4 is mutated to N;
m) the LCDR3 residue S5 is mutated to A, C, D, E, F, G, H, I, K, L, M, N, Q, R, T, V, W or Y;
n) the LCDR3 residue 16 is mutated to A, C, D, E, G, K, L, M, N, Q, R, S, T or V;
o) the HCDR1 residue S1 is mutated to A, C, D, E, G, I, K, L, M, N, Q, R, T or V;
p) the HCDR1 residue 14 is mutated to M, L or V;
q) the HCDR1 residue S5 is mutated to A;
r) the HCDR2 residue S3 is mutated to A, T or V;
s) the HCDR2 residue P4 is mutated to V, T, L Q or E;
t) the HCDR2 residue N8 is mutated to A, C, D, E, F, G, H, I, K, L, M, Q, R, S, T, V, W or Y;
u) the HCDR2 residue T9 is mutated to A, C, D, E, F, G, H, I, K, L, M, Q, R, S, T, V, W or Y;
v) the HCDR2 residue N10 is mutated to A, C, D, E, F, G, H, I, K, L, M, Q, R, S, T, V, W or Y;
w) the HCDR3 residue Si is mutated to A or M;
x) the HCDR3 residue R2 is mutated to A, S, Q or K; or
y) the HCDR3 residue L7 is mutated to M.

2. An isolated antagonistic antibody or an antigen binding portion thereof specifically binding human CD154 of SEQ ID NO: 1, comprising a heavy chain complementarity determining region (HCDR) 1 of SEQ ID NO: 17 (SYGIS), a HCDR2 of SEQ ID NO: 23 (WISPIFGNTNYAQKFQG) and a HCDR3 of SEQ ID NO: 30 (SRYYGDLDY), wherein optionally a) the HCDR1 residue S1 is mutated to A, C, D, E, G, I, K, L, M, N, Q, R, T or V;
b) the HCDR1 residue 14 is mutated to M, L or V;
c) the HCDR1 residue S5 is mutated to A;
d) the HCDR2 residue S3 is mutated to A, T or V;
e) the HCDR2 residue P4 is mutated to V, T, L Q or E,
f) the HCDR2 residue N8 is mutated to A, C, D, E, F, G, H, I, K, L, M, Q, R, S, T, V, W or Y;
g) the HCDR2 residue T9 is mutated to A, C, D, E, F, G, H, I, K, L, M, Q, R, S, T, V, W or Y;
h) the HCDR2 residue N10 is mutated to A, C, D, E, F, G, H, I, K, L, M, Q, R, S, T, V, W or Y;
i) the HCDR3 residue Si is mutated to A or M;
j) the HCDR3 residue R2 is mutated to A, S, Q or K;
k) the HCDR3 residue L7 is mutated to M; and
a light chain complementarity determining region (LCDR) 1, a LCDR2 and a LCDR3 of:
a) SEQ ID NOs: 36, 43 and 51, respectively;
b) SEQ ID NOs: 37, 44 and 52, respectively;
c) SEQ ID NOs: 38, 45 and 53, respectively;
d) SEQ ID NOs: 39, 46 and 54, respectively;
e) SEQ ID NOs: 40, 47 and 55, respectively;
f) SEQ ID NOs: 41, 47 and 56, respectively;
g) SEQ ID NOs: 42, 48 and 57, respectively;
h) SEQ ID NOs: 37, 49 and 52, respectively; or
i) SEQ ID NOs: 37, 50 and 52, respectively.

3. The antibody or antigen binding portion thereof of claim 1, comprising the HCDR1 of SEQ ID NO: 17 (SYGIS), the HCDR2 of SEQ ID NO: 23 (WISPIFGNTNYAQKFQG), the HCDR3 of SEQ ID NO: 30 (SRYYGDLDY), the LCDR1 of SEQ ID NO: 37 (RASQSISSYLN), the LCDR2 of SEQ ID NO: 44 (YANSLQS) and the LCDR3 of SEQ ID NO: 52 (QQSDSIPWT).

4. The antibody or antigen binding portion thereof of claim 1, wherein the antibody has at least one of the following properties:

a) an immune complex of the antibody and soluble human CD154 (shCD154) does not activate platelets, wherein platelet activation is measured by P-selectin surface expression on platelets;

b) binds to CD154 with a dissociation constant ($K_D$) of about $5\times10^{-9}$M or less, when the $K_D$ is measured using ProteOn XPR36 system at 25° C. in Dulbecco's phosphate buffered saline containing 0.03% polysorbate P20 and 100 µg/ml bovine serum albumin;

c) inhibits CD154-mediated human B cell proliferation with an $IC_{50}$ value of about $2.7\times10^{-9}$ M or less; or d) inhibits CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1\times10^{-8}$M or less.

5. The antibody or antigen binding portion thereof of claim 1, wherein the human CD154 is a homotrimer and the antibody binds a first CD154 monomer in the homotrimer within amino acid residues 182-207 of CD154 and a second CD154 monomer in the homotrimer within amino acid residues 176-253 of CD154, wherein residue numbering is according to SEQ ID NO: 1.

6. The antibody or antigen binding portion thereof of claim 5, wherein the antibody binds residues E182, S185, Q186, A187, P188, S214, A215 and R207 in the first CD154 monomer, wherein residue numbering is according to SEQ ID NO: 1.

7. The antibody or antigen binding portion thereof of claim 5, wherein the antibody binds residues T176, F177, C178, Q220, S248, H249, G250 and F353 in the second CD154 monomer, wherein residue numbering is according to SEQ ID NO: 1.

8. The antibody or antigen binding portion thereof of claim 2, comprising a heavy chain variable region (VH) of SEQ ID NO: 59.

9. The antibody or antigen binding portion thereof of claim 8, comprising a light chain variable region (VL) of SEQ ID NOs: 65, 66, 67, 68, 69, 70, 71, 72 or 73.

10. The antibody or antigen binding portion thereof of claim 9, comprising the VL of SEQ ID NOs: 66, 72 or 73.

11. The antibody or antigen binding portion thereof of claim 10, comprising the VH of SEQ ID NO: 59 and the VL of SEQ ID NO: 66.

12. The antibody or antigen binding portion thereof of claim 10, comprising the VH of SEQ ID NO: 59 and the VL of SEQ ID NO: 72.

13. The antibody or antigen binding portion thereof of claim 10, comprising the VH of SEQ ID NO: 59 and the VL of SEQ ID NO: 73.

14. The antibody or antigen binding portion thereof of claim 1, wherein the antibody is of IgG1, IgG2, IgG3 or IgG4 isotype.

15. The antibody or antigen binding portion thereof of claim 14 comprising at least one substitution in an Fc region, wherein the at least one substitution in the Fc region is a substitution L234A, L235A, G237A, P238S, M252Y, S254T, T256E, H268A, A330S or P331S, wherein residue numbering is according to the EU Index.

16. The antibody or antigen binding portion thereof of claim 15, comprising substitutions L234A, L235A, G237A, P238S, H268A, A330S or P331S in the Fc region, wherein residue numbering is according to the EU Index.

17. The antibody or antigen binding portion thereof of claim 14 comprising at least one substitution in an Fc region, wherein the at least one substitution in the Fc region is a substitution V234A, G237A, P238S, M252Y, S254T, T256E, H268A, V309L, A330S or P331S, wherein residue numbering is according to the EU Index.

18. The antibody or antigen binding portion thereof of claim 17, comprising substitutions V234A, G237A, P238S, H268A, V309L, A330S and P331S in the Fc region, wherein residue numbering is according to the EU Index.

19. The antibody or antigen binding portion thereof of claim 14, comprising a heavy chain (HC) and a light chain (LC) of SEQ ID NOs:
a) 80 and 81, respectively;
b) 82 and 81, respectively; or
c) 83 and 81, respectively.

20. The antibody or antigen binding portion thereof of claim 1, wherein the antibody is multispecific.

21. An isolated antagonistic antibody or an antigen binding portion thereof specifically binding CD154 of SEQ ID NO: 1, comprising
a) the HCDR1, the HCDR2, the HCDR3, the LCDR1, the LCDR2 and the LCDR3 of SEQ ID NOs: 17, 23, 30, 37, 44 and 52, respectively;
b) the VH of SEQ ID NO: 59 and the VL of SEQ ID NO: 66; or
c) the heavy chain of SEQ ID NO: 80 and the light chain of SEQ ID NO: 81.

22. The antibody or antigen binding portion thereof of claim 1, wherein the human CD154 is a homotrimer and the antibody binds a first CD154 monomer in the homotrimer within amino acid residues 182-207 of CD154 and a second CD154 monomer in the homotrimer within amino acid residues 176-253 of CD154, wherein residue numbering is according to SEQ ID NO: 1.

23. An immunoconjugate comprising the antibody or antigen binding portion thereof of claim 1 linked to a therapeutic agent or an imaging agent.

24. A pharmaceutical composition comprising the antibody or antigen binding portion thereof of claim 1 and a pharmaceutically accepted carrier.

25. A method of inhibiting a biological activity of the human CD154 in a subject in need thereof comprising administering a therapeutically effective amount of the pharmaceutical composition of claim 24, to the subject, wherein the subject is in need of treatment of an autoimmune disease or an immune-mediated inflammatory disease.

26. The method of claim 25, wherein the immune-mediated inflammatory disease or the autoimmune disease is arthritis, systemic lupus erythematosus (SLE), inflammatory bowel disease, transplantation, kidney transplantation, skin transplantation, bone marrow transplantation, graft versus host disease (GVHD), immune thrombocytopenia (ITP), multiple sclerosis, thyroiditis, type I diabetes or atherosclerosis.

27. The method of claim 26 wherein the arthritis is rheumatoid arthritis, juvenile arthritis, psoriatic arthritis, Reiter's syndrome, ankylosing spondylitis, or gouty arthritis.

28. The method of claim 25, wherein the autoimmune disease or the immune-mediated inflammatory disease is lupus.

29. The method of claim 25, wherein the autoimmune disease or the immune-mediated inflammatory disease is transplantation.

30. The methods of claim 25, wherein the autoimmune disease or the immune-mediated inflammatory disease is inflammatory bowel disease (IBD).

31. The method of claim 30, wherein the IBD is Crohn's disease or ulcerative colitis.

32. The method of claim 25, further comprising administering to the subject a second therapeutic agent.

33. The method of claim 32, wherein the second therapeutic agent is selected from the group consisting of non-steroidal anti-inflammatory drugs (NSAIDs), salicylates, hydroxychloroquine, sulfasalazine, corticosteroids, cytotoxic drugs, immunosuppressive drugs and antibodies.

34. An isolated antagonistic antibody or an antigen binding portion thereof specifically binding CD154 of SEQ ID NO: 1, comprising an HCDR1, an HCDR2, an HCDR3, a LCDR1, a LCDR2, and a LCDR3 of
   a) SEQ ID NOs: 16, 22, 29, 36, 43 and 51, respectively;
   b) SEQ ID NOs: 17, 23, 30, 37, 44 and 52, respectively;
   c) SEQ ID NOs: 16, 24, 31, 38, 45 and 53, respectively;
   d) SEQ ID NOs: 18, 25, 32, 39, 46 and 54, respectively;
   e) SEQ ID NOs: 19, 26, 33, 40, 47 and 55, respectively;
   f) SEQ ID NOs: 20, 27, 34, 41, 47 and 56, respectively;
   g) SEQ ID NOs: 21, 28, 35, 42, 48 and 57, respectively;
   h) SEQ ID NOs: 17, 23, 30, 37, 49 and 52, respectively; or
   i) SEQ ID NOs: 17, 23, 30, 37, 50 and 52, respectively, wherein the HCDR1, the HCDR2, the HCDR3, the LCDR1, the LCDR2 and the LCDR3 are defined by Kabat, Chothia or IMGT.

35. The antibody or antigen binding portion thereof of claim 34, comprising
   a) the HCDR1, the HCDR2 and the HCDR3 of SEQ ID NOs: 16, 22 and 29, respectively, and the LCDR1, the LCDR2 and the LCDR3 of SEQ ID NOs: 36, 43 and 51, respectively; or
   b) the VH of SEQ ID NO: 58 and the VL of SEQ ID NO: 65.

36. The antibody or antigen binding portion thereof of claim 34, comprising
   a) the HCDR1, the HCDR2 and the HCDR3 of SEQ ID NOs: 17, 23 and 30, respectively, and the LCDR1, the LCDR2 and the LCDR3 of SEQ ID NOs: 37, 44 and 52, respectively; or
   b) the VH of SEQ ID NO: 59 and the VL of SEQ ID NO: 66.

37. The antibody or antigen binding portion thereof of claim 34, comprising
   a) the HCDR1, the HCDR2 and the HCDR3 of SEQ ID NOs: 16, 24 and 31, respectively, and the LCDR1, the LCDR2 and the LCDR3 of SEQ ID NOs: 38, 45 and 53, respectively; or
   b) the VH of SEQ ID NO: 60 and the VL of SEQ ID NO: 67.

38. The antibody or antigen binding portion thereof of claim 34, comprising
   a) the HCDR1, the HCDR2 and the HCDR3 of SEQ ID NOs: 18, 25 and 32, respectively, and the LCDR1, the LCDR2 and the LCDR3 of SEQ ID NOs: 39, 46 and 54, respectively; or
   b) the VH of SEQ ID NO: 61 and the VL of SEQ ID NO: 68.

39. The antibody or antigen binding portion thereof of claim 34, comprising
   a) the HCDR1, the HCDR2 and the HCDR3 of SEQ ID NOs: 19, 26 and 33, respectively, and LCDR1, the LCDR2 and the LCDR3 of SEQ ID NOs: 40, 47 and 55, respectively; or
   b) the VH of SEQ ID NO: 62 and the VL of SEQ ID NO: 69.

40. The antibody or antigen binding portion thereof of claim 34, comprising
   a) the HCDR1, the HCDR2 and the HCDR3 of SEQ ID NOs: 20, 27 and 34, respectively, and the LCDR1, the LCDR2 and the LCDR3 of SEQ ID NOs: 41, 47 and 56, respectively; or
   b) the VH of SEQ ID NO: 63 and the VL of SEQ ID NO: 70.

41. The antibody or antigen binding portion thereof of claim 34, comprising
   a) the HCDR1, the HCDR2 and the HCDR3 of SEQ ID NOs: 21, 28 and 35, respectively, and the LCDR1, the LCDR2 and the LCDR3 of SEQ ID NOs: 42, 48 and 57, respectively; or
   b) the VH of SEQ ID NO: 64 and the VL of SEQ ID NO: 71.

42. The antibody or antigen binding portion thereof of claim 34, comprising
   a) the HCDR1, the HCDR2 and the HCDR3 of SEQ ID NOs: 17, 23 and 30, respectively, and LCDR1, the LCDR2 and the LCDR3 of SEQ ID NOs: 37, 49 and 52, respectively; or
   b) the VH of SEQ ID NO: 59 and the VL of SEQ ID NO: 72.

43. The antibody or antigen binding portion thereof of claim 34, comprising
   a) the HCDR1, the HCDR2 and the HCDR3 of SEQ ID NOs: 17, 23 and 30, respectively, and the LCDR1, the LCDR2 and the LCDR3 of SEQ ID NOs: 37, 50 and 52, respectively; or
   b) the VH of SEQ ID NO: 59 and the VL of SEQ ID NO: 73.

44. The antibody or antigen binding portion thereof of claim 34, wherein the antibody is of IgG1, IgG2, IgG3 or IgG4 isotype.

45. The antibody or antigen binding portion thereof of claim 44 comprising at least one substitution in an Fc region, wherein the at least one substitution in the Fc region is a substitution L234A, L235A, G237A, P238S, M252Y, S254T, T256E, H268A, A330S or P331S, wherein residue numbering is according to the EU Index.

46. The antibody or antigen binding portion thereof of claim 45, comprising substitutions L234A, L235A, G237A, P238S, H268A, A330S and P331S in the Fc region, wherein residue numbering is according to the EU Index.

47. The antibody or antigen binding portion thereof of claim 44 comprising at least one substitution in an Fc region, wherein the at least one substitution in the Fc region is a substitution V234A, G237A, P238S, M252Y, S254T, T256E, H268A, V309L, A330S or P331S, wherein residue numbering is according to the EU Index.

48. The antibody or antigen binding portion thereof of claim 47, comprising substitutions V234A, G237A, P238S, H268A, V309L, A330S and P331S in the Fc region, wherein residue numbering is according to the EU Index.

49. The antibody or antigen binding portion thereof of claim 34, wherein the antibody is multispecific.

50. The antibody or antigen binding portion thereof of claim 34, wherein the antibody has at least one of the following properties:
   a) an immune complex of the antibody and soluble human CD154 (shCD154) does not activate platelets, wherein platelet activation is measured by P-selectin surface expression on platelets;
   b) binds to CD154 with a dissociation constant ($K_D$) of about $5\times10^{-9}$ M or less, when the $K_D$ is measured using ProteOn XPR36 system at 25° C. in Dulbecco's phosphate buffered saline containing 0.03% polysorbate P20 and 100 µg/ml bovine serum albumin;
   c) inhibits CD154-mediated human B cell proliferation with an $IC_{50}$ value of about $2.7\times10^{-9}$ M or less; or
   d) inhibits CD154-mediated expression of secreted embryonic alkaline phosphatase (SEAP) under NF-κB-inducible interferon-β (IFN-β) minimal promoter in HEK293 cells stably expressing SEAP and human CD40 with an $IC_{50}$ value of about $2.1 \times 10^{-8}$ M or less.

51. An immunoconjugate comprising the antibody or antigen binding portion thereof of claim 34 linked to a therapeutic agent or an imaging agent.

52. A pharmaceutical composition comprising the antibody or antigen binding portion thereof of claim 34 and a pharmaceutically accepted carrier.

53. A method of inhibiting a biological activity of the CD154 in a subject in need thereof, comprising administering a therapeutically effective amount of the pharmaceutical composition of claim 52 to the subject, wherein the subject is in need of treatment of an autoimmune disease or an immune-mediated inflammatory disease.

54. The method of claim 53, wherein the immune-mediated inflammatory disease or the autoimmune disease is arthritis, systemic lupus erythematosus (SLE), inflammatory bowel disease, transplantation, kidney transplantation, skin transplantation, bone marrow transplantation, graft versus host disease (GVHD), immune thrombocytopenia (ITP), multiple sclerosis, thyroiditis, type I diabetes or atherosclerosis.

55. The method of claim 54, wherein the arthritis is rheumatoid arthritis.

56. The method of claim 53, wherein the autoimmune disease or the immune-mediated inflammatory disease is lupus.

57. The method of claim 53, wherein the autoimmune disease or the immune-mediated inflammatory disease is transplantation.

58. The method of claim 53, wherein the autoimmune disease or the immune-mediated inflammatory disease is inflammatory bowel disease.

59. The method of claim 58, wherein the inflammatory bowel disease is Crohn's disease or ulcerative colitis.

60. The method of claim 53, further comprising administering to the subject a second therapeutic agent.

61. The method of claim 60, wherein the second therapeutic agent is selected from the group consisting of non-steroidal anti-inflammatory drugs (NSAIDs), salicylates, hydroxychloroquine, sulfasalazine, corticosteroids, cytotoxic drugs, immunosuppressive drugs and/or antibodies.

62. A kit comprising the antibody or antigen binding portion thereof of claim 1.

63. The kit of claim 62, further comprising reagents for detecting the antibody or antigen binding portion thereof.

64. An immunoconjugate comprising the antibody or antigen binding portion thereof of claim 21 linked to a therapeutic agent or an imaging agent.

65. A pharmaceutical composition comprising the antibody or antigen binding portion thereof of claim 21 and a pharmaceutically accepted carrier.

66. A method of inhibiting a biological activity of the CD154 in a subject in need thereof, comprising administering a therapeutically effective amount of the pharmaceutical composition of claim 65 to the subject, wherein the subject is in need of treatment of an autoimmune disease or an immune-mediated inflammatory disease.

* * * * *

UNITED STATES PATENT AND TRADEMARK OFFICE
CERTIFICATE OF CORRECTION

PATENT NO. : 10,669,343 B2
APPLICATION NO. : 15/228582
DATED : June 2, 2020
INVENTOR(S) : Johan Fransson et al.

Page 1 of 1

It is certified that error appears in the above-identified patent and that said Letters Patent is hereby corrected as shown below:

In the Claims

Claim 1, replace "16" with "I6" Column 123, Line 53.
Claim 1, replace "14" with "I4" Column 123, Line 47.
Claim 1, replace "L Q" with "L, Q" Column 123, Line 60.
Claim 1, replace "Si" with "S1" Column 123, Line 67.
Claim 2, replace "14" with "I4" Column 124, Line 30.
Claim 2, replace "L Q or E," with "L, Q or E;" Column 124, Line 33.
Claim 2, replace "Si" with "S1" Column 124, Line 40.

Signed and Sealed this
Third Day of November, 2020

Andrei Iancu
*Director of the United States Patent and Trademark Office*

SEQUENCE LISTING

<160> NUMBER OF SEQ ID NOS: 87

<210> SEQ ID NO 1
<211> LENGTH: 261
<212> TYPE: PRT
<213> ORGANISM: Homo sapiens

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

```
Val Thr Asp Pro Ser Gln Val Ser His Gly Thr Gly Phe Thr Ser Phe
                245                 250                 255

Gly Leu Leu Lys Leu
            260

<210> SEQ ID NO 2
<211> LENGTH: 261
<212> TYPE: PRT
<213> ORGANISM: Callithrix jacchus

<400> SEQUENCE: 2

Met Ile Glu Thr Tyr Asn Gln Pro Val Pro Arg Ser Ala Ala Thr Gly
1               5                   10                  15

Pro Pro Val Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Lys Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Pro Pro Asn Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Ile Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 261
<212> TYPE: PRT
<213> ORGANISM: Macaca fascicularis

<400> SEQUENCE: 3

Met Ile Glu Thr Tyr Asn Gln Pro Ser Pro Arg Ser Ala Ala Thr Gly
1               5                   10                  15

Leu Pro Val Arg Met Lys Ile Phe Met Tyr Leu Leu Thr Ile Phe Leu
                20                  25                  30
```

-continued

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
 50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Lys Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 4
<211> LENGTH: 149
<212> TYPE: PRT
<213> ORGANISM: Homo sapiens

<400> SEQUENCE: 4

Met Gln Lys Gly Asp Gln Asn Pro Gln Ile Ala Ala His Val Ile Ser
 1               5                  10                  15

Glu Ala Ser Ser Lys Thr Thr Ser Val Leu Gln Trp Ala Glu Lys Gly
                20                  25                  30

Tyr Tyr Thr Met Ser Asn Asn Leu Val Thr Leu Glu Asn Gly Lys Gln
            35                  40                  45

Leu Thr Val Lys Arg Gln Gly Leu Tyr Tyr Ile Tyr Ala Gln Val Thr
 50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                 85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe

```
                130                 135                 140
Gly Leu Leu Lys Leu
145

<210> SEQ ID NO 5
<211> LENGTH: 149
<212> TYPE: PRT
<213> ORGANISM: Callithrix jacchus

<400> SEQUENCE: 5

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Pro Asn Arg Phe Glu Arg Ile Leu Leu Arg Ala
                85                  90                  95

Ala Asn Thr His Ser Ser Ala Lys Pro Cys Gly Gln Gln Ser Ile His
                100                 105                 110

Leu Gly Gly Ile Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu
145

<210> SEQ ID NO 6
<211> LENGTH: 149
<212> TYPE: PRT
<213> ORGANISM: Macaca fascicularis

<400> SEQUENCE: 6

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
                100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu
```

<210> SEQ ID NO 7
<211> LENGTH: 161
<212> TYPE: PRT
<213> ORGANISM: Artificial Sequence
<220> FEATURE:
<223> OTHER INFORMATION: Fusion protein shCD154-Histag

<400> SEQUENCE: 7

```
Gly Ser His His His His His Gly Gly Gly Ser Met Gln Lys Gly
1               5                   10                  15

Asp Gln Asn Pro Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys
    50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Cys Leu Lys
                85                  90                  95

Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
        115                 120                 125

Phe Glu Leu Gln Pro Gly Ala Ser Val Phe Val Asn Val Thr Asp Pro
    130                 135                 140

Ser Gln Val Ser His Gly Thr Gly Phe Thr Ser Phe Gly Leu Leu Lys
145                 150                 155                 160

Leu
```

<210> SEQ ID NO 8
<211> LENGTH: 161
<212> TYPE: PRT
<213> ORGANISM: Artificial Sequence
<220> FEATURE:
<223> OTHER INFORMATION: Fusion protein smCD154-histag

<400> SEQUENCE: 8

```
Gly Ser His His His His His Gly Gly Gly Ser Met Gln Lys Gly
1               5                   10                  15

Asp Gln Asn Pro Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys
    50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Cys Leu Lys
                85                  90                  95

Pro Pro Asn Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Ile
        115                 120                 125

Phe Glu Leu Gln Pro Gly Ala Ser Val Phe Val Asn Val Thr Asp Pro
```

```
                130                 135                 140
Ser Gln Val Ser His Gly Thr Gly Phe Thr Ser Phe Gly Leu Leu Lys
145                 150                 155                 160

Leu

<210> SEQ ID NO 9
<211> LENGTH: 161
<212> TYPE: PRT
<213> ORGANISM: Artificial Sequence
<220> FEATURE:
<223> OTHER INFORMATION: Fusion protein scCD154-histag

<400> SEQUENCE: 9

Gly Ser His His His His His His Gly Gly Gly Ser Met Gln Lys Gly
1               5                   10                  15

Asp Gln Asn Pro Gln Ile Ala Ala His Val Ile Ser Glu Ala Ser Ser
                20                  25                  30

Lys Thr Thr Ser Val Leu Gln Trp Ala Glu Lys Gly Tyr Tyr Thr Met
            35                  40                  45

Ser Asn Asn Leu Val Thr Leu Glu Asn Gly Lys Gln Leu Thr Val Lys
        50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Cys Leu Lys
                85                  90                  95

Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
        115                 120                 125

Phe Glu Leu Gln Pro Gly Ala Ser Val Phe Val Asn Val Thr Asp Pro
    130                 135                 140

Ser Gln Val Ser His Gly Thr Gly Phe Thr Ser Phe Gly Leu Leu Lys
145                 150                 155                 160

Leu

<210> SEQ ID NO 10
<211> LENGTH: 6
<212> TYPE: PRT
<213> ORGANISM: Artificial Sequence
<220> FEATURE:
<223> OTHER INFORMATION: His6 tag

<400> SEQUENCE: 10

His His His His His His
1               5

<210> SEQ ID NO 11
<211> LENGTH: 33
<212> TYPE: PRT
<213> ORGANISM: Artificial Sequence
<220> FEATURE:
<223> OTHER INFORMATION: ILZ tag

<400> SEQUENCE: 11

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg
```

<210> SEQ ID NO 12
<211> LENGTH: 198
<212> TYPE: PRT
<213> ORGANISM: Artificial Sequence
<220> FEATURE:
<223> OTHER INFORMATION: Fusion protein shCD154-ILZ

<400> SEQUENCE: 12

Gly Ser His His His His His Gly Gly Gly Ser Arg Met Lys Gln
1               5                   10                  15

Ile Glu Asp Lys Ile Glu Glu Ile Leu Ser Lys Ile Tyr His Ile Glu
            20                  25                  30

Asn Glu Ile Ala Arg Ile Lys Lys Leu Ile Gly Glu Arg Gly Gly Gly
        35                  40                  45

Ser Met Gln Lys Gly Asp Gln Asn Pro Gln Ile Ala Ala His Val Ile
    50                  55                  60

Ser Glu Ala Ser Ser Lys Thr Thr Ser Val Leu Gln Trp Ala Glu Lys
65                  70                  75                  80

Gly Tyr Tyr Thr Met Ser Asn Asn Leu Val Thr Leu Glu Asn Gly Lys
                85                  90                  95

Gln Leu Thr Val Lys Arg Gln Gly Leu Tyr Tyr Ile Tyr Ala Gln Val
            100                 105                 110

Thr Phe Cys Ser Asn Arg Glu Ala Ser Ser Gln Ala Pro Phe Ile Ala
        115                 120                 125

Ser Leu Cys Leu Lys Ser Pro Gly Arg Phe Glu Arg Ile Leu Leu Arg
    130                 135                 140

Ala Ala Asn Thr His Ser Ser Ala Lys Pro Cys Gly Gln Gln Ser Ile
145                 150                 155                 160

His Leu Gly Gly Val Phe Glu Leu Gln Pro Gly Ala Ser Val Phe Val
                165                 170                 175

Asn Val Thr Asp Pro Ser Gln Val Ser His Gly Thr Gly Phe Thr Ser
            180                 185                 190

Phe Gly Leu Leu Lys Leu
        195

<210> SEQ ID NO 13
<211> LENGTH: 198
<212> TYPE: PRT
<213> ORGANISM: Artificial Sequence
<220> FEATURE:
<223> OTHER INFORMATION: Fusion protein smCD154-ILZ

<400> SEQUENCE: 13

Gly Ser His His His His His Gly Gly Gly Ser Arg Met Lys Gln
1               5                   10                  15

Ile Glu Asp Lys Ile Glu Glu Ile Leu Ser Lys Ile Tyr His Ile Glu
            20                  25                  30

Asn Glu Ile Ala Arg Ile Lys Lys Leu Ile Gly Glu Arg Gly Gly Gly
        35                  40                  45

Ser Met Gln Lys Gly Asp Gln Asn Pro Gln Ile Ala Ala His Val Ile
    50                  55                  60

Ser Glu Ala Ser Ser Lys Thr Thr Ser Val Leu Gln Trp Ala Glu Lys
65                  70                  75                  80

Gly Tyr Tyr Thr Met Ser Asn Asn Leu Val Thr Leu Glu Asn Gly Lys
                85                  90                  95

Gln Leu Thr Val Lys Arg Gln Gly Leu Tyr Tyr Ile Tyr Ala Gln Val

```
                     100                 105                 110
Thr Phe Cys Ser Asn Arg Glu Ala Ser Ser Gln Ala Pro Phe Ile Ala
            115                 120                 125

Ser Leu Cys Leu Lys Pro Pro Asn Arg Phe Glu Arg Ile Leu Leu Arg
        130                 135                 140

Ala Ala Asn Thr His Ser Ser Ala Lys Pro Cys Gly Gln Gln Ser Ile
145                 150                 155                 160

His Leu Gly Gly Ile Phe Glu Leu Gln Pro Gly Ala Ser Val Phe Val
                165                 170                 175

Asn Val Thr Asp Pro Ser Gln Val Ser His Gly Thr Gly Phe Thr Ser
            180                 185                 190

Phe Gly Leu Leu Lys Leu
        195

<210> SEQ ID NO 14
<211> LENGTH: 198
<212> TYPE: PRT
<213> ORGANISM: Artificial Sequence
<220> FEATURE:
<223> OTHER INFORMATION: Fusion protein scCD154-ILZ

<400> SEQUENCE: 14

Gly Ser His His His His His Gly Gly Gly Ser Arg Met Lys Gln
1               5                   10                  15

Ile Glu Asp Lys Ile Glu Glu Ile Leu Ser Lys Ile Tyr His Ile Glu
            20                  25                  30

Asn Glu Ile Ala Arg Ile Lys Lys Leu Ile Gly Glu Arg Gly Gly Gly
        35                  40                  45

Ser Met Gln Lys Gly Asp Gln Asn Pro Gln Ile Ala Ala His Val Ile
    50                  55                  60

Ser Glu Ala Ser Ser Lys Thr Thr Ser Val Leu Gln Trp Ala Glu Lys
65                  70                  75                  80

Gly Tyr Tyr Thr Met Ser Asn Asn Leu Val Thr Leu Glu Asn Gly Lys
                85                  90                  95

Gln Leu Thr Val Lys Arg Gln Gly Leu Tyr Tyr Ile Tyr Ala Gln Val
            100                 105                 110

Thr Phe Cys Ser Asn Arg Glu Ala Ser Ser Gln Ala Pro Phe Ile Ala
        115                 120                 125

Ser Leu Cys Leu Lys Ser Pro Gly Arg Phe Glu Arg Ile Leu Leu Arg
    130                 135                 140

Ala Ala Asn Thr His Ser Ser Ala Lys Pro Cys Gly Gln Gln Ser Ile
145                 150                 155                 160

His Leu Gly Gly Val Phe Glu Leu Gln Pro Gly Ala Ser Val Phe Val
                165                 170                 175

Asn Val Thr Asp Pro Ser Gln Val Ser His Gly Thr Gly Phe Thr Ser
            180                 185                 190

Phe Gly Leu Leu Lys Leu
        195

<210> SEQ ID NO 15
<211> LENGTH: 277
<212> TYPE: PRT
<213> ORGANISM: Homo sapiens

<400> SEQUENCE: 15

Met Val Arg Leu Pro Leu Gln Cys Val Leu Trp Gly Cys Leu Leu Thr
1               5                   10                  15
```

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
50                      55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 16
<211> LENGTH: 5
<212> TYPE: PRT
<213> ORGANISM: Artificial Sequence
<220> FEATURE:
<223> OTHER INFORMATION: HCDR1

<400> SEQUENCE: 16

Ser Tyr Ala Ile Ser
1               5

<210> SEQ ID NO 17
<211> LENGTH: 5
<212> TYPE: PRT
<213> ORGANISM: Artificial Sequence
<220> FEATURE:
<223> OTHER INFORMATION: HCDR1

<400> SEQUENCE: 17

Ser Tyr Gly Ile Ser
1               5

```
<210> SEQ ID NO 18
<211> LENGTH: 7
<212> TYPE: PRT
<213> ORGANISM: Artificial Sequence
<220> FEATURE:
<223> OTHER INFORMATION: HCDR1

<400> SEQUENCE: 18

Ser Tyr Ser Phe Tyr Trp Gly
1               5

<210> SEQ ID NO 19
<211> LENGTH: 5
<212> TYPE: PRT
<213> ORGANISM: Artificial Sequence
<220> FEATURE:
<223> OTHER INFORMATION: HCDR1

<400> SEQUENCE: 19

Ala Tyr Tyr Ile His
1               5

<210> SEQ ID NO 20
<211> LENGTH: 5
<212> TYPE: PRT
<213> ORGANISM: Artificial Sequence
<220> FEATURE:
<223> OTHER INFORMATION: HCDR1

<400> SEQUENCE: 20

Asp Tyr Tyr Ile His
1               5

<210> SEQ ID NO 21
<211> LENGTH: 7
<212> TYPE: PRT
<213> ORGANISM: Artificial Sequence
<220> FEATURE:
<223> OTHER INFORMATION: HCDR1

<400> SEQUENCE: 21

Ser Phe Ile Tyr Tyr Trp Gly
1               5

<210> SEQ ID NO 22
<211> LENGTH: 17
<212> TYPE: PRT
<213> ORGANISM: Artificial Sequence
<220> FEATURE:
<223> OTHER INFORMATION: HCDR2

<400> SEQUENCE: 22

Gly Ile Ile Pro Ile Phe Gly Thr Ala Asn Tyr Ala Gln Lys Phe Gln
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: HCDR2

<400> SEQUENCE: 23

Trp Ile Ser Pro Ile Phe Gly Asn Thr Asn Tyr Ala Gln Lys Phe Gln
1               5                   10                  15
```

Gly

<210> SEQ ID NO 24
<211> LENGTH: 17
<212> TYPE: PRT
<213> ORGANISM: Artificial Sequence
<220> FEATURE:
<223> OTHER INFORMATION: HCDR2

<400> SEQUENCE: 24

Gly Ile Ser Pro Tyr Phe Gly Asn Thr Asn Tyr Ala Gln Lys Phe Gln
1               5                   10                  15

Gly

<210> SEQ ID NO 25
<211> LENGTH: 16
<212> TYPE: PRT
<213> ORGANISM: Artificial Sequence
<220> FEATURE:
<223> OTHER INFORMATION: HCDR2

<400> SEQUENCE: 25

Ser Leu Tyr Tyr Ser Gly Ser Thr Tyr Tyr Asn Pro Ser Leu Lys Ser
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: HCDR2

<400> SEQUENCE: 26

Arg Ile Asn Pro Asp Ser Gly Gly Thr Asp Tyr Ala Gln Arg Phe Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: HCDR2

<400> SEQUENCE: 27

Arg Phe Asn Pro Asn Ser Gly Asp Thr Asn Gly Ala Gln Lys Phe Gln
1               5                   10                  15

Gly

<210> SEQ ID NO 28
<211> LENGTH: 16
<212> TYPE: PRT
<213> ORGANISM: Artificial Sequence
<220> FEATURE:
<223> OTHER INFORMATION: HCDR2

<400> SEQUENCE: 28

Cys Ile Tyr Ser Ser Gly Gly Thr Tyr Tyr Asn Pro Ser Leu Lys Ser
1               5                   10                  15

<210> SEQ ID NO 29
<211> LENGTH: 14
<212> TYPE: PRT
<213> ORGANISM: Artificial Sequence
<220> FEATURE:

```
<223> OTHER INFORMATION: HCDR3

<400> SEQUENCE: 29

Gly Ala Ser Val Trp Asp Gly Pro Ala Glu Val Phe Asp Tyr
1               5                   10

<210> SEQ ID NO 30
<211> LENGTH: 9
<212> TYPE: PRT
<213> ORGANISM: Artificial Sequence
<220> FEATURE:
<223> OTHER INFORMATION: HCDR3

<400> SEQUENCE: 30

Ser Arg Tyr Tyr Gly Asp Leu Asp Tyr
1               5

<210> SEQ ID NO 31
<211> LENGTH: 12
<212> TYPE: PRT
<213> ORGANISM: Artificial Sequence
<220> FEATURE:
<223> OTHER INFORMATION: HCDR3

<400> SEQUENCE: 31

Asp Thr Gly Trp Val Gly Ala Phe Tyr Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: HCDR3

<400> SEQUENCE: 32

Leu Gln Leu Gly Thr Thr Thr Asp Tyr Phe Asp His
1               5                   10

<210> SEQ ID NO 33
<211> LENGTH: 20
<212> TYPE: PRT
<213> ORGANISM: Artificial Sequence
<220> FEATURE:
<223> OTHER INFORMATION: HCDR3

<400> SEQUENCE: 33

Asp Trp Asn Tyr Tyr Asp Gly Ser Gly Tyr Phe Gly Pro Gly Tyr Tyr
1               5                   10                  15

Gly Leu Asp Val
            20

<210> SEQ ID NO 34
<211> LENGTH: 11
<212> TYPE: PRT
<213> ORGANISM: Artificial Sequence
<220> FEATURE:
<223> OTHER INFORMATION: HCDR3

<400> SEQUENCE: 34

Glu Gly Glu Leu Ala Gly Ile Phe Phe Asp Tyr
1               5                   10

<210> SEQ ID NO 35
<211> LENGTH: 12
<212> TYPE: PRT
```

<213> ORGANISM: Artificial Sequence
<220> FEATURE:
<223> OTHER INFORMATION: HCDR3

<400> SEQUENCE: 35

Leu Trp Leu Gly Thr Thr Thr Asp Tyr Phe Asp Tyr
1               5                   10

<210> SEQ ID NO 36
<211> LENGTH: 17
<212> TYPE: PRT
<213> ORGANISM: Artificial Sequence
<220> FEATURE:
<223> OTHER INFORMATION: LCDR1

<400> SEQUENCE: 36

Lys Ser Ser Gln Ser Val Leu Ala Ser Ser Asn Asn Glu Asn Phe Leu
1               5                   10                  15

Ala

<210> SEQ ID NO 37
<211> LENGTH: 11
<212> TYPE: PRT
<213> ORGANISM: Artificial Sequence
<220> FEATURE:
<223> OTHER INFORMATION: LCDR1

<400> SEQUENCE: 37

Arg Ala Ser Gln Ser Ile Ser Ser Tyr Leu Asn
1               5                   10

<210> SEQ ID NO 38
<211> LENGTH: 17
<212> TYPE: PRT
<213> ORGANISM: Artificial Sequence
<220> FEATURE:
<223> OTHER INFORMATION: LCDR1

<400> SEQUENCE: 38

Lys Ser Ser Gln Ser Val Leu Tyr Ser Ser Asn Asn Lys Asn Tyr Leu
1               5                   10                  15

Ala

<210> SEQ ID NO 39
<211> LENGTH: 11
<212> TYPE: PRT
<213> ORGANISM: Artificial Sequence
<220> FEATURE:
<223> OTHER INFORMATION: LCDR1

<400> SEQUENCE: 39

Ser Gly Asp Glu Leu Gly Asp Lys Phe Ala Cys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: LCDR1

<400> SEQUENCE: 40

Ser Gly Asp Lys Leu Gly Asp Lys Tyr Val Cys
1               5                   10

```
<210> SEQ ID NO 41
<211> LENGTH: 11
<212> TYPE: PRT
<213> ORGANISM: Artificial Sequence
<220> FEATURE:
<223> OTHER INFORMATION: LCDR1

<400> SEQUENCE: 41

Ser Gly Asp Lys Leu Gly Asp Lys Tyr Val Ser
1               5                   10

<210> SEQ ID NO 42
<211> LENGTH: 11
<212> TYPE: PRT
<213> ORGANISM: Artificial Sequence
<220> FEATURE:
<223> OTHER INFORMATION: LCDR1

<400> SEQUENCE: 42

Ser Gly Asp Lys Leu Gly Asp Lys Phe Ala Cys
1               5                   10

<210> SEQ ID NO 43
<211> LENGTH: 7
<212> TYPE: PRT
<213> ORGANISM: Artificial Sequence
<220> FEATURE:
<223> OTHER INFORMATION: LCDR2

<400> SEQUENCE: 43

Ser Ala Ser Thr Arg Glu Ser
1               5

<210> SEQ ID NO 44
<211> LENGTH: 7
<212> TYPE: PRT
<213> ORGANISM: Artificial Sequence
<220> FEATURE:
<223> OTHER INFORMATION: LCDR2

<400> SEQUENCE: 44

Tyr Ala Asn Ser Leu Gln Ser
1               5

<210> SEQ ID NO 45
<211> LENGTH: 7
<212> TYPE: PRT
<213> ORGANISM: Artificial Sequence
<220> FEATURE:
<223> OTHER INFORMATION: LCDR2

<400> SEQUENCE: 45

Trp Ala Ser Thr Arg Glu Ser
1               5

<210> SEQ ID NO 46
<211> LENGTH: 7
<212> TYPE: PRT
<213> ORGANISM: Artificial Sequence
<220> FEATURE:
<223> OTHER INFORMATION: LCDR2

<400> SEQUENCE: 46

Gln Glu Asn Lys Arg Pro Ser
1               5

<210> SEQ ID NO 47
```

```
<211> LENGTH: 7
<212> TYPE: PRT
<213> ORGANISM: Artificial Sequence
<220> FEATURE:
<223> OTHER INFORMATION: LCDR2

<400> SEQUENCE: 47

Gln Asp Arg Lys Arg Pro Ser
1               5

<210> SEQ ID NO 48
<211> LENGTH: 7
<212> TYPE: PRT
<213> ORGANISM: Artificial Sequence
<220> FEATURE:
<223> OTHER INFORMATION: LCDR2

<400> SEQUENCE: 48

Gln Asp Asp Lys Arg Pro Ser
1               5

<210> SEQ ID NO 49
<211> LENGTH: 7
<212> TYPE: PRT
<213> ORGANISM: Artificial Sequence
<220> FEATURE:
<223> OTHER INFORMATION: LCDR2

<400> SEQUENCE: 49

Tyr Ala Ser Ser Leu Gln Ser
1               5

<210> SEQ ID NO 50
<211> LENGTH: 7
<212> TYPE: PRT
<213> ORGANISM: Artificial Sequence
<220> FEATURE:
<223> OTHER INFORMATION: LCDR2

<400> SEQUENCE: 50

Tyr Ala Asn Thr Leu Gln Ser
1               5

<210> SEQ ID NO 51
<211> LENGTH: 9
<212> TYPE: PRT
<213> ORGANISM: Artificial Sequence
<220> FEATURE:
<223> OTHER INFORMATION: LCDR3

<400> SEQUENCE: 51

Gln Gln Ala Tyr Thr Thr Pro Phe Thr
1               5

<210> SEQ ID NO 52
<211> LENGTH: 9
<212> TYPE: PRT
<213> ORGANISM: Artificial Sequence
<220> FEATURE:
<223> OTHER INFORMATION: LCDR3

<400> SEQUENCE: 52

Gln Gln Ser Asp Ser Ile Pro Trp Thr
1               5

<210> SEQ ID NO 53
<211> LENGTH: 9
```

```
<212> TYPE: PRT
<213> ORGANISM: Artificial Sequence
<220> FEATURE:
<223> OTHER INFORMATION: LCDR3

<400> SEQUENCE: 53

Gln Gln Tyr Tyr Ser Thr Pro Leu Thr
1               5

<210> SEQ ID NO 54
<211> LENGTH: 9
<212> TYPE: PRT
<213> ORGANISM: Artificial Sequence
<220> FEATURE:
<223> OTHER INFORMATION: LCDR3

<400> SEQUENCE: 54

Gln Ala Trp Asp Ser Asp Thr Ala Val
1               5

<210> SEQ ID NO 55
<211> LENGTH: 9
<212> TYPE: PRT
<213> ORGANISM: Artificial Sequence
<220> FEATURE:
<223> OTHER INFORMATION: LCDR3

<400> SEQUENCE: 55

Gln Ala Trp Asp Ser Gly Thr Val Val
1               5

<210> SEQ ID NO 56
<211> LENGTH: 9
<212> TYPE: PRT
<213> ORGANISM: Artificial Sequence
<220> FEATURE:
<223> OTHER INFORMATION: LCDR3

<400> SEQUENCE: 56

Gln Ala Trp Asp Ser Ser Thr Val Val
1               5

<210> SEQ ID NO 57
<211> LENGTH: 9
<212> TYPE: PRT
<213> ORGANISM: Artificial Sequence
<220> FEATURE:
<223> OTHER INFORMATION: LCDR3

<400> SEQUENCE: 57

Gln Ala Trp Asp Ser Asn Thr Val Val
1               5

<210> SEQ ID NO 58
<211> LENGTH: 123
<212> TYPE: PRT
<213> ORGANISM: Artificial Sequence
<220> FEATURE:
<223> OTHER INFORMATION: VH of C4LB5

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ala Ser Val Trp Asp Gly Pro Ala Glu Val Phe Asp Tyr
            100                 105                 110

Trp Gly Gln Gly Thr Leu Val Thr Val Ser Ser
            115                 120
```

<210> SEQ ID NO 59
<211> LENGTH: 118
<212> TYPE: PRT
<213> ORGANISM: Artificial Sequence
<220> FEATURE:
<223> OTHER INFORMATION: VH of C4LB89

<400> SEQUENCE: 59

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Gly Ile Ser Trp Val Arg Gln Ala Pro Gly Gln Gly Leu Glu Trp Met
             35                  40                  45

Gly Trp Ile Ser Pro Ile Phe Gly Asn Thr Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Tyr Tyr Gly Asp Leu Asp Tyr Trp Gly Gln Gly Thr
            100                 105                 110

Leu Val Thr Val Ser Ser
            115
```

<210> SEQ ID NO 60
<211> LENGTH: 121
<212> TYPE: PRT
<213> ORGANISM: Artificial Sequence
<220> FEATURE:
<223> OTHER INFORMATION: VH of C4LB94

<400> SEQUENCE: 60

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ser Pro Tyr Phe Gly Asn Thr Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Asp Thr Gly Trp Val Gly Ala Phe Tyr Leu Asp Tyr Trp Gly
            100                 105                 110

Gln Gly Thr Leu Val Thr Val Ser Ser
        115                 120

<210> SEQ ID NO 61
<211> LENGTH: 122
<212> TYPE: PRT
<213> ORGANISM: Artificial Sequence
<220> FEATURE:
<223> OTHER INFORMATION: VH of C4LB150

<400> SEQUENCE: 61

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ser Phe Tyr Trp Gly Trp Ile Arg Gln Pro Pro Gly Gln Gly Leu Glu
        35                  40                  45

Trp Ile Gly Ser Leu Tyr Tyr Ser Gly Ser Thr Tyr Tyr Asn Pro Ser
    50                  55                  60

Leu Lys Ser Arg Ala Thr Met Ser Val Val Thr Ser Lys Thr Gln Phe
65                  70                  75                  80

Ser Leu Asn Leu Asn Ser Val Thr Ala Ala Asp Thr Ala Val Tyr Tyr
                85                  90                  95

Cys Ala Arg Leu Gln Leu Gly Thr Thr Thr Asp Tyr Phe Asp His Trp
            100                 105                 110

Gly Gln Gly Thr Leu Val Thr Val Ser Ser
        115                 120

<210> SEQ ID NO 62
<211> LENGTH: 129
<212> TYPE: PRT
<213> ORGANISM: Artificial Sequence
<220> FEATURE:
<223> OTHER INFORMATION: VH of C4LB189

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ala Tyr
            20                  25                  30

Tyr Ile His Trp Val Arg Gln Ala Pro Gly Gln Gly Leu Glu Trp Met
        35                  40                  45

Gly Arg Ile Asn Pro Asp Ser Gly Gly Thr Asp Tyr Ala Gln Arg Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Phe Tyr Cys
                85                  90                  95

Ala Arg Asp Trp Asn Tyr Tyr Asp Gly Ser Gly Tyr Phe Gly Pro Gly
            100                 105                 110

Tyr Tyr Gly Leu Asp Val Trp Gly Gln Gly Thr Thr Val Thr Val Ser
        115                 120                 125

Ser

<210> SEQ ID NO 63
<211> LENGTH: 120

```
<212> TYPE: PRT
<213> ORGANISM: Artificial Sequence
<220> FEATURE:
<223> OTHER INFORMATION: VH of C4LB191

<400> SEQUENCE: 63
```

Gln Val Gln Leu Val Gln Ser Gly Ala Glu Val Lys Lys Pro Gly Ala
1               5                   10                  15

Ser Met Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Val
            35                  40                  45

Gly Arg Phe Asn Pro Asn Ser Gly Asp Thr Asn Gly Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Thr Arg Leu Arg Ser Asp Asp Thr Ala Val Tyr His Cys
                85                  90                  95

Ala Arg Glu Gly Glu Leu Ala Gly Ile Phe Phe Asp Tyr Trp Gly Gln
                100                 105                 110

Gly Thr Leu Val Thr Val Ser Ser
            115                 120

```
<210> SEQ ID NO 64
<211> LENGTH: 122
<212> TYPE: PRT
<213> ORGANISM: Artificial Sequence
<220> FEATURE:
<223> OTHER INFORMATION: VH of C4LB199

<400> SEQUENCE: 64
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Phe
                20                  25                  30

Ile Tyr Tyr Trp Gly Trp Ile Arg Gln Pro Pro Gly Lys Gly Leu Asp
            35                  40                  45

Trp Val Gly Cys Ile Tyr Ser Ser Gly Gly Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Pro Ser Val Thr Ala Ala Asp Thr Ala Val Tyr Tyr
                85                  90                  95

Cys Ala Arg Leu Trp Leu Gly Thr Thr Thr Asp Tyr Phe Asp Tyr Trp
                100                 105                 110

Gly Gln Gly Thr Leu Val Thr Val Ser Ser
            115                 120

```
<210> SEQ ID NO 65
<211> LENGTH: 113
<212> TYPE: PRT
<213> ORGANISM: Artificial Sequence
<220> FEATURE:
<223> OTHER INFORMATION: VL of C4LB5

<400> SEQUENCE: 65
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ala Ser

```
                20                  25                  30
Ser Asn Asn Glu Asn Phe Leu Ala Trp Tyr Gln Gln Lys Pro Gly Gln
            35                  40                  45

Pro Pro Lys Leu Leu Ile Tyr Ser Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ala Tyr Thr Thr Pro Phe Thr Phe Gly Gln Gly Thr Lys Val Glu Ile
            100                 105                 110

Lys

<210> SEQ ID NO 66
<211> LENGTH: 107
<212> TYPE: PRT
<213> ORGANISM: Artificial Sequence
<220> FEATURE:
<223> OTHER INFORMATION: VL of C4LB89

<400> SEQUENCE: 66

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Ala Asn Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asp Ser Ile Pro Trp
                85                  90                  95

Thr Phe Gly Gln Gly Thr Lys Val Glu Ile Lys
            100                 105

<210> SEQ ID NO 67
<211> LENGTH: 113
<212> TYPE: PRT
<213> ORGANISM: Artificial Sequence
<220> FEATURE:
<223> OTHER INFORMATION: VL of C4LB94

<400> SEQUENCE: 67

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
```

Lys

<210> SEQ ID NO 68
<211> LENGTH: 106
<212> TYPE: PRT
<213> ORGANISM: Artificial Sequence
<220> FEATURE:
<223> OTHER INFORMATION: VL of C4LB150

<400> SEQUENCE: 68

Ser Tyr Glu Leu Thr Gln Pro Pro Ser Val Ser Val Ser Pro Gly Gln
1               5                   10                  15

Thr Ala Ser Ile Thr Cys Ser Gly Asp Glu Leu Gly Asp Lys Phe Ala
            20                  25                  30

Cys Trp Tyr Gln Gln Lys Pro Gly Gln Ser Pro Val Leu Val Ile Trp
        35                  40                  45

Gln Glu Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asp Thr Ala Val
                85                  90                  95

Phe Gly Gly Gly Thr Lys Leu Thr Val Leu
            100                 105

<210> SEQ ID NO 69
<211> LENGTH: 106
<212> TYPE: PRT
<213> ORGANISM: Artificial Sequence
<220> FEATURE:
<223> OTHER INFORMATION: VL of C4LB189

<400> SEQUENCE: 69

Ser Tyr Glu Leu Thr Gln Pro Pro Ser Val Ser Val Ser Pro Gly Gln
1               5                   10                  15

Thr Ala Ser Val Thr Cys Ser Gly Asp Lys Leu Gly Asp Lys Tyr Val
            20                  25                  30

Cys Trp Tyr Gln Arg Lys Pro Gly Gln Ser Pro Val Leu Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Ile
65                  70                  75                  80

Asp Glu Ala Asp Tyr Tyr Cys Gln Ala Trp Asp Ser Gly Thr Val Val
                85                  90                  95

Phe Gly Arg Gly Thr Lys Leu Thr Val Leu
            100                 105

<210> SEQ ID NO 70
<211> LENGTH: 106
<212> TYPE: PRT
<213> ORGANISM: Artificial Sequence
<220> FEATURE:
<223> OTHER INFORMATION: VL of C4LB191

<400> SEQUENCE: 70

Ser Tyr Glu Leu Thr Gln Pro Pro Ser Val Ser Val Ser Pro Gly Gln
1               5                   10                  15

```
Thr Ala Ser Ile Thr Cys Ser Gly Asp Lys Leu Gly Asp Lys Tyr Val
            20                  25                  30

Ser Trp Asn His Gln Lys Pro Gly Gln Ser Pro Val Leu Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Thr Val Val
                85                  90                  95

Phe Gly Gly Gly Thr Lys Leu Thr Val Leu
            100                 105

<210> SEQ ID NO 71
<211> LENGTH: 106
<212> TYPE: PRT
<213> ORGANISM: Artificial Sequence
<220> FEATURE:
<223> OTHER INFORMATION: VL of C4LB199

<400> SEQUENCE: 71

Ser Tyr Glu Leu Thr Gln Pro Pro Ser Val Ser Val Ser Pro Gly Gln
1               5                   10                  15

Thr Val Ser Ile Thr Cys Ser Gly Asp Lys Leu Gly Asp Lys Phe Ala
            20                  25                  30

Cys Trp Tyr Gln Gln Lys Pro Gly Gln Ser Pro Val Val Val Ile Tyr
        35                  40                  45

Gln Asp Asp Lys Arg Pro Ser Gly Ile Pro Glu Arg Phe Ser Gly Ser
    50                  55                  60

Thr Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Val Val
                85                  90                  95

Phe Gly Gly Gly Thr Lys Leu Thr Val Leu
            100                 105

<210> SEQ ID NO 72
<211> LENGTH: 107
<212> TYPE: PRT
<213> ORGANISM: Artificial Sequence
<220> FEATURE:
<223> OTHER INFORMATION: VL or C4LB235

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ile Pro Trp
                85                  90                  95

Thr Phe Gly Gln Gly Thr Lys Val Glu Ile Lys
            100                 105
```

<210> SEQ ID NO 73
<211> LENGTH: 107
<212> TYPE: PRT
<213> ORGANISM: Artificial Sequence
<220> FEATURE:
<223> OTHER INFORMATION: VL of C4LB236

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Asn Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ile Pro Trp
                85                  90                  95

Thr Phe Gly Gln Gly Thr Lys Val Glu Ile Lys
            100                 105

<210> SEQ ID NO 74
<211> LENGTH: 118
<212> TYPE: PRT
<213> ORGANISM: Artificial Sequence
<220> FEATURE:
<223> OTHER INFORMATION: VH of 5c8

<400> SEQUENCE: 74

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 75
<211> LENGTH: 111
<212> TYPE: PRT
<213> ORGANISM: Artificial Sequence
<220> FEATURE:
<223> OTHER INFORMATION: VL of 5c8

<400> SEQUENCE: 75

Asp Ile Val Leu Thr Gln Ser Pro Ala Thr Leu Ser Val Ser Pro Gly
1               5                   10                  15

```
Glu Arg Ala Thr Ile Ser Cys Arg Ala Ser Gln Arg Val Ser Ser Ser
                20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
                100                 105                 110
```

<210> SEQ ID NO 76
<211> LENGTH: 321
<212> TYPE: DNA
<213> ORGANISM: Artificial Sequence
<220> FEATURE:
<223> OTHER INFORMATION: cDNA of VH of C4LB231

<400> SEQUENCE: 76

```
gacatccaga tgacccagag ccccagcagc ctgagcgcca gcgtgggcga cagagtgacc    60
atcacctgtc gggccagcca gagcatcagc agctacctga actggtatca gcagaagccc   120
ggcaaggccc ccaagctgct gatctactac gccaacagcc tgcagagcgg cgtgcccagc   180
agattcagcg gcagcggctc cggcaccgac ttcaccctga ccatcagcag cctgcagccc   240
gaggacttcg ccacctacta ctgccagcag agcgacagca tcccctggac cttcggccag   300
ggcaccaagg tggaaatcaa g                                             321
```

<210> SEQ ID NO 77
<211> LENGTH: 354
<212> TYPE: DNA
<213> ORGANISM: Artificial Sequence
<220> FEATURE:
<223> OTHER INFORMATION: cDNA of VL of C4LB231

<400> SEQUENCE: 77

```
caggtccagc tggtgcagtc tggcgccgaa gtgaagaaac ccggcagcag cgtgaaggtg    60
tcctgcaagg ccagcggcgg caccttcagc agctacggca tcagctgggt ccgacaggcc   120
ccaggacagg gcctggaatg gatgggctgg atcagcccca tcttcggcaa caccaactac   180
gcccagaaat tccagggcag agtgaccatc accgccgacg agagcaccag caccgcctac   240
atggaactga gcagcctgcg gagcgaggac accgccgtgt actactgcgc cagaagccgg   300
tactacggcg acctggacta ctggggccag ggcaccctgg tcaccgtgtc ctct          354
```

<210> SEQ ID NO 78
<211> LENGTH: 387
<212> TYPE: DNA
<213> ORGANISM: Artificial Sequence
<220> FEATURE:
<223> OTHER INFORMATION: cDNA of VH of C4LB191

<400> SEQUENCE: 78

```
caggtgcagc tggtgcagag cggcgctcag gtgcagctgg tgcagtctgg cgccgaagtg    60
aagaaacctg gcgccagcat gaaggtgtcc tgcaaggcca gcggctacac cttcaccgac   120
tactacatcc actgggtgcg ccaggcccca ggcagggac tggaatgggt gggacggttc   180
aaccccaaca gcggcgacac caacggcgcc cagaaattcc agggcagagt gaccatgacc   240
```
cgggacacca gcatcagcac cgcctacatg gaactgaccc ggctgcggag cgacgacacc    300
gccgtgtacc actgtgccag agagggcgag ctggccggca tcttcttcga ctactggggc    360
cagggcaccc tggtgacagt gtccagc                                         387

<210> SEQ ID NO 79
<211> LENGTH: 318
<212> TYPE: DNA
<213> ORGANISM: Artificial Sequence
<220> FEATURE:
<223> OTHER INFORMATION: cDNA of VL of C4LB191

<400> SEQUENCE: 79
agctacgagc tgacccagcc ccccagcgtg tccgtgtctc ctggccagac cgccagcatc     60
acctgtagcg gcgacaagct gggcgacaaa tacgtgtcct ggaaccacca gaagcccggc    120
cagagccccg tgctggtgat ctaccaggac cggaagaggc ccagcggcat ccccgagaga    180
ttcagcggca gcaacagcgg caacaccgcc accctgacca tcagcggcac ccaggccatg    240
gacgaggccg actactactg ccaggcctgg gacagcagca ccgtggtgtt cggcggaggc    300
accaagctga ccgtgctg                                                   318

<210> SEQ ID NO 80
<211> LENGTH: 448
<212> TYPE: PRT
<213> ORGANISM: Artificial Sequence
<220> FEATURE:
<223> OTHER INFORMATION: FL mAb C4LB89 VH on IgG1sigma

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Trp Ile Ser Pro Ile Phe Gly Asn Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Tyr Gly Asp Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr

His Thr Cys Pro Pro Cys Pro Ala Pro Glu Ala Ala Gly Ala Ser Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Ala Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
            435                 440                 445

<210> SEQ ID NO 81
<211> LENGTH: 214
<212> TYPE: PRT
<213> ORGANISM: Artificial Sequence
<220> FEATURE:
<223> OTHER INFORMATION: Light chain of C4LB89

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Asn Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ile Pro Trp
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 82
<211> LENGTH: 448
<212> TYPE: PRT
<213> ORGANISM: Artificial Sequence
<220> FEATURE:
<223> OTHER INFORMATION: FL mAb C4LB89 VH on IgG1sigmaYTE

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Gly Ile Ser Trp Val Arg Gln Ala Pro Gly Gln Gly Leu Glu Trp Met
                35                  40                  45

Gly Trp Ile Ser Pro Ile Phe Gly Asn Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Tyr Tyr Gly Asp Leu Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Ser Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser Ala Glu Asp Pro
                260                 265                 270

Glu Val Lys Phe Asn Trp Tyr Val Asp Gly Val Glu Val His Asn Ala
```

```
                 275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 83
<211> LENGTH: 444
<212> TYPE: PRT
<213> ORGANISM: Artificial Sequence
<220> FEATURE:
<223> OTHER INFORMATION: FL mAb C4LB89 VH on IgG2sigma

<400> SEQUENCE: 83

Gln Val Gln Leu Val Gln Ser Gly Ala Glu Val Lys Lys Pro Gly Ser
1               5                   10                  15
Ser Val Lys Val Ser Cys Lys Ala Ser Gly Thr Phe Ser Ser Tyr
            20                  25                  30
Gly Ile Ser Trp Val Arg Gln Ala Pro Gly Gln Gly Leu Glu Trp Met
        35                  40                  45
Gly Trp Ile Ser Pro Ile Phe Gly Asn Thr Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Arg Tyr Tyr Gly Asp Leu Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Asn Phe Gly Thr Gln Thr Tyr Thr Cys Asn Val Asp His Lys Pro Ser
```

```
                195                 200                 205
Asn Thr Lys Val Asp Lys Thr Val Glu Arg Lys Cys Cys Val Glu Cys
            210                 215                 220
Pro Pro Cys Pro Ala Pro Ala Ala Ala Ser Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Ala Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Phe Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Thr
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys
        435                 440

<210> SEQ ID NO 84
<211> LENGTH: 119
<212> TYPE: PRT
<213> ORGANISM: Artificial Sequence
<220> FEATURE:
<223> OTHER INFORMATION: VH of C4LB119

<400> SEQUENCE: 84

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Tyr Ile Ser Trp Val Arg Gln Ala Pro Gly Gln Gly Leu Glu Trp Met
        35                  40                  45
Gly Ala Ile Asp Pro Tyr Phe Gly Tyr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Thr Gly Leu Asn Tyr Gly Gly Phe Asp Tyr Trp Gly Gln Gly
            100                 105                 110
Thr Leu Val Thr Val Ser Ser
```

<210> SEQ ID NO 85
<211> LENGTH: 107
<212> TYPE: PRT
<213> ORGANISM: Artificial Sequence
<220> FEATURE:
<223> OTHER INFORMATION: VL of C4LB119

<400> SEQUENCE: 85

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 86
<211> LENGTH: 121
<212> TYPE: PRT
<213> ORGANISM: Artificial Sequence
<220> FEATURE:
<223> OTHER INFORMATION: VH of C4LB83

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ile Pro Ile Phe Gly Asn Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Asp Phe Arg Gly Tyr Thr Lys Leu Asp Tyr Trp Gly
            100                 105                 110

Gln Gly Thr Leu Val Thr Val Ser Ser
        115                 120

<210> SEQ ID NO 87
<211> LENGTH: 107
<212> TYPE: PRT
<213> ORGANISM: Artificial Sequence
<220> FEATURE:
<223> OTHER INFORMATION: VL of C4LB83

<400> SEQUENCE: 87

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Gln Ser Ile Asn Asn Trp
            20              25              30

Leu Asn Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Phe Ser Phe Pro Tyr
            85              90              95

Thr Phe Gly Gln Gly Thr Lys Val Glu Ile Lys
            100             105
```